(12) United States Patent
Weinkam et al.

(10) Patent No.: US 10,681,805 B2
(45) Date of Patent: Jun. 9, 2020

(54) FLEXIBLE CIRCUIT STRUCTURES INCLUDING CONNECTION ARRANGEMENT CONNECTED TO LOAD MEASUREMENT LEAD

(71) Applicant: Kardium Inc., Burnaby (CA)

(72) Inventors: Daniel Robert Weinkam, Coquitlam (CA); Shane Fredrick Miller-Tait, North Vancouver (CA); Fernando Luis de Souza Lopes, Delta (CA)

(73) Assignee: KARDIUM INC., Burnaby (CA)

( * ) Notice: Subject to any disclaimer, the term of this patent is extended or adjusted under 35 U.S.C. 154(b) by 0 days.

(21) Appl. No.: 16/730,213

(22) Filed: Dec. 30, 2019

(65) Prior Publication Data

US 2020/0137875 A1  Apr. 30, 2020

Related U.S. Application Data

(63) Continuation of application No. 16/445,685, filed on Jun. 19, 2019, now Pat. No. 10,542,620, which is a
(Continued)

(51) Int. Cl.
*A61B 5/046* (2006.01)
*A61N 1/39* (2006.01)
(Continued)

(52) U.S. Cl.
CPC .............. *H05K 1/028* (2013.01); *A61B 5/046* (2013.01); *A61B 5/0422* (2013.01);
(Continued)

(58) Field of Classification Search
CPC .......... H05K 1/028; H05K 1/115; H05K 1/18; H05K 1/167; H05K 2201/09681;
(Continued)

(56) References Cited

U.S. PATENT DOCUMENTS 7,231,260 B2 * 6/2007 Wallace ................. A61N 1/057
607/115
8,906,011 B2   12/2014 Gelbart et al.
(Continued)

OTHER PUBLICATIONS

Notice of Allowance issued in U.S. Appl. No. 15/366,422 dated Oct. 6, 2017.
(Continued)

*Primary Examiner* — Timothy J Thompson
*Assistant Examiner* — Michael F McAllister
(74) *Attorney, Agent, or Firm* — Rossi, Kimms & McDowell LLP

(57) ABSTRACT

Some aspects of this disclosure generally are related to improving the robustness of a flexible circuit structure, for example, by providing fault-tolerant electrical pathways for flow of electric current through the flexible circuit structure. In some embodiments, such fault tolerance is enhanced by way of a conductive mesh provided between an adjacent pair of resistive elements. Some aspects are related to improved voltage, current, or voltage and current measurement associated with various pairs of adjacent resistive elements at least when the various pairs have differing distances between them.

13 Claims, 16 Drawing Sheets

Related U.S. Application Data continuation of application No. 16/260,704, filed on Jan. 29, 2019, now Pat. No. 10,375,827, which is a continuation of application No. 16/019,702, filed on Jun. 27, 2018, now Pat. No. 10,231,328, which is a continuation of application No. 15/862,010, filed on Jan. 4, 2018, now Pat. No. 10,028,376, which is a continuation of application No. 15/366,422, filed on Dec. 1, 2016, now Pat. No. 9,894,756.

(60) Provisional application No. 62/264,366, filed on Dec. 8, 2015.

(51) Int. Cl.

| | | |
|---|---|---|
| *G01K 7/16* | (2006.01) | |
| *H05K 1/18* | (2006.01) | |
| *H05K 1/02* | (2006.01) | |
| *H05K 1/11* | (2006.01) | |
| *G01K 1/02* | (2006.01) | |
| *G01K 13/00* | (2006.01) | |
| *A61B 18/14* | (2006.01) | |
| *A61B 5/042* | (2006.01) | |
| *A61B 18/12* | (2006.01) | |
| *A61N 1/05* | (2006.01) | |
| *H05K 1/16* | (2006.01) | |
| *A61B 18/00* | (2006.01) | |

(52) U.S. Cl.
CPC ...... *A61B 18/1206* (2013.01); *A61B 18/1492* (2013.01); *A61N 1/39* (2013.01); *G01K 1/026* (2013.01); *G01K 7/16* (2013.01); *G01K 13/002* (2013.01); *H05K 1/115* (2013.01); *H05K 1/18* (2013.01); *A61B 2018/00267* (2013.01); *A61B 2018/00357* (2013.01); *A61B 2018/00577* (2013.01); *A61B 2018/00702* (2013.01); *A61B 2018/00839* (2013.01); *A61B 2018/00988* (2013.01); *A61B 2562/166* (2013.01); *A61N 1/056* (2013.01); *H05K 1/167* (2013.01); *H05K 2201/0979* (2013.01); *H05K 2201/09681* (2013.01); *H05K 2201/10151* (2013.01); *H05K 2201/10507* (2013.01)

(58) Field of Classification Search
CPC . H05K 2201/0979; H05K 2201/10151; H05K 2201/10507; A61N 1/39; A61N 1/056; G01K 1/026; G01K 7/16; G01K 13/002; A61B 5/0422; A61B 5/046; A61B 18/1206; A61B 18/1492; A61B 2018/00267; A61B 2018/00357; A61B 2018/00577; A61B 2018/00702; A61B 2018/00839; A61B 2018/00988; A61B 2562/166
USPC ........................................................ 361/749
See application file for complete search history.

(56) References Cited

U.S. PATENT DOCUMENTS

| | | | |
|---|---|---|---|
| 8,920,411 B2 | 12/2014 | Gelbart et al. | |
| 9,501,192 B2* | 11/2016 | Deng | G06F 3/044 |
| 2004/0254471 A1* | 12/2004 | Hadjicostis | A61B 8/12 |
| | | | 600/459 |
| 2008/0178677 A1* | 7/2008 | Baumgartner | A61B 8/00 |
| | | | 73/606 |
| 2009/0131930 A1* | 5/2009 | Gelbart | A61B 5/4875 |
| | | | 606/41 |
| 2015/0097587 A1* | 4/2015 | Weaver | G06F 3/0418 |
| | | | 324/686 |
| 2015/0250539 A1* | 9/2015 | Gelbart | A61B 5/065 |
| | | | 600/481 |
| 2016/0161343 A1* | 6/2016 | Smith | B01L 3/502792 |
| | | | 374/185 |
| 2017/0164464 A1* | 6/2017 | Weinkam | H05K 1/18 |

OTHER PUBLICATIONS

Notice of Allowance issued in U.S. Appl. No. 15/862,010 dated Mar. 21, 2018.
Quayle Action issued in U.S. Appl. No. 16/019,702 mailed Aug. 9, 2018.
Notice of Allowance issued in U.S. Appl. No. 16/019,702 dated Nov. 1, 2018.
Notice of Allowance issued in U.S. Appl. No. 16/260,704 dated Mar. 27, 2019.
Quayle Action issued in copending U.S. Appl. No. 16/445,685 mailed Jul. 26, 2019.
Notice of Allowance issued in copending U.S. Appl. No. 16/445,685 dated Sep. 10, 2019.

* cited by examiner

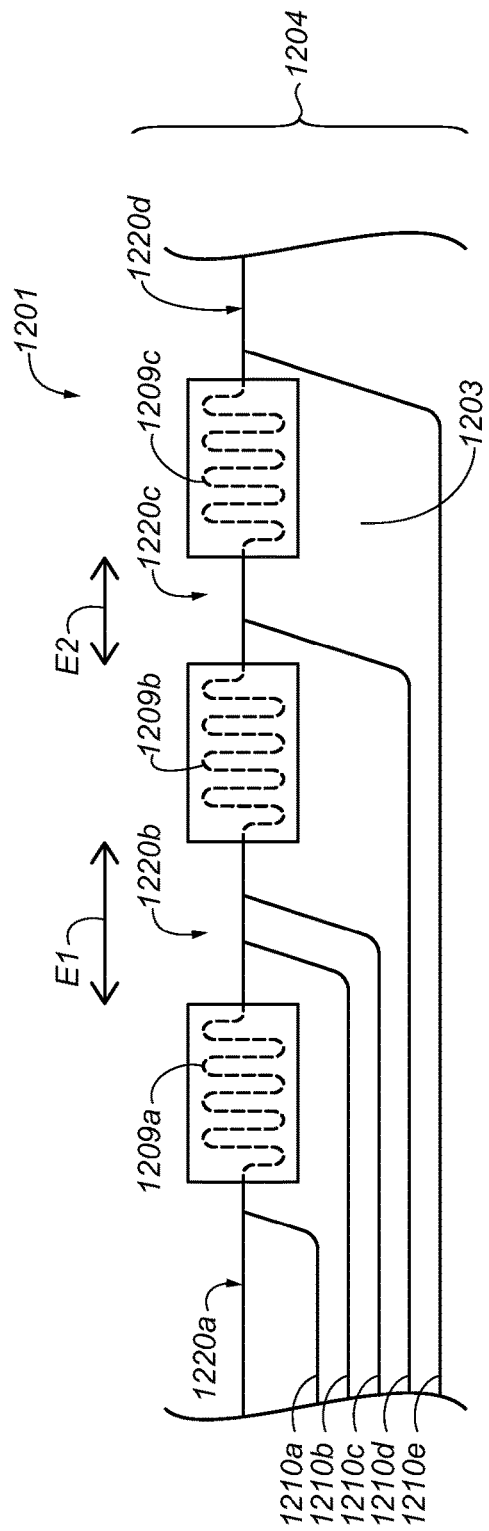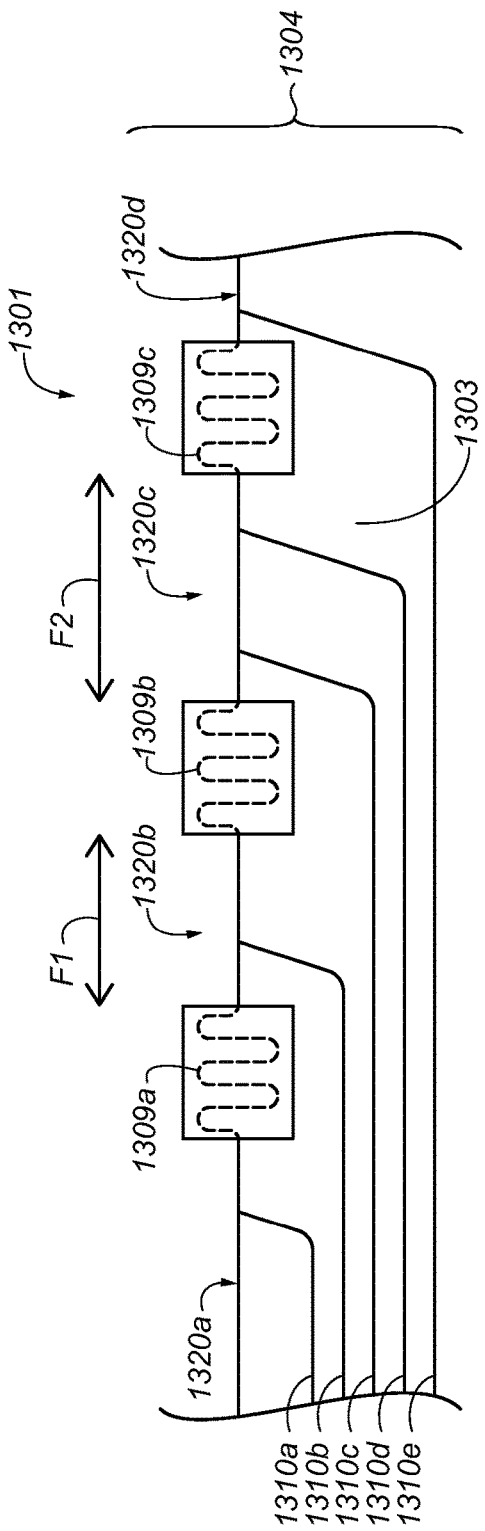

FLEXIBLE CIRCUIT STRUCTURES INCLUDING CONNECTION ARRANGEMENT CONNECTED TO LOAD MEASUREMENT LEAD

CROSS-REFERENCE TO RELATED APPLICATIONS

This application is a continuation of U.S. patent application Ser. No. 16/445,685, filed Jun. 19, 2019, which is a continuation of U.S. patent application Ser. No. 16/260,704, filed Jan. 29, 2019, now U.S. Pat. No. 10,375,827, issued on Aug. 6, 2019, which is a continuation of U.S. patent application Ser. No. 16/019,702, filed Jun. 27, 2018, now U.S. Pat. No. 10,231,328, issued on Mar. 12, 2019, which is a continuation of U.S. patent application Ser. No. 15/862,010, filed Jan. 4, 2018, now U.S. Pat. No. 10,028,376, issued on Jul. 17, 2018, which is a continuation of U.S. patent application Ser. No. 15/366,422, filed on Dec. 1, 2016, now U.S. Pat. No. 9,894,756, issued on Feb. 13, 2018, which claims the benefit of U.S. Provisional Application No. 62/264,366, filed Dec. 8, 2015, the entire disclosure of each of the applications cited in this paragraph is hereby incorporated herein by reference.

TECHNICAL FIELD

Some aspects of this disclosure generally are related to improving the robustness of flexible circuit structures.

BACKGROUND

Cardiac surgery was initially undertaken using highly invasive open procedures. A sternotomy, which is a type of incision in the center of the chest that separates the sternum was typically employed to allow access to the heart. In the past several decades, more and more cardiac operations are performed using intravascular or percutaneous techniques, where access to inner organs or other tissue is gained via a catheter.

Intravascular or percutaneous procedures benefit patients by reducing risk, complications and recovery time. However, the use of intravascular or percutaneous technologies also raises some particular challenges. Medical devices used in intravascular or percutaneous procedures need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During this procedure, physicians create specific patterns of lesions in the left and right atria to block various paths taken by the spurious electrical signals. Such lesions were originally created using incisions, but are now typically created by ablating the tissue with various techniques including radio-frequency (RF) energy, microwave energy, laser energy, electroporation and cryogenic techniques.

Various catheter-based devices are employed to intravascularly or percutaneously deliver (or sometimes through naturally occurring bodily orifices) various transducers along typically tortuous paths within a body. Recently, catheters employing flexible printed circuits have been successfully deployed in human patients. Flexible printed circuits allow for the economical manufacture of various transducers and their associated circuitry while providing a relatively small compact size that is desirable for percutaneous or intravascular procedures. This is especially important as the desire for increasing numbers of transducers increases. For example, catheters employing several hundreds of transducers have been produced by the applicant using flexible printed techniques.

The present inventors recognized that the stiffness of various portions of the flexible circuit structures may vary based on a number of factors. In this regard, the present inventors recognized that certain portions of the flexible circuit structure, such as the transducers, may be stiffer than other portions of the flexible structure, such as the conductors. The present inventors recognized that the spatial density of circuitry components in the various portions of the flexible circuit structure can affect the stiffness of these portions. For example, the present inventors recognized that portions of the flexible circuit structure corresponding to the transducers may have more conductive material than portions of the flexible circuit structure forming conductive elements connecting the transducers, resulting in the transducer portions being stiffer than the conductive element portions. In percutaneous or intravascular procedures, where the flexible circuit structure is delivered through a catheter, the present inventors recognized that the flexible circuit structure undergoes flexing as it moves through the body, for example, as it follows the natural contours of a bodily path such as a vascular vessel. Due to varying stiffness, the present inventors recognized that it is possible for various conductive elements (e.g., traces) of the flexible circuit to develop a crack due to stress forces imparted to the structure by the flexing. The present inventors also recognized that flexing may occur during a transition from a delivery configuration to an expanded or deployed configuration in some cases. The present inventors recognized that cracks may occur in a boundary region between a portion of the flexible circuit structure having relatively higher stiffness and a portion of the flexible circuit structure having relatively lower stiffness due to stress concentration effects. The present inventors recognized that cracks can lead to an open circuit rendering all or parts of the circuit unusable.

In this regard, the present inventors recognized that there is a need for at least flexible printed circuits that provide circuitry with enhanced durability and robustness suitable to withstand the rigors of percutaneous or intravascular delivery of the flexible printed circuits along tortuous bodily paths.

SUMMARY

At least the above-discussed need is addressed and technical solutions are achieved by various embodiments described in this disclosure. In some embodiments, flexible circuit structures are provided, the flexible circuit structures including circuitry exhibiting enhanced robustness and durability, especially during flexing required by applications such as, but not limited to, intravascular or percutaneous delivery of catheter devices employing said flexible printed structures. In some embodiments, the system or systems, or a portion thereof, may be percutaneously or intravascularly delivered to position various transducers provided by flexible printed circuit structures described in this disclosure within the bodily cavity. Various ones of the transducers may be used to treat tissue within a bodily cavity. Treatment may include tissue ablation by way of non-limiting example. Various ones of the transducers may be used to map tissue within the bodily cavity. Mapping may include mapping electrophysiological activity by way of non-limiting example. Mapping may be employed in a diagnosis of various conditions. Various ones of the transducers may be used to measure temperature within the bodily cavity. Various ones of the transducers may be used to stimulate tissue within the bodily cavity. Stimulation may include pacing by way of non-limiting example. Other characteristics and advantages will become apparent from the teachings herein to those of ordinary skill in the art. In some embodiments, a flexible circuit structure may be summarized as including an electrically-nonconductive substrate, and at least one electrically-conductive flexible circuit layer coupled, directly or indirectly, to the substrate. The at least one electrically-conductive flexible circuit layer includes conductive patterns including: a plurality of resistive elements, each resistive element providing at least part of a respective one of a plurality of transducers; and a plurality of conductive meshes. According to various embodiments, each conductive mesh of the plurality of conductive meshes electrically connects at least a respective adjacent pair of resistive elements of the plurality of resistive elements, According to various embodiments, the plurality of conductive meshes serially electrically connects the plurality of resistive elements to provide at least one electric current flow path through the plurality of resistive elements.

In some embodiments, each conductive mesh of the plurality of conductive meshes may include a plurality of electrical connection points to each resistive element of the respective adjacent pair of resistive elements. In some embodiments, each conductive mesh of the plurality of conductive meshes may include a plurality of electrical pathways between the resistive elements of each respective adjacent pair of resistive elements, and each conductive mesh of the plurality of conductive meshes may include a plurality of electrical connection points, each electrical connection point electrically connecting at least two of the plurality of electrical pathways between the resistive elements of the respective adjacent pair of resistive elements.

In some embodiments, each conductive mesh of the plurality of conductive meshes may include a plurality of conductive segments spatially arranged to provide a plurality of electrical pathways between the resistive elements of the respective adjacent pair of resistive elements, and each conductive segment of the plurality of conductive segments providing a respective portion of each of at least some of the plurality of electrical pathways. In some embodiments, each conductive mesh of the plurality of conductive meshes may include a plurality of electrical connection points electrically connecting at least two of the plurality of conductive segments to one of the resistive elements of the respective adjacent pair of resistive elements. In some embodiments, at least one of the plurality of electrical connection points of at least a first conductive mesh of the plurality of conductive meshes may be located at least adjacent one resistive element of the respective adjacent pair of resistive elements and may be electrically connected to at least two of the plurality of electrical connection points associated with the first conductive mesh located at least adjacent the other resistive element of the respective adjacent pair of resistive elements, the at least two of the plurality of electrical connection points not including any electrical connection point of the at least one of the plurality of electrical connection points. In some embodiments, at least one of the plurality of electrical connection points of at least a first conductive mesh of the plurality of conductive meshes may be located closer to one of the respective adjacent pairs of resistive elements than at least two of the plurality of electrical connection points associated with the first conductive mesh, and the at least one of the plurality of electrical connection points may be electrically connected to the at least two of the plurality of electrical connection points.

In some embodiments, each conductive mesh of the plurality of conductive meshes may include a plurality of conductive segments spatially arranged to provide a plurality of electrical pathways between the resistive elements of the respective adjacent pair of resistive elements, and each conductive segment of the plurality of conductive segments providing a respective portion of each of at least some of the plurality of electrical pathways. In some embodiments, each conductive mesh of the plurality of conductive meshes may include a plurality of electrical connection points electrically connecting at least two of the plurality of conductive segments to one of the resistive element of the respective adjacent pair of resistive elements. In some embodiments, the plurality of electrical connection points of each of at least a first conductive mesh of the plurality of conductive meshes may include a respective first electrical connection point set at least adjacent one resistive element of the respective adjacent pair of resistive elements and a respective second electrical connection point set at least adjacent the other resistive element of the respective adjacent pair of resistive elements, the second electrical connection point set not including any electrical connection point of the first electrical connection point set. In some embodiments, a total of the plurality of electrical pathways provided by the plurality of conductive segments of the first conductive mesh may exceed a total of the respective first electrical connection point set of the first conductive mesh, and may exceed a total of the respective second electrical connection point set of the first conductive mesh. In some embodiments, the respective first electrical connection point set of the first conductive mesh, the respective second electrical connection point set of the first conductive mesh, or each of the respective first electrical connection point set of the first conductive mesh and the respective second electrical connection point set of the first conductive mesh includes at least two electrical connection points.

In some embodiments, each conductive mesh of the plurality of conductive meshes may include a plurality of conductive segments spatially arranged to provide a plurality of electrical pathways between the resistive elements of the respective adjacent pair of resistive elements, and each conductive segment of the plurality of conductive segments providing a respective portion of each of at least some of the plurality of electrical pathways. In some embodiments, each conductive mesh of the plurality of conductive meshes may include a plurality of electrical connection points electrically connecting at least two of the plurality of conductive segments to one of the resistive element of the respective adjacent pair of resistive elements. In some embodiments, the plurality of electrical connection points of each conductive mesh of the plurality of conductive meshes may include a respective first electrical connection point set at least adjacent one resistive element of the respective adjacent pair of resistive elements and a respective second electrical connection point set at least adjacent the other resistive element of the respective adjacent pair of resistive elements, the second electrical connection point set not including any electrical connection point of the first electrical connection point set. According to some embodiments, for each of at least a first conductive mesh of the plurality of conductive meshes, at least a first one of the plurality of conductive segments of the first conductive mesh may extend along a path extending from a particular electrical connection point in the respective first electrical connection point set to a particular electrical connection point in the respective second electrical connection point set, the path arranged to avoid intersection along the path between the first one of the plurality of conductive segments of the first conductive mesh and any other one of the plurality of conductive segments of the first conductive mesh.

In some embodiments, the plurality of electrical connection points of each conductive mesh of the plurality of conductive meshes may include a respective first electrical connection point set at least adjacent one resistive element of the respective adjacent pair of resistive elements and a respective second electrical connection point set at least adjacent the other resistive element of the respective adjacent pair of resistive elements, the second electrical connection point set not including any electrical connection point of the first electrical connection point set. According to some embodiments, for each of at least a first conductive mesh of the plurality of conductive meshes, each electrical pathway of at least some of the respective plurality of electrical pathways does not have a conductive segment in common with any other electrical pathway of the respective plurality of electrical pathways.

In some embodiments, the plurality of electrical connection points of each conductive mesh of the plurality of conductive meshes may include a respective first electrical connection point set at least adjacent one resistive element of the respective adjacent pair of resistive elements and a respective second electrical connection point set at least adjacent the other resistive element of the respective adjacent pair of resistive elements, the second electrical connection point set not including any electrical connection point of the first electrical connection point set. According to some embodiments, for each of at least a first conductive mesh of the plurality of conductive meshes, a first electrical pathway of the respective plurality of electrical pathways extends from a particular electrical connection point in the first electrical connection point set to a particular electrical connection point in the second electrical connection point set through a single one of the plurality of conductive segments of the first conductive mesh.

In some embodiments, the plurality of electrical connection points of each conductive mesh of the plurality of conductive meshes may include a respective first electrical connection point set at least adjacent one resistive element of the respective adjacent pair of resistive elements and a respective second electrical connection point set at least adjacent the other resistive element of the respective adjacent pair of resistive elements, the second electrical connection point set not including any electrical connection point of the first electrical connection point set. According to some embodiments, for each of at least a first conductive mesh of the plurality of conductive meshes, at least a first group of the plurality of conductive segments of the first conductive mesh are arranged in a branched arrangement extending from a particular electrical connection point in the respective first electrical connection point set to each of at least two particular electrical connection points in the respective second electrical connection point set.

In some embodiments, each conductive mesh of the plurality of conductive meshes may include a plurality of conductive segments spatially arranged to provide a plurality of electrical pathways between the resistive elements of the respective adjacent pair of resistive elements, and each conductive segment of the plurality of conductive segments providing a respective portion of each of at least some of the plurality of electrical pathways. In some embodiments, the plurality of conductive segments of at least a first conductive mesh of the plurality of conductive meshes may include a first conductive segment set and a second conductive segment set, each segment in the first conductive segment set extending in a first direction and each segment in the second conductive segment set extending in a second direction, the first direction being perpendicular or oblique to the second direction, and at least one of the conductive segments in the first conductive segment set intersecting with at least one of the conductive segments in the second conductive segment set. In some embodiments, for each of at least a first conductive mesh of the plurality of conductive meshes, each of at least some of the plurality of conductive segments of the first conductive mesh may be arranged to provide an unbranched pathway extending continuously between a first resistive element of the respective adjacent pair of resistive elements and a second resistive element of the respective adjacent pair of resistive elements. In some embodiments, for each of a least a first conductive mesh of the plurality of conductive meshes, at least some of the plurality of conductive segments of the first conductive mesh may be arranged to provide a branched pathway extending continuously between a first resistive element of the respective adjacent pair of resistive elements and a second resistive element of the respective adjacent pair of resistive elements.

According to some embodiments, each conductive mesh of at least some of the plurality of conductive meshes may electrically connect the respective adjacent pair of resistive elements via a respective plurality of conductive segments, each conductive segment of at least some of the respective plurality of conductive segments not contacting any other conductive segment of the respective plurality of conductive segments in a region spanning an edge of a first resistive element of the respective adjacent pair of resistive elements and an edge of a second resistive element of the respective adjacent pair of resistive elements.

In some embodiments, each conductive mesh of at least some of the plurality of conductive meshes electrically may connect the respective adjacent pair of resistive elements via a respective plurality of conductive segments, each conductive segment of at least some of the respective plurality of segments arranged to provide an unbranched pathway extending continuously between a first resistive element of the respective adjacent pair of resistive elements and a second resistive element of the respective adjacent pair of resistive elements. In some embodiments, each conductive mesh of at least some of the plurality of conductive meshes electrically connects the respective adjacent pair of resistive elements via a respective plurality of conductive segments, and a group of at least some of the respective plurality of conductive segments may be arranged to provide a branched pathway extending continuously between a first resistive element of the respective adjacent pair of resistive elements and a second resistive element of the respective adjacent pair of resistive elements.

In some embodiments, each conductive mesh of the plurality of conductive meshes may include a first electrical connection point set located at least adjacent a first resistive element of the respective adjacent pair of resistive elements and a second electrical connection point set located at least adjacent a second resistive element of the respective adjacent pair of resistive elements. According to various embodiments, each conductive mesh of the plurality of conductive meshes may electrically connect the respective adjacent pair of resistive elements via a respective plurality of electrical pathways electrically connected to a respective pair of electrical connections points of a plurality of pairs of electrical connection points, each respective pair of electrical connection points of the respective plurality of pairs of electrical connection points including a respective first electrical connection point from the first electrical connection point set and a respective second electrical connection point from the second electrical connection point set. In some embodiments, each respective pair of electrical connection points of the respective plurality of pairs of electrical connection points may be different than every other pair of electrical connection points of the respective plurality of pairs of electrical connection points.

In some embodiments, the electrically nonconductive substrate may include a plurality of electrically nonconductive layers, and the at least one electrically-conductive flexible circuit layer may include a plurality of electrically-conductive flexible circuit layers that are interleaved with the plurality of electrically nonconductive layers. In some embodiments, the plurality of resistive elements may be temperature sensors. The at least one electrically-conductive flexible circuit layer may include a plurality of electrically-conductive flexible circuit layers, and each of at least some of the plurality of conductive meshes may electrically connect at least a respective adjacent pair of temperature sensors of the temperature sensors by at least one via arranged to electrically connect different ones of the electrically conductive flexible circuit layers.

In some embodiments, the at least one electrically-conductive flexible circuit layer may include a plurality of electrically-conductive flexible circuit layers, and at least a first one of the plurality of electrically-conductive flexible circuit layers may include an electrode. At least a second one of the plurality of electrically-conductive flexible circuit layers may include at least one resistive element of the plurality of resistive elements and at least one conductive mesh of the plurality of conductive meshes. In some embodiments, at least a portion of the one conductive mesh of the plurality of conductive meshes may spatially overlap at least a portion of the electrode or may be spatially overlapped by at least a portion of the electrode.

In some embodiments, the flexible circuit structure may include a plurality of measurement leads electrically connected to a measurement circuit, respective pairs of measurement leads of the plurality of measurement leads positioned to sense voltage across, or current flowing through each resistive element of each of at least some of the plurality of resistive elements. According to some embodiments, each of the plurality of measurement leads may be electrically connected to a corresponding conductive mesh of the plurality of conductive meshes. In some embodiments, at least one of the plurality of measurement leads may electrically connect to one conductive mesh of the plurality of conductive meshes at a plurality of electrical connection points. According to some embodiments, a first measurement lead of the plurality of measurement leads electrically connects to a first conductive mesh of the plurality of conductive meshes at a first electrical connection point set, and a second measurement lead of the plurality of measurement leads electrically connects to a second conductive mesh of the plurality of conductive meshes at a second electrical connection point set, the second set comprising a greater number of electrical connection points than the first set.

In some embodiments, each resistive element may include a serpentine form.

In some embodiments, each conductive mesh of at least some of the plurality of conductive meshes may electrically connect the respective adjacent pair of resistive elements via a respective plurality of electrical pathways, at least part of one electrical pathway of at least some of the respective plurality of electrical pathways prevented from merging with at least part of another electrical pathway of the at least some of the respective plurality of electrical pathways by a region of electrically-nonconductive material located between the at least part of the one electrical pathway and the at least part of the another electrical pathway.

In some embodiments, each conductive mesh of the plurality of conductive meshes may include a plurality of conductive segments spatially arranged to provide a plurality of electrical pathways between the resistive elements of the respective adjacent pair of resistive elements, and each conductive segment of the plurality of conductive segments providing a respective portion of each of at least some of the plurality of electrical pathways. According to some embodiments, for each of at least a first conductive mesh of the plurality of conductive meshes, the plurality of conductive segments of the first conductive mesh may be arranged to, at least in part, form a plurality of openings, each opening of the plurality of openings surrounding a respective region of the electrically-nonconductive substrate. In some embodiments, the first conductive mesh may extend along a first direction from a first resistive element of the respective adjacent pair of resistive elements toward a second resistive element of the respective adjacent pair of resistive elements, and at least a first group of the plurality of openings may be arranged along one of the first direction and a second direction, the second direction orthogonal to the first direction. In some embodiments, at least a second group of the plurality of openings may be arranged along the other of the one of the first direction and the second direction. In some embodiments, the first and the second groups of openings may share at least one opening of the plurality of openings.

Various flexible circuit structures may include combinations and subsets of all the flexible circuit structures summarized above.

In some embodiments, a flexible circuit structure may be summarized as including at least one nonconductive flexible layer including an electrically insulative material, and one or more conductive flexible circuit layers proximate the at least one nonconductive flexible layer, each of the one or more conductive flexible circuit layers including an electrically conductive material. According to various embodiments, the one or more conductive flexible circuit layers includes or include a plurality of electrical loads electrically connected in series by a plurality of electrical-connection-arrangements, each electrical-connection-arrangement electrically connecting a respective adjacent pair of electrical loads of the plurality of electrical loads; and a plurality of electrical-load-measurement leads, each electrically connected to at least one of the plurality of electrical loads. In some embodiments, a first electrical-connection-arrangement of the plurality of electrical-connection-arrangements spans a first distance between a first respective adjacent pair of electrical loads of the plurality of electrical loads, and a second electrical-connection arrangement of the plurality of electrical-connection-arrangements spans a second distance between a second respective adjacent pair of electrical loads of the plurality of electrical loads. According to some embodiments, the first electrical-connection-arrangement may be electrically connected to at least one of the plurality of electrical-load-measurement leads, and the second electrical-connection-arrangement may be electrically connected to a greater number of the plurality of electrical-load-measurement leads than the number of the plurality of electrical-load-measurement leads connected to by the first electrical-connection-arrangement. In various embodiments, each of the plurality of loads provides at least a portion of a respective one of a plurality of transducers. In various embodiments, each of the plurality of transducers is patterned on or in the flexible circuit structure.

In some embodiments, the first distance and the second distance may be different. In some embodiments, the second distance may be greater than the first distance. In some embodiments, an electrical resistance of the second electrical-connection-arrangement may be greater than an electrical resistance of the first electrical-connection-arrangement. In some embodiments, the second distance may be greater than the first distance and an electrical resistance of the second electrical-connection-arrangement may be greater than an electrical resistance of the first electrical-connection-arrangement.

In some embodiments, at least the first electrical-connection-arrangement or the second electrical-connection-arrangement may include one or more conductive meshes, each conductive mesh including a plurality of conductive segments spatially arranged to provide a plurality of electrical pathways defining a respective portion of an electric current flow path, the respective portion of the electric current flow path located between the electrical loads of the respective adjacent pair of electrical loads, and each conductive segment of the plurality of conductive segments providing a respective portion of the plurality of electrical pathways.

In some embodiments, each of the first electrical-connection-arrangement and the second electrical-connection-arrangement may include one or more conductive meshes, each conductive mesh including a plurality of conductive segments spatially arranged to provide a plurality of electrical pathways between the electrical loads of the respective adjacent pair of electrical loads, and each conductive segment of the plurality of conductive segments providing a respective portion of each of at least some of the plurality of electrical pathways. A total of the conductive meshes comprised by the second electrical-connection-arrangement may be greater than a total of the conductive meshes comprised by the first electrical-connection-arrangement according to various embodiments.

In some embodiments, each of the first electrical-connection-arrangement and the second electrical-connection-arrangement may include a respective one or more conductive meshes, each conductive mesh including a plurality of conductive segments spatially arranged to provide a plurality of electrical pathways between the electrical loads of the respective adjacent pair of electrical loads, and each conductive segment of the plurality of conductive segments providing a respective portion of each of at least some of the plurality of electrical pathways. Each conductive mesh may be directly connected to a respective one of a set of the plurality of measurement leads according to various embodiments.

In some embodiments, the at least one nonconductive flexible layer may include a plurality of nonconductive flexible layers, and the one or more conductive flexible circuit layers may include a plurality of conductive flexible circuit layers that are interleaved with the plurality of electrically nonconductive flexible layers.

In some embodiments, the plurality of electrical loads may be temperature sensors. According to various embodiments, the one or more conductive flexible circuit layers may include a plurality of conductive flexible circuit layers, and at least the first electrical-connection-arrangement or the second electrical-connection-arrangement may electrically connect at least a respective adjacent pair of temperature sensors of the temperature sensors by at least one via arranged to electrically connect different ones of the plurality of conductive flexible circuit layers.

In some embodiments, each electrical load of the plurality of electrical loads may be provided at least in part by a respective one of a plurality of temperature sensors.

Various flexible circuit structures may include combinations and subsets of all the flexible circuit structures summarized above.

In some embodiments, a flexible circuit structure may be summarized as including at least one nonconductive flexible layer including an electrically insulative material, and one or more conductive flexible circuit layers proximate the at least one nonconductive flexible layer, the one or more conductive flexible circuit layers including an electrically conductive material. According to various embodiments, the one or more conductive flexible circuit layers includes or include an electric-serial-circuitry-connection-arrangement including a serial-electrical-connection order of: a first electrical-load-measurement lead, a first electrical load, a second electrical-load-measurement lead, a third-electrical-load-measurement lead, a second electrical load, a fourth-electrical-load-measurement lead, a third electrical load, and a fifth-electrical-load-measurement lead. In various embodiments, a first distance between the first electrical load and the second electrical load is greater than a distance between the second electrical load and the third electrical load. In various embodiments, the first electrical-load-measurement lead and the second electrical-load-measurement lead may be positioned to sense voltage across, or current flowing through the first electrical load. In various embodiments, the third electrical-load-measurement lead and the fourth electrical-load-measurement lead may be positioned to sense voltage across, or current flowing through, the second electrical load. In various embodiments, the fourth electrical-load-measurement lead and the fifth electrical-load-measurement lead may be positioned to sense voltage across, or current flowing through, the third electrical load. In various embodiments, each of the plurality of loads provides at least a portion of a respective one of a plurality of transducers. In various embodiments, each of the plurality of transducers is patterned on or in the flexible circuit structure.

Various flexible circuit structures may include combinations and subsets of all the flexible circuit structures summarized above.

In some embodiments, a flexible circuit structure may be summarized as including at least one nonconductive flexible layer including an electrically insulative material, and one or more conductive flexible circuit layers proximate the at least one nonconductive flexible layer, the one or more conductive flexible circuit layers including an electrically conductive material. According to various embodiments, the one or more conductive flexible circuit layers includes or include a plurality of electrical loads electrically connected in series, and a plurality of electrical-load-measurement leads, each electrically connected to at least one of the plurality of electrical loads. According to various embodiments, a first pair of leads of the plurality of electrical-load-measurement leads may be positioned to sense voltage across, or current flowing through, a first electrical load of the plurality of electrical loads. According to various embodiments, a second pair of leads of the plurality of electrical-load-measurement leads may be positioned to sense voltage across, or current flowing through, a second electrical load of the plurality of electrical loads. According to various embodiments, a third pair of leads of the plurality of electrical-load-measurement leads may be positioned to sense voltage across, or current flowing through, a third electrical load of the plurality of electrical loads. According to various embodiments, the first electrical load is adjacent the second electrical load in the series, and the second electrical load and the third electrical load are adjacent in the series. According to various embodiments, the first pair of leads and the second pair of leads share a same one of the plurality of electrical-load-measurement leads. According to various embodiments, the second pair of leads does not share any of the plurality of electrical-load-measurement leads with the third pair of leads. In various embodiments, each of the plurality of loads provides at least a portion of a respective one of a plurality of transducers. In various embodiments, each of the plurality of transducers is patterned on or in the flexible circuit structure.

In some embodiments, a distance spanning the first electrical load and the second electrical load may be different than a distance spanning the second electrical load and the third electrical load. In some embodiments, a distance spanning the second electrical load and the third electrical load may be greater than a distance spanning the first electrical load and the second electrical load.

In some embodiments, an electrical resistance of a portion of the flexible circuit structure that serially electrically connects the first electrical load to the second electrical load may be different than an electrical resistance of a portion of the flexible circuit structure that serially electrically connects the second electrical load to the third electrical load. In some embodiments, an electrical resistance of a portion of the flexible circuit structure that serially electrically connects the second electrical load to the third electrical load may be greater than an electrical resistance of a portion of the flexible circuit structure that serially electrically connects the first electrical load to the second electrical load.

In some embodiments, the flexible circuit structure may further include a plurality of electrical-connection-arrangements, each electrical-connection-arrangement electrically connecting a respective adjacent pair of electrical loads of the plurality of electrical loads. According to various embodiments, each of at least some of the plurality of electrical-connection-arrangements may include a set of one or more conductive meshes, each conductive mesh including a plurality of conductive segments spatially arranged to provide a plurality of electrical pathways defining a respective portion of an electric current flow path, the respective portion of the electric current flow path located between the electrical loads of the respective adjacent pair of electrical loads, and each conductive segment of the plurality of conductive segments providing a respective portion of the plurality of electrical pathways. In some embodiments, each conductive mesh may be directly connected to a respective one or more of the plurality of measurement leads. In some embodiments, a first electrical-connection-arrangement of the at least some of the plurality of electrical-connection-arrangements may electrically connect the first electrical load and the second electrical load, and a second electrical-connection-arrangement of the at least some of the plurality of electrical-connection-arrangements may electrically connect the second electrical load and the third electrical load. A total of the conductive meshes comprised by the second electrical-connection-arrangement may be greater than a total of the conductive meshes comprised by the first electrical-connection-arrangement according to some embodiments.

In some embodiments, the at least one nonconductive flexible layer may include a plurality of nonconductive flexible layers, and the one or more conductive flexible circuit layers may include a plurality of conductive flexible circuit layers that are interleaved with the plurality of electrically nonconductive flexible layers.

In some embodiments, the flexible circuit structure may further include a plurality of electrical-connection-arrangements, each electrical-connection-arrangement electrically connecting a respective adjacent pair of electrical loads of the plurality of electrical loads. In some embodiments, the plurality of electrical loads may be temperature sensors. In some embodiments, the one or more conductive flexible circuit layers may include a plurality of conductive flexible circuit layers, and at least a first one of the plurality of electrical-connection-arrangements may electrically connect at least a respective adjacent pair of temperature sensors of the temperature sensors by at least one via arranged to electrically connect different ones of the electrically conductive flexible circuit layers. In some embodiments, the first one of the plurality of electrical-connection-arrangements may electrically connect the respective adjacent pair of temperature sensors corresponding to the first electrical load and the second electrical load.

In some embodiments, each electrical load of the plurality of electrical loads may be provided at least in part by a respective one of a plurality of temperature sensors.

Various flexible circuit structures may include combinations and subsets of all the flexible circuit structures summarized above.

BRIEF DESCRIPTION OF THE DRAWINGS

It is to be understood that the attached drawings are for purposes of illustrating aspects of various embodiments and may include elements that are not to scale.

FIG. 12 is a schematic representation of a flexible circuit structure that includes a patterned conductive layer, according to various example embodiments.

FIG. 13 is a schematic representation of a flexible circuit structure that includes a patterned conductive layer, according to various example embodiments.

DETAILED DESCRIPTION

Figure 1:
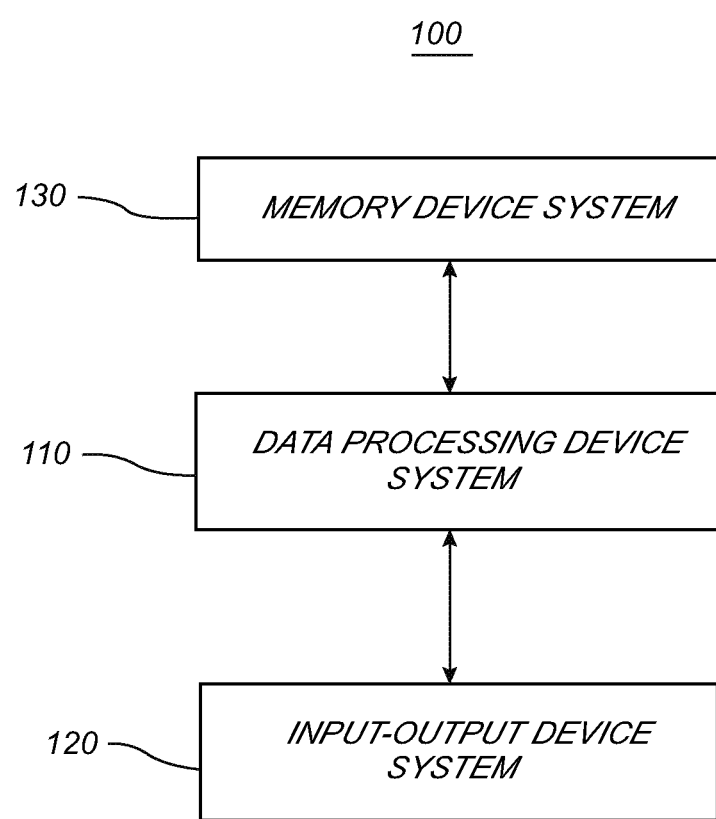
FIG. 1 is a schematic representation of a medical device system according to various example embodiments, where the medical device system may include a data processing device system, an input-output device system, and a memory device system, according to some embodiments.

Some embodiments of the present invention pertain to flexible circuit structures including flexible conductive and nonconductive layers. The flexible circuit structures can be subject to strain due to movement (e.g., bending, flexing) of various flexible layers comprised by the flexible circuit structures. This may result in cracks in various conductive layers, which can lead to an open circuit or an otherwise impaired circuit. Cracks may also occur in various conductive layers due to manufacturing defects in the flexible circuit structures or wear and tear of devices employing the flexible circuit structures. Although such conditions may arise in other contexts, they may be particularly important in medical device systems where consequences of an open or otherwise impaired circuit might be associated with elevated risk or prolonged procedure times. For example, in procedures configured to treat atrial fibrillation, various transducers are employed to selectively deliver RF energy to various tissue structures within a bodily cavity (e.g., a tissue cavity such as an intra-cardiac cavity). The energy delivered to the tissue structures may be sufficient for ablating portions of the tissue structures. In various embodiments, the tissue structures are typically formed from non-fluidic tissue and the energy sufficient for ablating portions of the tissue structures is typically referred to as sufficient for tissue ablation. It is noted that in cases in which the transducers and associated circuitry are provided by flexible printed circuit structures, the presence of stress-induced or otherwise formed or induced open or otherwise impaired circuits in the flexible printed circuit structures may adversely impact the ability to deliver the energy required for tissue ablation. It should be noted that cracks or other breakages in a flexible circuit structure may cause open or otherwise impaired circuits to occur in any one or more of an electrode-based circuit, a resistive element-based circuit, a voltage-based or current-based measurement circuit, or any other part of a transducer-based circuit.

Various example embodiments described herein provide robust and redundant circuit features that permit continued operation of all or some portions of the flexible circuit structure when some portions of the flexible circuit structure are rendered open or impaired due to cracks or other breakages. Various example embodiments described herein provide robust flexible circuit features with enhanced resistance to cracks or other breakages.

In some embodiments, various transducers may include electrodes or resistive elements to detect, sense, or measure various conditions. The electrodes may also be configured to deliver energy to affect the surroundings, such as bodily tissue, in some embodiments. For example, various transducers produced by flexible printed circuit structures may be provided to measure properties such as a temperature of tissue areas proximate the various transducers. In some embodiments, elements of such transducers may be formed using resistive circuit elements providing a function of detecting temperature. These resistive elements may be termed resistance temperature detectors according to some embodiments. The resistive elements may be connected in a chain such that a current flowing through each resistive element is substantially the same. In some embodiments, additional circuits, such as voltage or current measurement circuits, may connect to the resistive elements to measure voltage across each resistive element and electric current that flows through the chain of resistive elements. In some embodiments, the resistive elements may form resistance temperature detectors to measure the temperature proximate the surrounding tissue. In some embodiments, the resistance temperature detectors may measure temperature at least proximate the surrounding tissue to determine whether the tissue is fluidic or non-fluidic. It should be noted that some embodiments do not require direct contact between at least part of the transducer and the surrounding tissue for measurement of various properties such as the temperature of the surrounding tissue. In some embodiments, the resistance temperature detectors may measure temperature at least proximate the surrounding tissue to determine whether an associated transducer is, or is not, in contact with a particular neighboring tissue.

Figure 14:
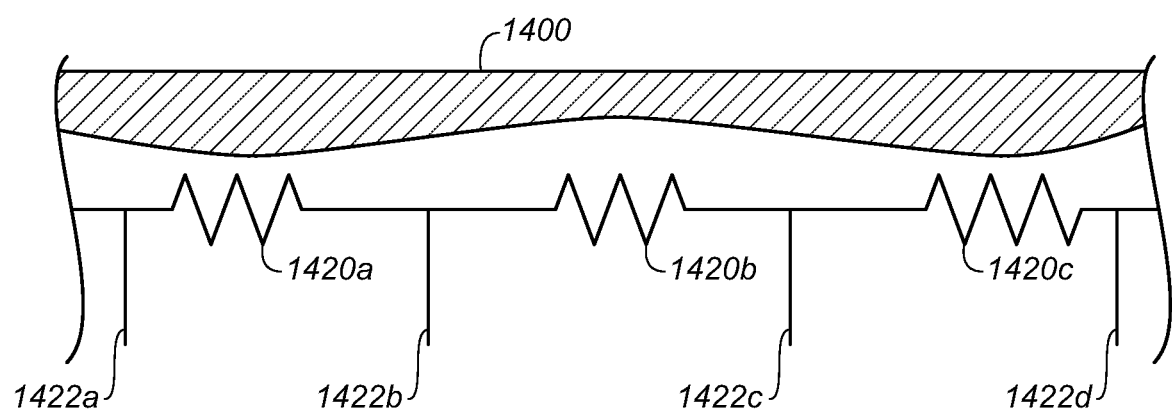
FIG. 14 is a schematic representation of a portion of a prior art flexible circuit structure.

Various arrangements of transducer elements electrically connected together in a chain-like fashion are described in commonly assigned U.S. Pat. No. 8,906,011, issued Dec. 9, 2014. These various chain-like arrangements reduce the number of leads required to measure various properties such as temperature with the transducer elements, thereby reducing the real estate requirements of the transducers and the leads and thereby allowing the use of several hundreds of transducers within the spatial constraints imposed by most catheter-based procedures. The described transducers elements are made from a material that has a readily detectable change in the resistance with temperature. Changes in temperature correlate with changes in resistance, and the resistance may be determined by measuring the voltage across the transducer element (resistance temperature detector—RTD) for a given current, or alternatively, by measuring the current flowing through the transducer element for a given voltage applied across the transducer element (e.g., via a Wheatstone bridge circuit). FIG. 14 is a conventional chain-like arrangement of resistive transducer elements 1420*a*, 1420*b* and 1420*c* (collectively, resistive transducer elements 1420) arranged proximate non-fluidic tissue 1400. To determine temperature by measuring the resistance of transducer element 1420b, the voltage at lead 1422a and lead 1422b should be made equal and the voltage at a lead 1422c and lead 1422d should be made equal, but to a different voltage than that of lead 1422a and lead 1422b (leads 1422a, 1422b, 1422c and 1422d collectively referred to as leads 1422). In this condition, a small (possibly negligible) current may flow through transducer element 1420a and transducer element 1420c. Therefore, the current flowing through lead 1422b and lead 1422c is essentially the same as the current flowing through the transducer element 1420b, and the resistance of the transducer element 1420b may be calculated in a straightforward manner using the equation V=I*R, known in the art. It is noted that the resistance of an electrically conductive metal (e.g., copper) changes based on the temperature of the electrically conductive metal as described later in this disclosure. Accordingly, temperature changes and temperatures may be determined based upon the measured resistance. It is noted that adjacent transducer elements 1420 sharing common leads 1422 may, e.g., be used in a one-dimensional line of connected transducer elements 1420 or may be used in two-dimensional or three-dimensional arrays of connected transducer elements 1420.

Figure 15:
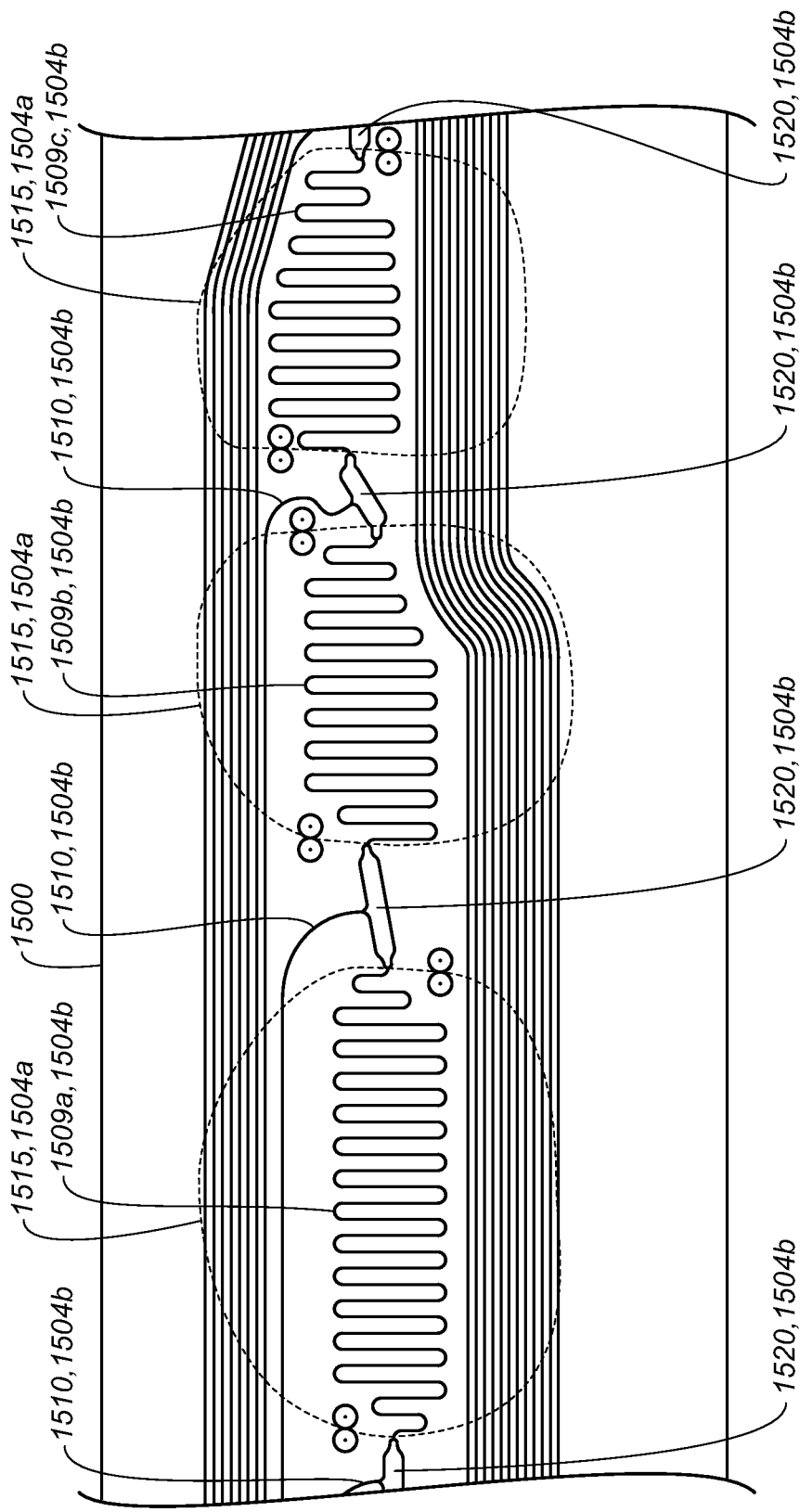
FIG. 15 is a schematic representation of a transducer-based device that includes a flexible circuit.

FIG. 15 is a plan view of a portion of a flexible circuit structure 1500 that includes a plurality of conductive flexible circuit layers interleaved with a plurality of nonconductive flexible circuit layers according to various flexible circuit manufacturing techniques. It is noted in FIG. 15 that only two conductive flexible circuit layers 1504a and 1504b are called out and are tangentially indicated by various respective elements that are patterned in them. In the plan view of FIG. 15, it is to be understood that the respective elements formed in the conductive flexible circuit layer 1504b are overlapped by at least one nonconductive circuit layer (not shown in FIG. 15) and by at least the conductive flexible layer 1504a. A plurality of resistive elements 1509 (three called out by reference symbols 1509a, 1509b and 1509c in FIG. 15) are patterned in conductive flexible circuit layer 1504b. In this particular case, the resistive elements 1509 are resistance temperature detectors. The resistive elements 1509 are electrically connected in series by a plurality of conductive elements 1520 that are patterned in conductive flexible circuit layer 1504b. A group of voltage measurements leads 1510 patterned in conductive flexible circuit layer 1504b are electrically connected to the resistive elements 1509 to measure voltage across each of resistive elements 1509 (e.g., in a manner similar to that described with respect to FIG. 14). A plurality of electrodes 1515 are patterned in conductive flexible circuit layer 1504a, each electrode 1515 overlapping at least a respective one of the resistive elements 1509 as viewed in the plan view of FIG. 15. It is noted that each conductive element 1520 is wider than the corresponding adjacent resistive element 1509 to reduce the resistance of the connection between the corresponding adjacent resistive elements 1509. The transition in width from the conductive element 1520 to the adjacent resistive element 1509 can cause stress concentrations that can lead to cracks in the conductive element 1520 itself or in a connection between the conductive element 1520 and adjacent resistive element 1509 when the flexible circuit structure 1500 is moved (e.g., flexed). Cracks can occur in the conductive element 1520 itself, or in a connection area between the conductive element 1520 and adjacent resistive element 1509 in regions near the edges of the electrodes 1515 because the electrodes 1515 are relatively stiffer than other conductive components (e.g., the electrodes 1515 typically include a relatively large electrically conductive surface region which provides relatively higher stiffness). These cracks may ultimately lead to open circuits. It is noted that if an open circuit condition develops (e.g., by a stress-induced failure in the connecting circuitry) in the chain of resistive elements 1509, the ability of all the resistive elements 1509 to detect respective temperatures may be adversely impacted. If an open circuit occurs in one of the voltage measurement leads 1510 or conductive element 1520, the ability of at least some of the resistive elements 1509 to detect respective temperatures may be adversely impacted.

In this regard, some embodiments of the present invention facilitate multiplicity, redundancy, and failure tolerance in the circuit so that at least some of these unintended or undesired circumstances can be avoided. However, it can be seen that various embodiments need not be limited to intra-body medical devices or even medical devices more generally and, instead, have broader applicability.

In this regard, in the descriptions herein, certain specific details are set forth in order to provide a thorough understanding of various embodiments of the invention. However, one skilled in the art will understand that the invention may be practiced at a more general level without one or more of these details. In other instances, well-known structures have not been shown or described in detail to avoid unnecessarily obscuring descriptions of various embodiments of the invention.

Any reference throughout this specification to "one embodiment" or "an embodiment" or "an example embodiment" or "an illustrated embodiment" or "a particular embodiment" and the like means that a particular feature, structure or characteristic described in connection with the embodiment is included in at least one embodiment. Thus, any appearance of the phrase "in one embodiment" or "in an embodiment" or "in an example embodiment" or "in this illustrated embodiment" or "in this particular embodiment" or the like in this specification is not necessarily all referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more, and the word "subset" is intended to mean a set having the same or fewer elements of those present in the subset's parent or superset.

Further, the phrase "at least" is or may be used herein at times merely to emphasize the possibility that other elements may exist besides those explicitly listed. However, unless otherwise explicitly noted (such as by the use of the term "only") or required by context, non-usage herein of the phrase "at least" nonetheless includes the possibility that other elements may exist besides those explicitly listed. For example, the phrase, 'based at least on A' includes A as well as the possibility of one or more other additional elements besides A. In the same manner, the phrase, 'based on A' includes A, as well as the possibility of one or more other additional elements besides A. However, the phrase, 'based only on A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase, 'configured only to A' means a configuration to perform only A.

The word "device", the word "machine", and the phrase "device system" all are intended to include one or more physical devices or sub-devices (e.g., pieces of equipment) that interact to perform one or more functions, regardless of whether such devices or sub-devices are located within a same housing or different housings. However, it may be explicitly specified that a device or machine or device system reside entirely within a same housing to exclude embodiments where the respective device, machine, or device system reside across different housings. The word "device" may equivalently be referred to as a "device system".

Further, the phrase "in response to" may be used in this disclosure. For example, this phrase might be used in the following context, where an event A occurs in response to the occurrence of an event B. In this regard, such phrase includes, for example, that at least the occurrence of the event B causes or triggers the event A.

In some embodiments, the term "adjacent", the term "proximate", or the like refers at least to a sufficient closeness between the objects defined as adjacent, proximate, or the like, to allow the objects to interact in a designated way. For example, if object A performs an action on an adjacent or proximate object B, objects A and B would have at least a sufficient closeness to allow object A to perform the action on object B. In this regard, some actions may require contact between the associated objects, such that if object A performs such an action on an adjacent or proximate object B, objects A and B would be in contact, for example, in some instances or embodiments where object A needs to be in contact with object B to successfully perform the action. In some embodiments, the term "adjacent", the term "proximate", or the like additionally or alternatively refers to objects that do not have another substantially similar object between them. For example, object A and object B could be considered adjacent or proximate if they contact each other (and, thus, it could be considered that no other object is between them), or if they do not contact each other but no other object that is substantially similar to object A, object B, or both objects A and B, depending on the embodiment, is between them. In some embodiments, the term "adjacent", the term "proximate", or the like additionally or alternatively refers to at least a sufficient closeness between the objects defined as adjacent, proximate, or the like, the sufficient closeness being within a range that does not place any one or more of the objects into a different or dissimilar region, or does not change an intended function of any one or more of the objects or of an encompassing object that includes a set of the objects. Different embodiments of the present invention adopt different ones or combinations of the above definitions. Of course, however, the term "adjacent", the term "proximate", or the like is not limited to any of the above example definitions, according to some embodiments. In addition, the term "adjacent" and the term "proximate" do not have the same definition, according to some embodiments.

The word "fluid" as used in this disclosure should be understood to include any fluid that can be contained within a bodily cavity or can flow into or out of, or both into and out of a bodily cavity via one or more bodily openings positioned in fluid communication with the bodily cavity. In some embodiments, the word "fluid" may include fluid that is not inherent to the bodily cavity, such as saline or other fluid that might artificially introduced into the bodily cavity. In the case of cardiac applications, fluid such as blood will flow into and out of various intra-cardiac cavities (e.g., a left atrium or right atrium).

The phrase "bodily opening" as used in this disclosure should be understood to include a naturally occurring bodily opening or channel or lumen; a bodily opening or channel or lumen formed by an instrument or tool using techniques that may include, but are not limited to, mechanical, thermal, electrical, chemical, and exposure or illumination techniques; a bodily opening or channel or lumen formed by trauma to a body; or various combinations of one or more of the above or other bodily openings. Various elements including respective openings, lumens or channels and positioned within the bodily opening (e.g., a catheter sheath) may be present in various embodiments. These elements may provide a passageway through a bodily opening for various devices employed in various embodiments.

The words "bodily cavity" as used in this disclosure should be understood to mean a cavity in a body. The bodily cavity may be a cavity provided in a bodily organ (e.g., an intra-cardiac cavity or chamber of a heart).

The word "tissue" as used in this disclosure may include non-fluidic tissue and fluidic tissue. Non-fluidic tissue generally (or predominantly) has solid-like properties, such as tissue that forms a surface of a body or a surface within a bodily cavity, a surface of an anatomical feature or a surface of a feature associated with a bodily opening positioned in fluid communication with the bodily cavity. Non-fluidic tissue can include part or all of a tissue wall or membrane that defines a surface of the bodily cavity. In this regard, the tissue can form an interior surface of the cavity that at least partially surrounds a fluid within the cavity. In the case of cardiac applications, non-fluidic tissue can include tissue used to form an interior surface of an intra-cardiac cavity such as a left atrium or right atrium. Fluidic tissue, on the other hand, generally (or predominantly) has fluid-like properties (as compared to solid-like properties). An example of fluidic tissue is blood. In this regard, it should be noted that fluidic tissue can have some solid-like component(s) (e.g., fluidic tissue may include solid-like components), and non-fluidic tissue can have some fluid-like component(s) (e.g., non-fluidic tissue may include fluidic tissue within it). Unless otherwise explicitly noted or required by context, the word "tissue" should include non-fluidic tissue and fluidic tissue. However, some contexts where the word "tissue" would not include fluidic tissue are when tissue ablation is discussed, and ablation of fluidic tissue could be undesired. In various embodiments, non-fluidic tissue does not include excised tissue.

The word "ablation" as used in this disclosure should be understood to include any disruption to certain properties of tissue. Most commonly, the disruption is to the electrical conductivity of tissue and may be achieved by heating, which may be generated with resistive or radio-frequency (RF) techniques for example. Other properties of tissue, such as mechanical or chemical, and other means of disruption, such as optical and electroporation are included when the term "ablation" is used. In some embodiments, ablative power levels may be within the range of 3 W to 5 W (as compared, e.g., to a non-tissue-ablative power level range of 50 mW to 60 mW that may be used for typical impedance determinations). In some embodiments, ratios of employed ablative power levels to employed non-tissue-ablative power levels (e.g., used for typical impedance determinations) may be: at least equal or greater than 50:1 in various embodiments; at least greater than 60:1 in some embodiments; at least greater than 80:1 in other various embodiments; and at least greater than 100:1 in yet other embodiments. In some embodiments, systems are configured to perform ablation of non-fluidic tissue while avoiding the delivery of excessive energy to fluidic tissue, because energy that is sufficient to ablate non-fluidic tissue may also impact fluidic tissue in some circumstances. For example, energy that is sufficient to ablate non-fluidic tissue, in some circumstances, may cause blood (an example of fluidic tissue) to coagulate. In these and other embodiments where ablative energy transferred to fluidic tissue is not desired, it should be understood that any statement or reference to the 'ablation of tissue' or the like in these contexts is intended to refer to ablation of non-fluidic tissue, as opposed to ablation of fluidic tissue. Techniques, according to some embodiments disclosed herein, facilitate the detection of conditions where energy that is intended to ablate non-fluidic tissue might unintentionally be delivered to fluidic tissue (e.g., blood) or another object.

The term "transducer" as used in this disclosure should be interpreted broadly as any device capable at least of distinguishing between fluid and non-fluidic tissue, sensing temperature, creating heat, ablating tissue, and measuring electrical activity of a tissue surface, stimulating tissue or any combination thereof. A transducer can convert input energy of one form into output energy of another form. Without limitation, a transducer may include an electrode, and references to a "transducer" herein may be replaced with "electrode" according to some embodiments. Without limitation, a transducer may include a resistive element, and references to a "transducer" herein may be replaced with "resistive element" according to some embodiments. Without limitation, a transducer may include an electrode, a resistive element, or a sensing device, or a combination of any two or all of an electrode, a resistive element, and a sensing device. An electrode or a resistive element, in some embodiments, may be configured at least as a sensing device. Because a transducer may include an electrode according to various embodiments, any reference herein to a transducer may also imply a reference to an electrode, or vice versa. A transducer may be constructed from several parts, which may be discrete components or may be integrally formed.

The term "activation" should be interpreted broadly as making active a particular function as related to various transducers such as those disclosed herein, for example. Particular functions may include, but are not limited to, tissue ablation, sensing electrophysiological activity, sensing temperature and sensing electrical characteristics (e.g., tissue impedance). For example, in some embodiments, activation of a tissue ablation function of a particular transducer is initiated by causing energy sufficient for tissue ablation to be delivered to the particular transducer from an energy source device system. In some embodiments, activation of a tissue ablation function of a particular electrode is initiated by causing energy from an energy source device system to be delivered to the particular electrode, the energy sufficient for tissue ablation. In some embodiments, activation of a tissue ablation function of a particular electrode is initiated by causing energy sufficient for tissue ablation to be transmitted by the particular electrode. Alternatively, in some embodiments, the activation may be deemed to be initiated when the particular transducer or particular electrode causes tissue that is to be ablated to reach or acquire a temperature sufficient for ablation of the tissue, which may be due to the energy provided by the energy source device system or due to the energy transmitted by the particular transducer or electrode. In some embodiments, the activation may last for a duration concluding when the ablation function is no longer active, such as when energy sufficient for the tissue ablation is no longer provided to, or transmitted by, the particular transducer or particular electrode. Alternatively, in some embodiments, the activation period may be deemed to be concluded when the tissue that is being ablated has a temperature below that sufficient for ablation of the tissue, which may be due to a reduction or cessation of the energy provided by the energy source device system or transmitted by the particular transducer or electrode. In some contexts, however, the word "activation" may merely refer to the initiation of the activating of a particular function, as opposed to referring to both the initiation of the activating of the particular function and the subsequent duration in which the particular function is active. In these contexts, the phrase or a phrase similar to "activation initiation" may be used. For example, in some embodiments, activation initiation may cause initiation of a transmission of energy (e.g., energy sufficient for tissue ablation) from a particular transducer or electrode.

The term "program" in this disclosure should be interpreted as a set of instructions or modules that can be executed by one or more components in a system, such as a controller system or data processing device system, in order to cause the system to perform one or more operations. The set of instructions or modules may be stored by any kind of memory device, such as those described subsequently with respect to the memory device system 130 shown in FIG. 1. In addition, it may be described that the instructions or modules of a program are configured to cause the performance of a function. The phrase "configured to" in this context is intended to include at least (a) instructions or modules that are presently in a form executable by one or more data processing devices to cause performance of the function (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the function (e.g., in the case where the instructions or modules are encrypted in a non-executable manner, but through performance of a decryption process, would be translated into a form ready for execution). The word "module" may be defined as a set of instructions.

Further, it is understood that information or data may be operated upon, manipulated, or converted into different forms as it moves through various devices or workflows. In this regard, unless otherwise explicitly noted or required by context, it is intended that any reference herein to information or data includes modifications to that information or data. For example, "data X" may be encrypted for transmission, and a reference to "data X" is intended to include both its encrypted and unencrypted forms. For another example, "image information Y" may undergo a noise filtering process, and a reference to "image information Y" is intended to include both the pre-processed form and the noise-filtered form. In other words, both the pre-processed form and the noise-filtered form are considered to be "image information Y". In order to stress this point, the phrase "or a derivative thereof" or the like may be used herein. Continuing the preceding example, the phrase "image information Y or a derivative thereof" refers to both the pre-processed form and the noise-filtered form of "image information Y", with the noise-filtered form potentially being considered a derivative of "image information Y". However, non-usage of the phrase "or a derivative thereof" or the like nonetheless includes derivatives or modifications of information or data just as usage of such a phrase does, as such a phrase, when used, is merely used for emphasis.

FIG. 1 schematically illustrates a system 100 according to some embodiments. In some embodiments, the system 100 may include a medical device system. System 100 is not limited to medical device systems, and may be another type of system, such as a system configured to deliver energy (e.g., tissue-ablative energy or energy sufficient to sense temperature or an electrical characteristic) to one or more resistive elements in a flexible printed circuit structure. In this regard, system 100 may include sensing or operative circuits where energy in the form of electric current is transmitted through the circuit(s) to measure or control various properties of connected components or the surrounding environment.

In some embodiments, the medical device system 100 includes a data processing device system 110, an input-output device system 120, and a processor-accessible memory device system 130. The processor-accessible memory device system 130 and the input-output device system 120 are communicatively connected to the data processing device system 110.

The data processing device system 110 includes one or more data processing devices that implement or execute, in conjunction with other devices, such as one or more of those in the system 100, one or more control programs associated with some of the various embodiments. Each of the phrases "data processing device", "data processor", "processor", and "computer" is intended to include any data processing device, such as a central processing unit ("CPU"), a desktop computer, a laptop computer, a mainframe computer, a tablet computer, a personal digital assistant, a cellular phone, and any other device configured to process data, manage data, or handle data, whether implemented with electrical, magnetic, optical, biological components, or other.

The memory device system 130 includes one or more processor-accessible memory devices configured to store information, including the information needed to execute the control programs associated with at least some of the various embodiments. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory device system and, consequently, may include one or more processor-accessible memory devices located within a single data processing device.

Each of the phrases "processor-accessible memory" and "processor-accessible memory device" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include a non-transitory computer-readable storage medium. In some embodiments, the memory device system 130 may be considered a non-transitory computer-readable storage medium system.

The phrase "communicatively connected" is intended to include any type of connection, whether wired or wireless, between devices, data processors, or programs in which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 may be implemented by a single application specific integrated circuit (ASIC) in some embodiments.

The input-output device system 120 may include a mouse, a keyboard, a touch screen, another computer, or any device or combination of devices from which a desired selection, desired information, instructions, or any other data is input to the data processing device system 110. The input-output device system 120 may include a user-activatable control system that is responsive to a user action, such as actions from a care provider such as a physician or technician. The input-output device system 120 may include any suitable interface for receiving information, instructions or any data from other devices and systems described in various ones of the embodiments. In this regard, the input-output device system 120 may include various ones of other systems described in various embodiments. For example, the input-output device system 120 may include at least a portion of a transducer-based device system or an electrode-based device system. The phrase "transducer-based device system" is intended to include one or more physical devices or systems that include various transducers. Similarly, the phrase "electrode-based device system" is intended to include one or more physical devices or systems that include various electrodes. In this regard, the phrases "transducer-based device system" and "electrode-based device system" may be used interchangeably in accordance with various embodiments. Similarly, the phrases "transducer-based device" and "electrode-based device" may be used interchangeably in accordance with various embodiments. In this regard, the phrases "transducer-based device system" and "electrode-based device system" may be used interchangeably with "resistive-element-based device system" in accordance with various embodiments. Similarly, the phrases "transducer-based device" and "electrode-based device" may be used interchangeably with "resistive element-based device" in accordance with various embodiments.

The input-output device system 120 also may include an image generating device system, a display device system, a speaker device system, a processor-accessible memory device system, or any device or combination of devices to which information, instructions, or any other data is output from the data processing device system 110. In this regard, if the input-output device system 120 includes a processor-accessible memory device, such memory device may or may not form part or all of the memory device system 130. The input-output device system 120 may include any suitable interface for outputting information, instructions or data to other devices and systems described in various ones of the embodiments. In this regard, the input-output device system may include various other devices or systems described in various embodiments.

Figure 2:
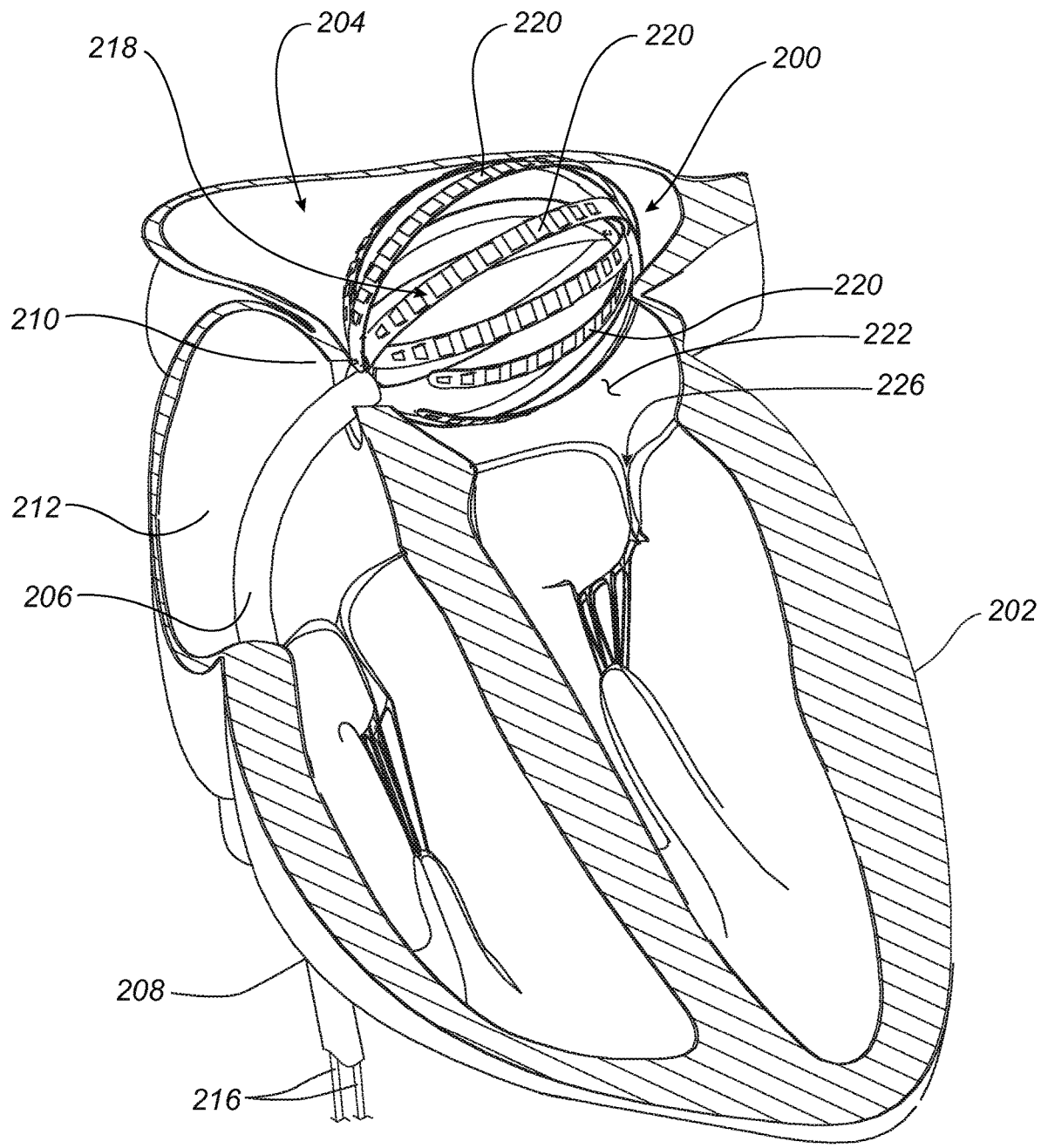
FIG. 2 is a cutaway diagram of a heart and a transducer-based device system percutaneously placed in a left atrium of the heart according to various example embodiments, the transducer-based device system optionally being part of the input-output device system of FIG. 1, according to some embodiments.

FIG. 2 shows a transducer-based device system 200, which may be included in the input-output device system 120 of FIG. 1, according to some embodiments. Because, as described in more detail below with respect to FIG. 4, electrodes or resistive elements may be part of transducers, according to some embodiments, the system 200 may also be considered an electrode-based device system or a resistive element-based device system in some embodiments. Such a system 200 may be useful for, among other things, investigating or treating a bodily organ, for example a heart 202, according to some example embodiments. The transducer-based device system 200 can be percutaneously or intravascularly inserted into a portion of the heart 202, such as an intra-cardiac cavity like left atrium 204. In this example, the transducer-based device system 200 includes a catheter 206 inserted via the inferior vena cava 208 and penetrating through a bodily opening in transatrial septum 210 from right atrium 212. In other embodiments, other paths may be taken.

Catheter 206 may include an elongated flexible rod or shaft member appropriately sized to be delivered percutaneously or intravascularly. Various portions of catheter 206 may be steerable. Catheter 206 may include one or more lumens. The lumen(s) may carry one or more communications or power paths, or both. For example, the lumens(s) may carry one or more electrical conductors 216 (two shown in this embodiment). Electrical conductors 216 provide electrical connections for system 200 that are accessible externally from a patient in which the transducer-based device system 200 is inserted.

In some embodiments, the electrical conductors 216 may provide electrical connections to transducers 220 (three called out in FIG. 2) that respectively include one or more electrodes, and optionally one or more other devices, (e.g., both discussed with respect to FIG. 4, below) configured to, among other things, provide stimulation (e.g., electrical stimulation that may include pinging or pacing) to tissue within a bodily cavity (e.g., left atrium 204), ablate tissue in a desired pattern within the bodily cavity, sense characteristics of tissue (e.g., electrophysiological activity, convective cooling, permittivity, force, temperature, impedance, thickness, or a combination thereof) within the bodily cavity, or a combination thereof. In some embodiments, the respective portions of transducers 220 may be connected in series through conductive elements (not shown in FIG. 2 but discussed with respect to FIG. 4, below) that facilitate multiplicity, redundancy, and failure tolerance in associated circuits of system 200.

The sensing of characteristics may, among other things, be configured to distinguish between fluid, such as fluidic tissue (e.g., blood), and non-fluidic tissue forming an interior surface of a bodily cavity (e.g., left atrium 204), may be configured to map the cavity, for example, using positions of openings or ports into and out of the cavity to determine a position or orientation (e.g., pose), or both of a portion of the device system 200 in the bodily cavity, may be configured to indicate whether an ablation has been successful; or a combination thereof.

Transducer-based device system 200 may include a frame or structure 218 which assumes an unexpanded or delivery configuration (e.g., FIG. 3A, discussed below) for delivery to left atrium 204. Structure 218 is deployable or expandable (i.e., shown in a deployed or expanded configuration in FIG. 2,) upon delivery to left atrium 204. Another embodiment of a deployed or expanded configuration is also shown in FIG. 3B, which is discussed below. In this regard, in some embodiments, the transducer-based device system 200 is moveable between a delivery or unexpanded configuration (e.g., similar to FIG. 3A, discussed below) in which a portion (e.g., the structure 218) of the device system 200 is sized for passage through a bodily opening leading to a bodily cavity, and a deployed or expanded configuration (e.g., FIG. 2,) in which the portion of the device system 200 has a size too large for passage through the bodily opening leading to the bodily cavity. An example of an expanded or deployed configuration is when the portion of the transducer-based device system is in its intended-deployed-operational state inside the bodily cavity. Another example of the expanded or deployed configuration is when the portion of the transducer-based device system is being changed from the delivery configuration to the intended-deployed-operational state to a point where the portion of the device system now has a size too large for passage through the bodily opening leading to the bodily cavity. Further, in some embodiments, when the portion (e.g., the structure 218) is in the expanded or deployed configuration in the left atrium 204, various ones of a plurality of transducers 220 are positioned proximate the interior surface formed by non-fluidic tissue 222 of left atrium 204. In some embodiments, when the portion (e.g., the structure 218) is in the expanded or deployed configuration in the left atrium 204, various ones of a plurality of transducers 220 are positioned such that a physical portion of each of the various ones of the transducers 220 is configured to contact the interior surface formed by non-fluidic tissue 222 of left atrium 204. In some embodiments, at least some of the transducers 220 are configured to sense a physical characteristic of a fluid (i.e., blood), non-fluidic tissue 222 (i.e., cardiac wall tissue), or both, that may be used to determine a position or orientation (i.e., pose), or both, of a portion of a device system 200 within, or with respect to left atrium 204. For example, transducers 220 may be configured to determine a location of pulmonary vein ostia or a mitral valve 226, or both. In some embodiments, at least some of the transducers 220 may be controlled to selectively ablate portions of the non-fluidic tissue 222. For example, some of the transducers 220 may be controlled to ablate a pattern or path around various ones of the bodily openings, ports or pulmonary vein ostia, for instance, to reduce or eliminate the occurrence of atrial fibrillation. Each of various ones of the transducers 220 may include an electrode in various embodiments, as described below with respect to FIG. 4, for example. Each of various ones of the transducers 220 may include resistive element in various embodiments, as described below with respect to FIG. 4, for example.

Figure 3A:
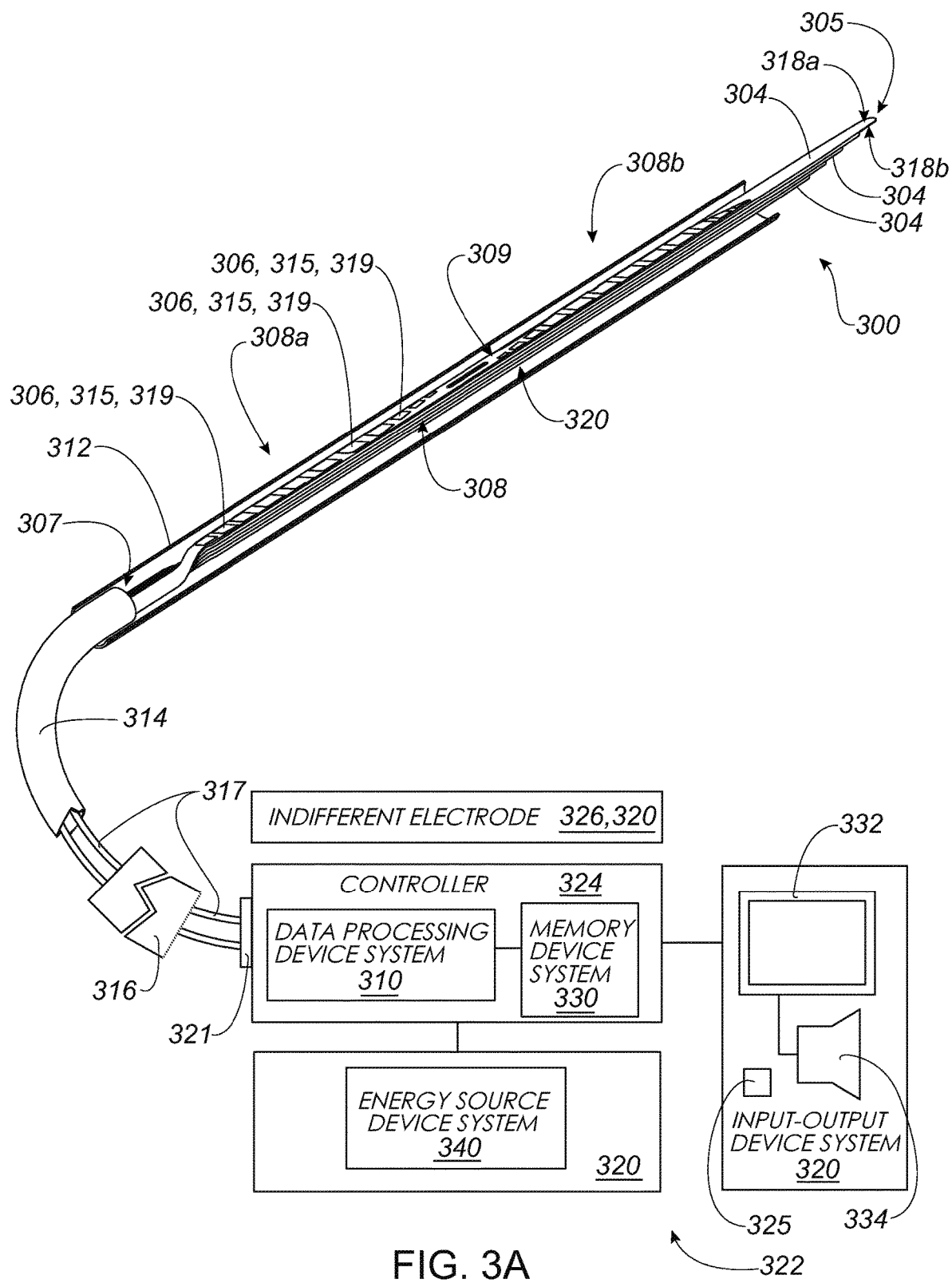
FIG. 3A is a partially schematic representation of a medical device system, which may represent one or more implementations of the medical device system of FIG. 1 in which an expandable structure of a transducer-based device system is in a delivery or unexpanded configuration, according to various example embodiments.
Figure 3B:
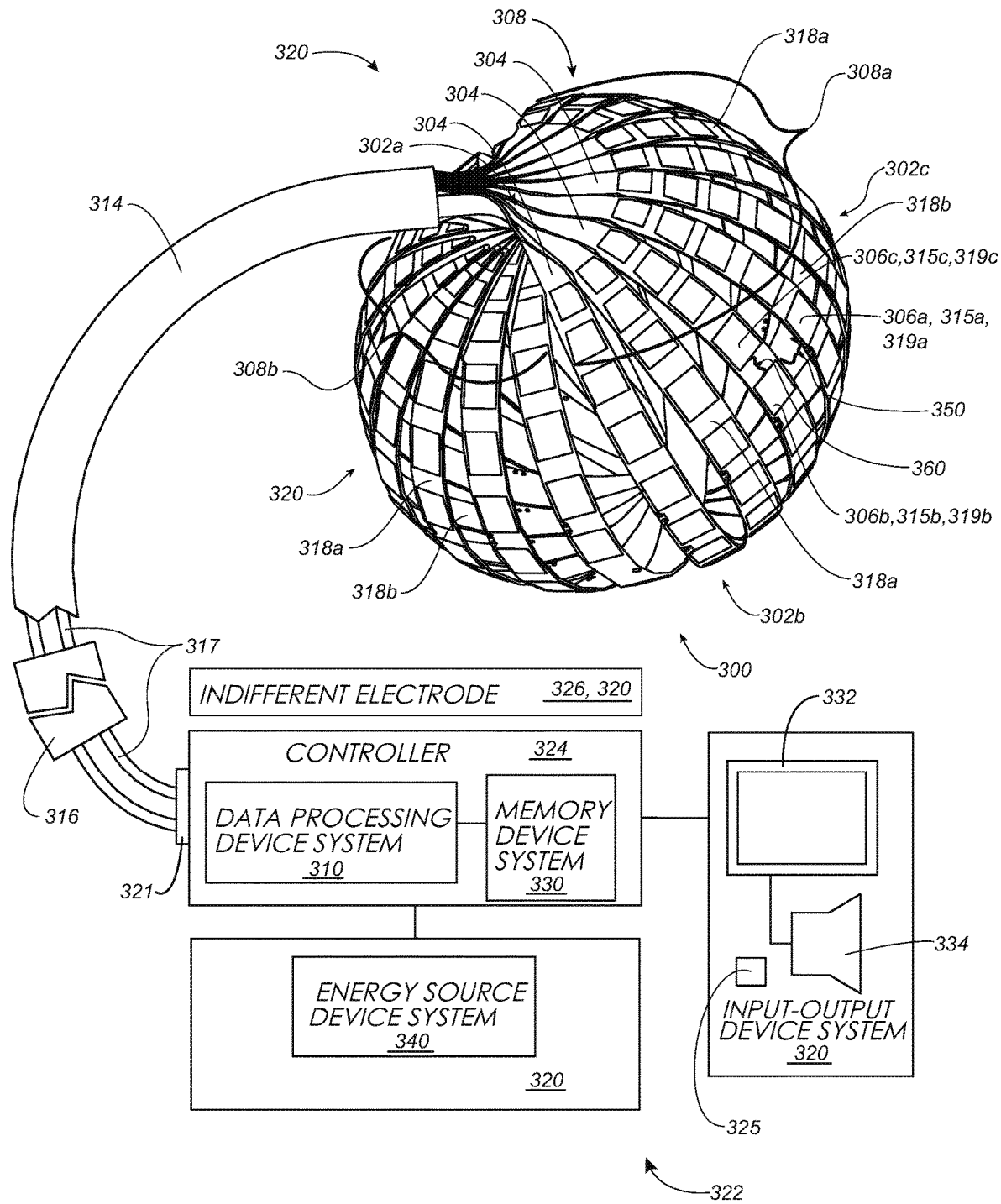
FIG. 3B is the representation of the medical device system of FIG. 3A with the expandable structure shown in a deployed or expanded configuration, according to some embodiments.

Each of FIGS. 3A and 3B is a partially schematic representation of a medical device system, which may represent one or more implementations of the medical device system 100 of FIG. 1, according to some embodiments. In this regard, the medical device system in each of FIGS. 3A and 3B may be configured to deliver energy to one or more resistive elements, such as a transducer or electrode. Each of the medical device systems of FIGS. 3A and 3B includes a transducer-based device system 300. The transducer-based device system 300 may include several hundreds of electrodes 315, but need not include that many. FIG. 3A illustrates the transducer-based device system 300 in the delivery or unexpanded configuration, according to various example embodiments, and FIG. 3B illustrates the transducer-based device system 300 in the deployed or expanded configuration, according to some embodiments.

In this regard, the transducer-based device system 300 includes a plurality of elongate members 304 (three called out in each of FIGS. 3A and 3B) and a plurality of transducers 306 (three called out in FIG. 3A and three called out in FIG. 3B as 306a, 306b and 306c). In some embodiments, the transducers 306 have the configuration of the transducers 220 in FIG. 2. In some embodiments, the transducers 306 are formed as part of, or are located on, the elongate members 304. In some embodiments, the elongate members 304 are arranged as a frame or structure 308 that is selectively movable between an unexpanded or delivery configuration (e.g., as shown in FIG. 3A) and an expanded or deployed configuration (e.g., as shown in FIG. 3B) that may be used to position elongate members 304 or various one of the transducers 306 against a tissue surface within the bodily cavity or position the elongate members 304 in the vicinity of, or in contact with, the tissue surface.

In some embodiments, the structure 308 has a size in the unexpanded or delivery configuration suitable for percutaneous delivery through a bodily opening (e.g., via catheter sheath 312, not shown in FIG. 3B) to the bodily cavity. In some embodiments, structure 308 has a size in the expanded or deployed configuration too large for percutaneous delivery through a bodily opening (e.g., via catheter sheath 312) to the bodily cavity. The elongate members 304 may form part of a flexible circuit structure (i.e., also known as a flexible printed circuit board (PCB)). The elongate members 304 may include a plurality of different material layers, and each of the elongate members 304 may include a plurality of different material layers. The structure 308 may include a shape memory material, for instance Nitinol. The structure 308 may include a metallic material, for instance stainless steel, or non-metallic material, for instance polyimide, or both a metallic and non-metallic material by way of non-limiting example. The incorporation of a specific material into structure 308 may be motivated by various factors including the specific requirements of each of the unexpanded or delivery configuration and expanded or deployed configuration, the required position or orientation (i.e., pose) or both of structure 308 in the bodily cavity, or the requirements for successful ablation of a desired pattern.

The plurality of transducers 306 are positionable within a bodily cavity, for example, by positioning of the structure 308. For instance, in some embodiments, the transducers 306 are able to be positioned in a bodily cavity by movement into, within, or into and within the bodily cavity, with or without a change in a configuration of the plurality of transducers 306 (e.g., a change in a configuration of the structure 308 causes a change in a configuration of the transducers 306 in some embodiments). In some embodiments, the plurality of transducers 306 are arrangeable to form a two- or three-dimensional distribution, grid or array capable of mapping, ablating or stimulating an inside surface of a bodily cavity or lumen without requiring mechanical scanning. As shown, for example, in FIG. 3A, the plurality of transducers 306 are arranged in a distribution receivable in a bodily cavity (not shown in FIG. 3A). As shown, for example, in FIG. 3A, the plurality of transducers 306 are arranged in a distribution suitable for delivery to a bodily cavity.

Figure 4:
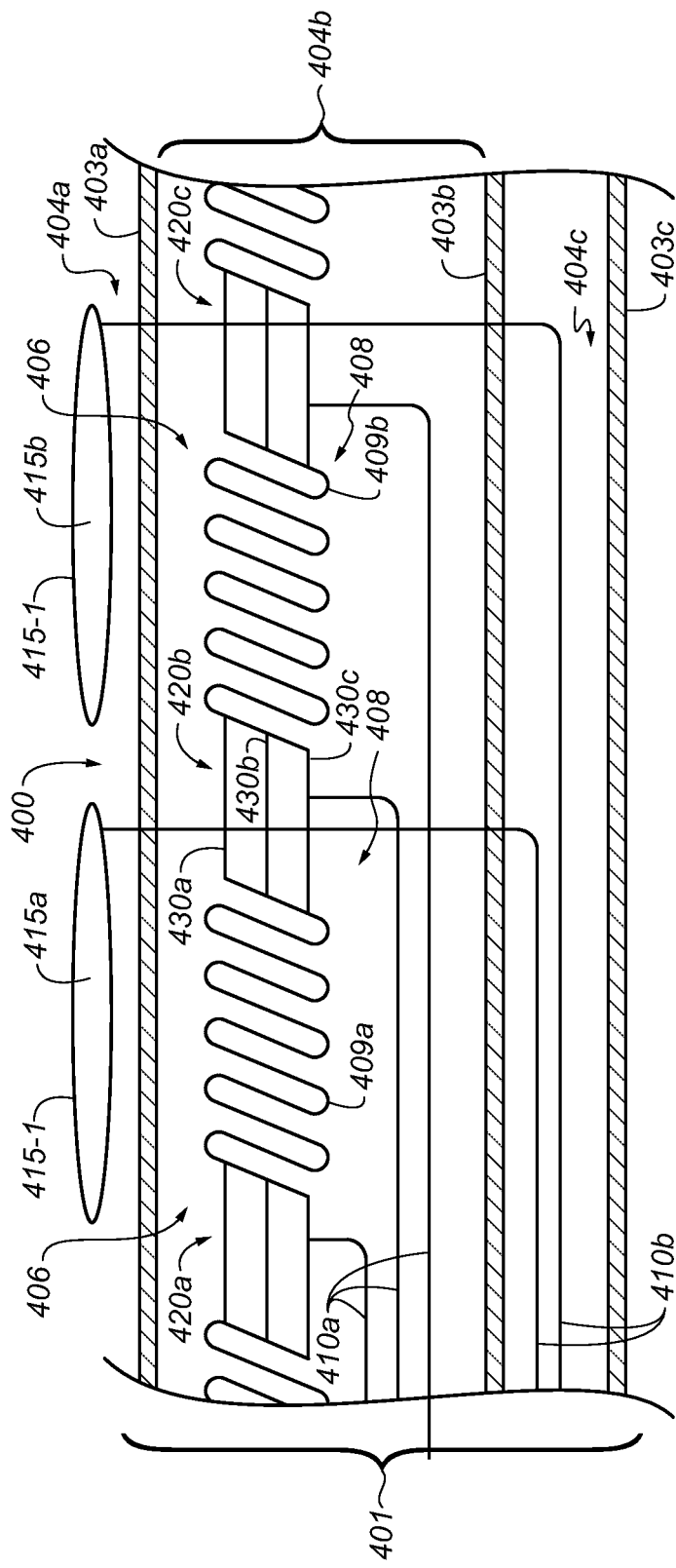
FIG. 4 is a schematic representation of a transducer-based device that includes a flexible circuit structure, according to various example embodiments.

FIG. 4 is a schematic representation of at least a portion of a transducer-based device system 400 that includes a flexible circuit structure 401 that is employed to provide a plurality of transducers 406 (two called out) according to various example embodiments. In some embodiments, the transducer-based device system 400 corresponds to at least part of the transducer-based device system 300 and transducers 406 correspond to the transducers 306. In some embodiments, the transducer-based device system 400 corresponds to at least part of the transducer-based device system 200 and transducers 406 correspond to the transducers 220. In some embodiments, the flexible circuit structure 401 may form part of a structure (e.g., structure 308) that is selectively movable between a delivery configuration sized for percutaneous delivery and an expanded or deployed configuration sized too large for percutaneous delivery. In some embodiments, the flexible circuit structure 401 may be located on, or form at least part of, a structural component (e.g., elongate member 304) of a transducer-based device system (e.g., transducer-based device system 200, 300, 400). In some embodiments, the flexible circuit structure 401 is provided on a non-expandable surface of a catheter, the non-expandable portion configured to not be selectively expandable between two states (e.g., a delivery configuration and a deployed configuration as exemplified in FIGS. 3A and 3B). In some embodiments, the flexible circuit structure may be located on a surface of an elongate shaft of a catheter.

The flexible circuit structure 401 may be formed by various techniques including flexible printed circuit techniques. In some embodiments, the flexible circuit structure 401 includes various conductive and nonconductive flexible layers. One or more of the nonconductive flexible layers 403 (three called out in FIG. 4 as reference symbols 403a, 403b and 403c) may form a substrate for the flexible circuit structure and may be interleaved with one or more of the conductive layers 404 to electrically or physically separate one or more conductive layers from other conductive layers. In some embodiments, each of the nonconductive flexible layers 403 includes an electrical insulator material (e.g., polyimide). One or more of the nonconductive flexible layers 403 may include a different material than another of the nonconductive flexible layers 403 in some embodiments. One or more of the electrically conductive layers 404 (three called out in FIG. 4 as reference symbols 404a, 404b and 404c) may be patterned to form various electrically conductive elements. For example, electrically conductive layer 404a may be patterned to form a respective electrode 415 (e.g., electrode 415a, 415b) included as part of each of the transducers 406. Electrodes 415 may have respective electrode edges 415-1 that form a periphery of an electrically conductive surface or surface portion associated with the respective electrode 415.

In some embodiments, the respective electrically conductive surface or surface portion of one or more of the electrodes 415 is configured to transmit energy to contacting tissue at a level sufficient for ablation of the tissue. Other energy levels may be transmitted to, for example, provide stimulation (e.g., electrical stimulation that may include pinging or pacing) to tissue within a bodily cavity (e.g., left atrium 204), sense characteristics of tissue (e.g., electrophysiological activity, convective cooling, permittivity, force, temperature, impedance, tissue thickness, or a combination thereof) within the bodily cavity, or a combination thereof.

Electrically conductive layer 404b may be patterned, in some embodiments, to form respective temperature sensors 408 (e.g., resistive temperature detectors) for each of the transducers 406 as well as various leads 410a arranged to measure respective voltage associated with each of the temperature sensors 408. In some embodiments, each temperature sensor 408 includes an electrical load such as a patterned resistive element 409 (two called out in FIG. 4 as reference symbols 409a and 409b) having a predetermined electrical resistance. In some embodiments, each resistive element 409 includes a metal having relatively high electrical conductivity (e.g., copper). In some embodiments, the resistive element 409 has a serpentine form. The serpentine form has the advantage of providing an increase in the overall resistance of resistive element 409 by increasing its overall length while maintaining a compact spatial arrangement. In some embodiments, each resistive element 409 is connected to an adjacent resistive element 409 by a conductive element, such as a conductive mesh 420. The conductive mesh 420 provides multiple, redundant, and failure tolerant electrical connections between adjacent pairs of resistive elements 409, thereby increasing the robustness and durability of the flexible circuit structure 401. It should be noted that, although conductive meshes 420 (also referred to herein as "meshes") are provided as examples of conductive elements that couple adjacent resistive elements in a circuit, such conductive elements may be provided by other structures providing multiple, redundant, and failure tolerant electrical connections between adjacent pairs of resistive elements 409 and need not have the equal conductive segment (e.g., 430a, 430b, 430c) spacing illustrated, although such a spacing may be beneficial in some embodiments. Each of the electrodes 415 may overlap, or partially overlap a respective resistive element 409. As discussed previously, the electrodes 415 may be stiffer than other portions of the flexible circuit structure 401. This higher stiffness may increase a likelihood of the occurrence of cracks in regions at least proximate the electrode edge 415-1 portions. In some embodiments, the likelihood of open or otherwise impaired circuits due to cracks is reduced by the multiple, redundant, and failure tolerant connections provided by the conductive meshes 420.

In some embodiments, electrically conductive layer 404c may be patterned to provide portions of various connection leads 410b arranged to provide an electrical communication path to electrodes 415. In some embodiments, leads 410b are arranged to pass though vias (accounted for in FIG. 4, e.g., by the upward (with respect to the proper orientation of FIG. 4) movement of the leads 410b) in flexible layers 403a and 403b to connect with electrodes 415. Although FIG. 4 shows flexible layer 403c as being a bottom-most layer, some embodiments may include one or more additional layers underneath flexible layer 403c, for example, one or more structural layers, such as a stainless steel or composite layer. These one or more structural layers, in some embodiments, are part of the flexible circuit structure 401 and may be part of, e.g., elongate member 304. In some embodiments, the flexible circuit structure 401 includes a nonconductive substrate including at least one flexible layer. In addition, although FIG. 4 shows only three flexible layers 403a-403c and only three electrically conductive layers 404a-404c, it should be noted that other numbers of flexible layers, other numbers of electrically conductive layers, or both, may be included. It should be noted that the various structures of the flexible circuit system, such as the electrode 415, resistive element 409, or conductive mesh 420, for example, may include different metals or conductive materials according to some embodiments.

In FIG. 4, three conductive meshes 420a, 420b and 420c are shown. It is understood that additional resistive elements 409 and conductive meshes 420 may be present in various example embodiments. It is noted that various elements such as electrodes 415, resistive elements 409 and conductive meshes 420 are schematically represented in various orientations that are convenient for the sake of clarity in FIG. 4, and that at least some of these orientations may be different from one another. It is also noted that various elements are not shown to scale. For example, according to some embodiments, while layers 403a, 403b and 403c may be considered to be depicted by side elevation views of the layers on FIG. 4, electrodes 415, resistive elements 409 and conductive meshes 420 may be considered to be depicted by perspective or plan views of the particular layers they are formed from. It is understood that these different orientations are provided to facilitate the discussion of these various elements and do not impose a limitation on the spatial or structural arrangements.

In some embodiments, at least a portion of the conductive mesh 420 may spatially overlap at least a portion of an electrode 415 or may be spatially overlapped by at least a portion of an electrode 415 (e.g., depending on the viewing direction). In FIG. 4, at least a portion of the conductive mesh 420b is arranged to overlap, or be overlapped by (e.g., depending on the viewing direction), at least a portion of the electrode 415a as shown by the location of the electrode edge 415-1. For example, the conductive mesh 420 may be patterned in the electrically conductive layer 404b and the electrode 415a may be patterned in the electrically conductive layer 404a, the electrically conductive layers 404a and 404b arranged in an overlapping configuration or arrangement. The electrode 415a and the conductive mesh 420b are arranged so that they share an overlapped portion. In some embodiments, at least a respective portion of the conductive mesh 420b may spatially overlap respective portions of each of at least two of the electrodes 415 or may be spatially overlapped by respective portions of each of at least two of the electrodes 415. For example, at least a portion of conductive mesh 420b connected to the resistive element 409a is overlapped, or overlaps (e.g., depending on the viewing direction) a respective portion of the electrode 415a and at least a portion of the conductive mesh 420b connected to the resistive element 409b is overlapped, or overlaps (e.g., depending on the viewing direction) a respective portion of the electrode 415b in FIG. 4. This arrangement positions the connection regions between the conductive mesh 420b and resistive elements 409a and 409b away from the electrode edges 415-1 of electrodes 415a and 415b. During bending of the flexible circuit structure, the edges 415-1 of the relatively stiffer electrodes 415a and 415b can concentrate bending stresses applied to conductive mesh 420b to create a stress riser adjacent the electrode edge. By moving the connection regions between the conductive mesh 420b and the resistive elements 409a, 409b away from regions proximate the electrode edges 415-1, any potential stress risers associated with the connection regions are not readily combined with the stress riser associated with the electrode edge 415-1 and thereby, occurrences of combined stress concentration effects that can more easily lead to the formation of stress cracks during bending or flexing may be reduced.

In some embodiments, the flexible circuit structure 401 may include at least one electrically nonconductive flexible layer 403 (electrically nonconductive substrate), at least one electrically conductive flexible circuit layer 404 coupled, directly or indirectly, to the at least one electrically nonconductive flexible layer 403. In some embodiments, the electrically conductive flexible circuit layer 404 may include conductive patterns including a plurality of resistive elements 409 and a plurality of conductive meshes 420. Each conductive mesh 420 of the plurality of conductive meshes electrically connects at least a respective adjacent pair of resistive elements 409 of the plurality of resistive elements 409 according to various embodiments. Each conductive mesh 420 of the plurality of conductive meshes directly connects at least to each of a respective adjacent pair of resistive elements 409 of the plurality of resistive elements 409 according to various embodiments.

In some embodiments, the plurality of conductive meshes 420 serially electrically connects the plurality of resistive elements 409 to provide at least one electric current flow path through the plurality of resistive elements 409. Electric current flows through each of the resistive elements 409 and each of the conductive meshes 420, along electrical pathways providing at least one electric current flow path, according to various embodiments. In some embodiments, the conductive meshes 420 provide multiple electrical pathways for the electric current to pass through all of the resistive elements 409. In this regard, the phrase "electrical pathway" refers to at least one structural element such as a trace of conductive material (for example, resistive element 409 or conductive segment 430 discussed in more detail below) and the phrase "electric current flow path" refers to a sequential set of one or more electrical pathways through which electric current flows or is able to flow in the broader circuit at any given time, according to some embodiments. For example, assume that conductive segment 430b in FIG. 4 is split in the middle (not shown in FIG. 4, such split is merely being assumed for this example) causing an open circuit in conductive segment 430b. The split-created halves of conductive segment 430b may each be deemed an electrical pathway, because each half comprises a trace of conductive material, but the split-created two halves of conductive segment 430b would not provide an electric current flow path between resistive elements 409a and 409b, because, in the context of the larger circuit providing the structure of FIG. 4, electric current is not able to flow between resistive elements 409a and 409b via the conductive segment 430b, because an open circuit exists in the conductive segment 430b in this example. On the other hand, if the conductive segment 430b is in proper working order as shown in FIG. 4, such conductive segment 430b may be considered an electrical pathway and may also be considered to provide an electric current flow path between resistive elements 409a and 409b.

In this regard, an electrical pathway may be provided by a plurality of electrically connected traces, such as a plurality of electrically connected conductive segments 430. In this regard, an electrical pathway may be provided by a sequential grouping of all of the conductive traces associated with any particular electric current flow path, or a sequential grouping of some of the conductive traces associated with a particular portion of the particular electric current flow path. In some embodiments, there may be more than one electric current flow path (e.g., between resistive elements or other circuit structures), with varying amounts of electric current flowing through each of the electric current flow paths.

It should be noted that a single conductive element (such as a single conductive segment 430, like conductive element 430a) having a cross-sectional area could be considered as providing multiple virtual electrical pathways or electric current flow paths through the connections between particles of conductive material that form the single conductive element. For this disclosure, however, it is considered that a single conductive element (such as a single conductive element 430, like conductive element 430a) provides all or a portion of a single electrical pathway, although the portion of the single electrical pathway may be included as part of other electrical pathways formed by connections to other conductive elements (traces of conductive particles). For example, each particular conductive segment 430 defines a respective, single, electrical pathway, but may also be part of multiple, longer, electrical pathways that include the particular conductive segment 430. Similarly, an electrical pathway may be included in multiple, different electric current flow paths.

In some embodiments, electric current flows through each of the resistive elements 409 and each of the conductive meshes 420, which are arranged such that at least one conductive mesh 420 is located between each pair of resistive elements 409 that are successively arranged in series along the electric current flow path.

In some embodiments, the flexible circuit structure 401 is electrically connected to a voltage or current measurement system (e.g., provided at least in part by (a) input-output device system 120, 320, (b) data processing device system 110, 310, or both (a) and (b), such as that described with respect to FIG. 16, below, according to some embodiments) by the plurality of measurement leads 410a. In some embodiments, respective pairs of measurement leads 410a are arranged to sense voltage or current across each resistive element 409. In some embodiments, at least some of the measurement leads 410a are electrically connected to a respective conductive mesh 420. In some embodiments, voltage measurement leads 410a are arranged to allow for a sampling of electrical voltage between each resistive element 409. These arrangements allow for the electrical resistance of each resistive element 409 to be accurately determined. The ability to accurately determine the electrical resistance of each resistive element 409 may be motivated by various reasons including determining temperature values at locations at least proximate the resistive element 409 based at least on changes in the resistance caused by convective cooling effects (e.g., as provided by blood flow).

In some embodiments, electrodes 415 are employed to selectively deliver RF energy to various tissue structures within a bodily cavity (e.g., a tissue cavity such as an intra-cardiac cavity). The energy delivered to the tissue structures may be sufficient for ablating portions of the tissue structures. In various embodiments, the tissue structures are typically formed from non-fluidic tissue and the energy sufficient for ablating portions of the tissue structures is typically referred to as sufficient for tissue ablation. It is noted that energy sufficient for non-fluidic-tissue ablation may include energy levels sufficient to disrupt or alter fluidic tissue (e.g., blood) that may, for example, be located proximate the tissue structure. In many cases, the application of non-fluidic-tissue-ablative energy (i.e., energy that is sufficient to ablate non-fluidic tissue) to fluidic tissue, such as blood, is undesired when the energy is sufficient to disrupt or adversely impact a property of the fluidic tissue. For example, the application of non-fluidic-tissue-ablative energy to blood may be undesired when the energy is sufficient to cause various parts of the blood to coagulate in a process typically referred to as thermal coagulation. In this regard, some embodiments facilitate detection of conditions where an electrode configured to deliver non-fluidic-tissueablative energy may be in a configuration where it is not able to properly transmit such energy. In some embodiments, a detection of such a condition results in an error notification being transmitted or otherwise presented to a user (e.g., via input-output device system 120, 320) or, in some embodiments, a restricting of that electrode from transmitting at least a portion of the non-fluidic-tissue-ablative energy (e.g., via control of energy source device system 340 (discussed below) via controller 324).

In some embodiments, each resistive element 409 is positioned adjacent a respective one of the electrodes 415. Each resistive element 409 may or may not be in contact with the respective one of the electrodes 415, but may be in sufficient proximity to the respective one of the electrodes 415 to interact with or be influenced by tissue in proximity to the respective one of the electrodes 415. In some embodiments, each of the resistive elements 409 is positioned in a stacked or layered array with a respective one of the electrodes 415 to form a respective one of the transducers 406.

FIG. 4 shows an example embodiment of a conductive mesh 420b including conductive segments 430 (three called out in FIG. 4 as reference symbols 430a, 430b, and 430c). Each conductive segment 430 provides one of a plurality of electrical pathways for flow of electric current, according to some embodiments. Each of the plurality of electrical pathways provides a portion of an electric current flow path through the serially connected resistive elements 409 and conductive meshes 420. In some embodiments, the plurality of conductive segments 430 provides a plurality of electrical pathways. Although conductive mesh 420b is shown with three conductive segments 430 in FIG. 4 (i.e., 430a, 430b and 430c), more or fewer number of conductive segments may be provided in various embodiments. According to various embodiments, the conductive mesh 420b provides multiple or redundant or failure tolerant electrical pathways so that an electric current flow path through the resistive elements 409 and conductive meshes 420 may be maintained even if one or more of the electrical pathways (e.g., one or more of the conductive segments 430a, 430b, 430c, in some embodiments) is interrupted or broken due to cracks or other defects. In some embodiments, respective ones of the leads 410a are connected to respective ones of the conductive meshes 420 at more than one connection point, providing further multiplicity, redundancy, and failure tolerance in the circuit and robustness in the presence of cracks or other impediments to current flow.

In some embodiments in which the transducer-based device system 200 or 300 is deployed in a bodily cavity (e.g., when the transducer-based device system 200 or 300 takes the form of a catheter device system arranged to be percutaneously or intravascularly delivered (or through a natural bodily opening) to a bodily cavity), it may be desirable to perform various mapping procedures in the bodily cavity (e.g., operating the transducer-based device system 200 or 300 in a mapping mode). For example, when the bodily cavity is an intra-cardiac cavity, a desired mapping procedure may include mapping electrophysiological activity in the intra-cardiac cavity. Other desired mapping procedures may include mapping of various anatomical features within a bodily cavity. An example of the mapping performed by devices according to various embodiments may include locating the position of the ports of various bodily openings positioned in fluid communication with a bodily cavity. For example, in some embodiments, it may be desired to determine the locations of various ones of the pulmonary veins or the mitral valve that each interrupts an interior surface of an intra-cardiac cavity such as a left atrium.

In some example embodiments, the mapping is based at least on locating bodily openings by differentiating between fluid and non-fluidic tissue (e.g., tissue defining a surface of a bodily cavity). There are many ways to differentiate non-fluidic tissue from a fluid such as blood or to differentiate tissue from a bodily opening in case a fluid is not present. Four approaches may include by way of non-limiting example, and, depending upon the particular approach(es) chosen, the configuration transducers 406 in FIG. 4 may be implemented accordingly:

1. The use of convective cooling of heated transducer elements by fluid. When operated in a flow sensing mode, an arrangement of slightly heated transducer elements that is positioned adjacent to the tissue that forms the interior surface(s) of a bodily cavity and across the ports of the bodily cavity will be cooler at the areas which are spanning the ports carrying the flow of fluid.

2. The use of tissue impedance measurements. A set of transducers positioned adjacently to tissue that forms the interior surface(s) of a bodily cavity and across the ports of the bodily cavity can be responsive to electrical tissue impedance. Typically, heart tissue will have higher associated tissue impedance values than the impedance values associated with blood.

3. The use of the differing change in dielectric constant as a function of frequency between blood and tissue. A set of transducers positioned around the tissue that forms the interior surface(s) of the atrium and across the ports of the atrium monitors the ratio of the dielectric constant from 1 kHz to 100 kHz. Such may be used to determine which of those transducers are not proximate to tissue, which is indicative of the locations of the ports.

4. The use of transducers that sense force (i.e., force sensors). A set of force detection transducers positioned around the tissue that forms the interior surface(s) of a bodily cavity and across the bodily openings or ports of the bodily cavity may be used to determine which of the transducers are not engaged with the tissue, which may be indicative of the locations of the ports.

Various ones of the above approaches may be used, at least in part, to determine proximity of a transducer to non-fluidic tissue or to fluidic tissue in some embodiments.

Various ones of the above approaches may be used, at least in part, to determine contact between a transducer and non-fluidic tissue or contact between a transducer and fluidic tissue in some embodiments. Various ones of the above approaches may be used, at least in part, to determine an amount of an electrically conductive surface portion of an electrode that contacts non-fluidic tissue or contacts fluidic tissue in some embodiments. Various ones of the above approaches may be used, at least in part, to determine an amount of an electrically conductive surface portion of an electrode that is available to contact non-fluidic tissue or available to contact fluidic tissue in some embodiments.

Referring again to the medical device systems of FIGS. 3A and 3B, according to some embodiments, transducer-based device system 300 communicates with, receives power from or is controlled by a transducer-activation system 322, which may include a controller 324 and an energy source device system 340. In some embodiments, the controller 324 includes a data processing device system 310 and a memory device system 330 that stores data and instructions that are executable by the data processing device system 310 to process information received from other components of the medical device system of FIGS. 3A and 3B or to control operation of components of the medical device system of FIGS. 3A and 3B, for example by activating various selected transducers 306 to ablate tissue, sense tissue characteristics, et cetera. In this regard, the data processing device system 310 may correspond to at least part of the data processing device system 110 in FIG. 1, according to some embodiments, and the memory device system 330 may correspond to at least part of the memory device system 130 in FIG. 1, according to some embodiments. The energy source device system 340, in some embodiments, is part of an input-output device system 320, which may correspond to at least part of the input-output device system 120 in FIG. 1. Although only a single controller 324 is illustrated, it should be noted that such controller 324 may be implemented by a plurality of controllers. In some embodiments, the transducer-based device system 300 (or 200 in FIG. 2) is considered to be part of the input-output device system 320. The input-output device system 320 may also include a display device system 332, a speaker device system 334, or any other device such as those described above with respect to the input-output device system 120.

In some embodiments, elongate members 304 may form a portion or an extension of control leads 317 that reside, at least in part, in an elongated cable 316 and, at least in part, in a flexible catheter body 314. The control leads terminate at a connector 321 or other interface with the transducer-activation system 322 and provide communication pathways between at least the transducers 306 and the controller 324. The control leads 317 may correspond to electrical conductors 216 in some embodiments.

As discussed with respect to FIG. 4, each of various ones of the transducers 306, 406 includes an electrode 315, 415, according to some embodiments. In these various embodiments, each of at least some of the electrodes 315, 415 may include a respective energy transmission surface (e.g., energy transmission surface 319 in FIG. 3A) configured to transfer, transmit, or deliver energy, for example, to tissue. In some embodiments, at least some of the respective energy transmission surfaces are configured to receive energy, for example, from tissue. Each of the energy transmission surfaces may be bounded by a respective electrode edge 415-1 (e.g., FIG. 4).

In some embodiments, input-output device system 320 may include a sensing device system 325 configured to detect various characteristics or conditions including, but not limited to, at least one of tissue characteristics (e.g., electrical characteristics such as tissue impedance, tissue type, tissue thickness) and thermal characteristics such as temperature. Various other particular conditions described later in this disclosure may be detected by sensing device system 325 according to various embodiments. It is noted that in some embodiments, sensing device system 325 includes various sensing devices or transducers configured to sense or detect a particular condition while positioned within a bodily cavity. In some embodiments, at least part of the sensing device system 325 may be provided by transducer-based device system 300 (e.g., various ones of transducers 306). In some embodiments, sensing device system 325 includes various sensing devices or transducers configured to sense or detect a particular condition while positioned outside a given bodily cavity or even outside a body that includes the bodily cavity. In some embodiments, the sensing device system 325 may include an ultrasound device system or a fluoroscopy device system or portions thereof by way of non-limiting example.

The energy source device system 340 may, for example, be connected to various selected transducers 306 or their respective electrodes 315 to provide energy in the form of electric current or energy (e.g., RF energy) to the various selected transducers 306 or their respective electrodes 315 to cause ablation of tissue. In this regard, although FIGS. 3A and 3B show a communicative connection between the energy source device system 340 and the controller 324 (and its data processing device system 310), the energy source device system 340 may also be connected to the transducers 306 or their respective electrodes 315 via a communicative connection that is independent of the communicative connection with the controller 324 (and its data processing device system 310). For example, the energy source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 or their respective electrodes 315 (e.g., via one or more communication lines through catheter body 314, elongated cable 316 or catheter sheath 312) that does not pass through the controller 324. In this regard, the energy source device system 340 may provide results of its delivering energy to, receiving energy from, or both delivering energy to and receiving energy from one or more of the transducers 306 or the respective electrodes 315 to the controller 324 (and its data processing device system 310) via the communicative connection between the energy source device system 340 and the controller 324.

The energy source device system 340 may, for example, provide energy in the form of electric current to various selected transducers 306 or their respective electrodes 315. Determination of a temperature characteristic, an electrical characteristic, or both, at a respective location at least proximate each of the various transducers 306 or their respective electrodes 315 may be made under the influence of energy or current provided by the energy source device system 340 in various embodiments. Energy provided to an electrode 315 by the energy source device system 340 may in turn be transmittable by the electrodes 315 to adjacent tissue (e.g., tissue forming a tissue wall surface). The energy source device system 340 may include various electric current sources or electrical power sources. In some embodiments, an indifferent electrode 326 is provided to receive at least a portion of the energy transmitted by at least some of the transducers 306 or their respective electrodes 315. Consequently, although not shown in FIGS. 3A and 3B, the indifferent electrode may be communicatively connected to the energy source device system 340 via one or more communication lines in some embodiments. The indifferent electrode 326 is typically configured to be positioned outside of a bodily cavity and may be positioned on an exterior body surface and, in some embodiments, although shown separately in FIGS. 3A and 3B, is considered part of the energy source device system 340.

Structure 308 may be delivered and retrieved via a catheter member, for example, a catheter sheath 312. In some embodiments, the structure 308 provides expansion and contraction capabilities for a portion of a medical device (e.g., an arrangement, distribution or array of transducers 306). The transducers 306 may form part of, be positioned or located on, mounted or otherwise carried on the structure 308 and the structure may be configurable to be appropriately sized to slide within catheter sheath 312 in order to be deployed percutaneously or intravascularly. FIG. 3A shows one embodiment of such a structure, where the elongate members 304, in some embodiments, are stacked in the delivery or unexpanded configuration to facilitate fitting within the flexible catheter sheath 312. In some embodiments, each of the elongate members 304 includes a respective distal end 305 (only one called out in FIG. 3A), a respective proximal end 307 (only one called out in FIG. 3A) and an intermediate portion 309 (only one called out in FIG. 3A) positioned between the proximal end 307 and the distal end 305. Correspondingly, in some embodiments, structure 308 includes a proximal portion 308a and a distal portion 308b. In some embodiments, the proximal and the distal portions 308a, 308b include respective portions of elongate members 304. The respective intermediate portion 309 of each elongate member 304 may include a first or front surface 318a that is positionable to face an interior tissue surface within a bodily cavity and a second or back surface 318b opposite across a thickness of the intermediate portion 309 from the front surface 318a. In some embodiments, each elongate member 304 includes a twisted portion at a location proximate proximal end 307. The transducers 306 may be arranged in various distributions or arrangements in various embodiments. In some embodiments, various ones of the transducers 306 are spaced apart from one another in a spaced apart distribution as shown, for example in at least FIGS. 3A and 3B. In some embodiments, various regions of space are located between various pairs of the transducers 306. For example, in FIG. 3B the transducer-based device system 300 includes at least a first transducer 306a, a second transducer 306b and a third transducer 306c (all collectively referred to as transducers 306). In some embodiments, each of the first, the second, and the third transducers 306a, 306b and 306c are adjacent transducers in the spaced apart distribution. In some embodiments, the first and the second transducers 306a, 306b are located on different elongate members 304 while the second and the third transducers 306b, 306c are located on a same elongate member 304. In some embodiments, a first region of space 350 is between the first and the second transducers 306a, 306b. In some embodiments, the first region of space 350 is not associated with any physical portion of structure 308. In some embodiments, a second region of space 360 associated with a physical portion of device system 300 (e.g., a portion of an elongate member 304) is between the second and the third transducers 306b, 306c. In some embodiments, each of the first and the second regions of space 350, 360 do not include a transducer or electrode thereof of transducer-based device system 300. In some embodiments, each of the first and the second regions of space 350, 360 do not include any transducer or electrode.

It is noted that other embodiments need not employ a group of elongate members 304 as employed in the illustrated figures. For example, other embodiments may employ a structure including one or more surfaces, at least a portion of the one or more surfaces defining one or more openings in the structure. In these embodiments, a region of space not associated with any physical portion of the structure may extend over at least part of an opening of the one or more openings. In other example embodiments, other structures may be employed to support or carry transducers of a transducer-based device provided by various flexible circuit structures (e.g., by various embodiments associated with, e.g., at least FIGS. 4, 5, 6, 7, 8, 9A, 9B, 10, 11, 12 and 13). In some embodiments, an elongated catheter member may be used to distribute the flexible circuit structure-based transducers in a linear or curvilinear array. Basket catheters or balloon catheters may be used to distribute the flexible circuit structure-based transducers in a two-dimensional or three-dimensional array.

In various example embodiments, the energy transmission surface 319 of each electrode 315 is provided by an electrically conductive surface. In some embodiments, each of the electrodes 315 is located on various surfaces of an elongate member 304 (e.g., front surfaces 318a or back surfaces 318b). In some embodiments, various electrodes 315 are located on one, but not both of the respective front surface 318a and respective back surface 318b of each of various ones of the elongate members 304. For example, various electrodes 315 may be located only on the respective front surfaces 318a of each of the various ones of the elongate members 304. Three of the electrodes 315 are identified as electrodes 315a, 315b and 315c in FIG. 3B. Three of the energy transmission surfaces 319 are identified as 319a, 319b and 319c in FIG. 3B. In various embodiments, it is intended or designed to have the entirety of each of various ones of the energy transmission surfaces 319 be available or exposed (e.g., without some obstruction preventing at least some of the ability) to contact non-fluidic tissue at least when structure 308 is positioned in a bodily cavity in the expanded configuration. In various embodiments, it is intended or designed to have no portion of each of at least one of the energy transmission surfaces 319 contact fluidic tissue when the at least one of the energy transmission surfaces 319 contacts a contiguous portion of a non-fluidic tissue surface (e.g., a tissue surface that defines a tissue wall).

In various embodiments, the respective shape of various electrically conductive surfaces (e.g., energy transmission surfaces 319) of various ones of the electrodes 315 vary among the electrodes 315. In various embodiments, one or more dimensions or sizes of various electrically conductive surfaces (e.g., energy transmission surfaces 319) of at least some of the electrodes 315 vary among the electrodes 315. The shape or size variances associated with various ones of the electrodes 315 may be motivated for various reasons. For example, in various embodiments, the shapes or sizes of various ones of the electrodes 315 may be controlled in response to various size or dimensional constraints imposed by structure 308.

Figure 5:
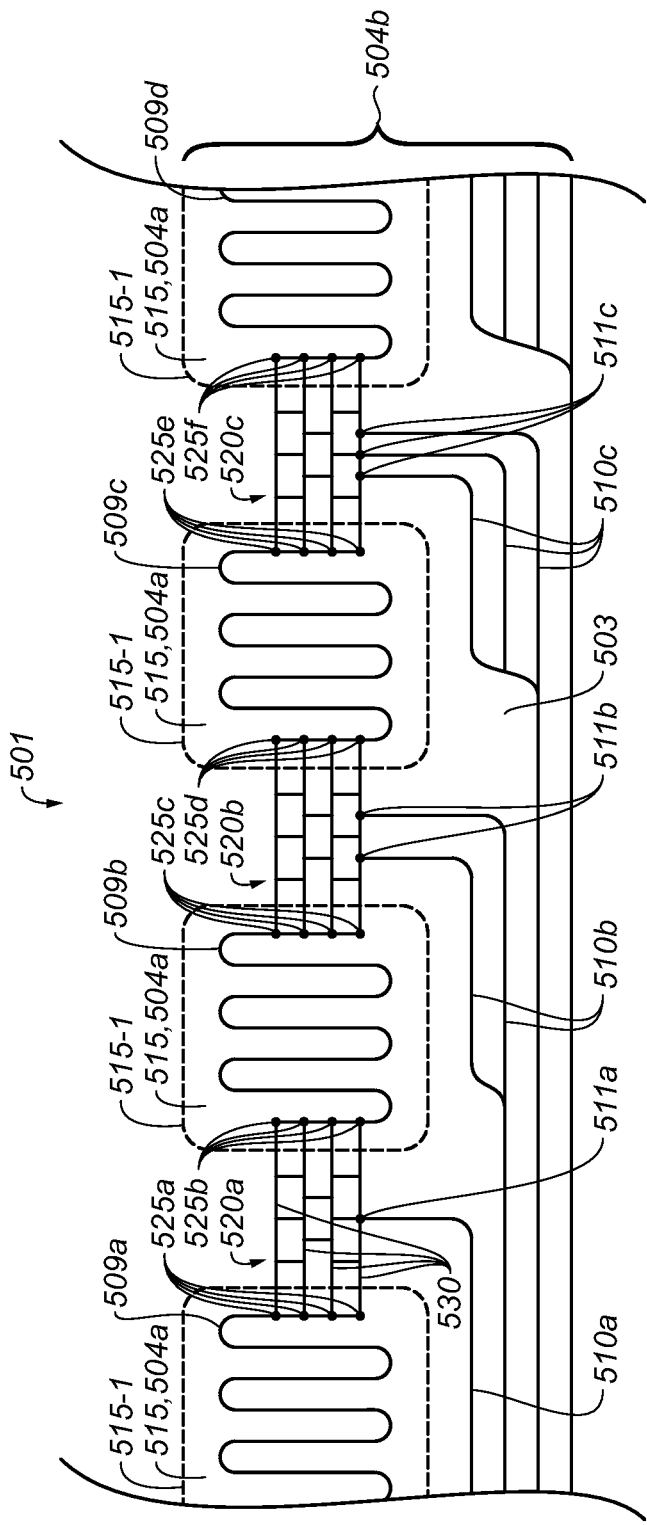
FIG. 5 is a schematic representation of a flexible circuit structure that includes a patterned conductive layer, according to various example embodiments.

FIG. 5 is a schematic plan view of at least one conductive layer 504b of a transducer-based device system that includes a flexible circuit structure 501 providing a plurality of resistive elements 509 (four called out in FIG. 5 as reference symbols 509a, 509b, 509c, 509d) according to various example embodiments. It should be noted that the various elements and structures described above with respect to flexible circuit structure 401 may also be applicable to flexible circuit structure 501. In this regard, in some embodiments, illustrated structures having reference numerals in each of FIGS. 5-8, 9A, 9B, 10, 11, 12, and 13 that end in the same digits or characters as those corresponding illustrated structures in FIG. 4 may represent the same or an alternate embodiment of the corresponding illustrated structure in FIG. 4. For example, in some embodiments, the electrically conductive layer 504b corresponds to an alternate embodiment of the electrically conductive layer 404b.

In some embodiments, at least (a) one or more conductive layers or (b) one or more nonconductive layers are positioned atop or overlaid on the electrically conductive layer 504b. A group of electrodes 515 are shown in broken lines according to some embodiments. In some embodiments, at least some of the electrodes 515 are provided by a conductive layer other than conductive layer 504b. In some embodiments, at least some of the electrodes 515 are provided by electrically conductive layer 504a (above layer 504b according to the perspective shown in FIG. 5). In some embodiments, at least one nonconductive layer is located between conductive layers 504a and 504b. In some embodiments, a portion of each electrode 515 is positioned in an overlapping arrangement (e.g., as viewed in the plan view of FIG. 5) with a portion of at least one of the resistive elements 509. In some embodiments, a portion of each electrode 515 is positioned in an overlapping arrangement (e.g., as viewed in the plan view of FIG. 5) with a portion of at least one of conductive meshes 520 (described below). It is noted that an electrode (e.g., electrode 315, 415 and 515) may be provided (e.g., in a similar or same overlapping arrangement) in at least some of the embodiments described below, even where it may not be explicitly shown. In some embodiments, the at least one conductive layer 504b is provided on, formed on or in, or supported by at least one electrically nonconductive layer 503 which may correspond to nonconductive flexible layer 403b in some embodiments. In some embodiments, a plurality of nonconductive flexible layers may be interleaved with the electrically conductive flexible layers 504a, 504b.

In some embodiments, resistive elements 509 provide temperature sensors 408 having a targeted electrical resistance (e.g., a resistance value targeted by an element including a particular amount of conductive material arranged with a particular configuration (e.g., a particular, width, length, and thickness suitable for substantially achieving the targeted resistance within some particular error bounds). In some embodiments, portions of various leads 510 (three called out in FIG. 5 as reference symbols 510a, 510b, and 510c) are arranged to allow for sampling of electrical voltage between each respective resistive element 509. In some embodiments, portions of various leads 510 (three called out in FIG. 5 as reference symbols 510a, 510b, and 510c) are arranged to allow for sampling of electrical voltage across each respective resistive element 509. In some embodiments, the resistive elements 509 are connected in series by conductive meshes 520 (three called out in FIG. 5 as reference symbols 520a, 520b, and 520c) to allow electric current to pass through all of the resistive elements 509. In some embodiments, the serial connection of resistive elements 509 by conductive meshes 520 provides at least one electric current flow path through the resistive elements 509. In some embodiments, the conductive meshes 520 provide multiple electrical pathways for the electric current to pass through all of the resistive elements 509.

In some embodiments, the conductive meshes 520 are connected to the resistive elements 509 by a plurality of electrical connection points. In some embodiments, each conductive mesh 520 is connected to each of the respective adjacent pair of resistive elements 409 by an electrical connection point set 525 (six particular electrical connection point sets called out in FIG. 5 as reference symbols 525a, 525b, 525c, 525d, 525e and 525f). The electrical connection points of each of the electrical connection point sets 525 are schematically depicted by dots "•" in FIG. 5. As an example, in FIG. 5, the conductive mesh 520a is connected to the resistive element 509a by connection point set 525a. The conductive mesh 520a is also connected to the resistive element 509b by connection point set 525b. Similarly, in FIG. 5, the conductive mesh 520b is connected to the resistive element 509b by connection point set 525c and to the resistive element 509c by connection point set 525d. Similarly, in FIG. 5, the conductive mesh 520c is connected to the resistive element 509c by connection point set 525e and to the resistive element 509d by connection point set 525f. Each connection point set 525 may include a plurality of electrical connection points connecting the conductive mesh 520 to the resistive element 509. In some embodiments, the connection point set 525 is arranged away from an electrode edge 515-1 (e.g., as viewed in the plan view of FIG. 5) to reduce the likelihood of cracks or open or otherwise impaired circuits due to flexing or other stress-imparting actions. In some embodiments, the electrical connection point set 525 is positioned within a perimeter of the electrode 515 defined at least in part by electrode edge 515-1 and overlaps, or is overlapped by, the electrode 515 to reduce the likelihood of cracks or open circuits due to flexing or other stress-imparting actions. It is noted that various connection points between various patterned features may act as stress risers and it is preferable, in some embodiments, to keep the connection points away from other stress-concentrating elements such as the edge 515-1 of a relatively stiff electrode 515.

FIGS. 4 and 5 include different example embodiments of conductive meshes 420 and 520. Each of the conductive meshes 420 and 520 provide a plurality of electrical pathways for the flow of electric current from one resistive element 409, 509 to the next serially connected resistive element 409, 509, according to some embodiments. In some embodiments, the phrase "adjacent resistive elements" or "adjacent pair of resistive elements" refers to a pair of resistive elements 409, 509 serially connected to each other (e.g., by a same conductive mesh 420, 520 or group of conductive meshes (e.g., meshes 1121b, 1121c discussed below with respect to FIG. 11)), with no other resistive element 409, 509 serially connected in between the two resistive elements of the adjacent pair of elements. For example, in FIG. 5, resistive elements 509a and 509b are adjacent resistive elements. Similarly, resistive elements 509b and 509c are adjacent resistive elements. However, resistive elements 509a and 509c are not adjacent resistive elements, because the resistive element 509b is serially connected between resistive element 509a and resistive element 509b.

In some embodiments, each resistive element 409, 509 forms at least part of a respective transducer (e.g., transducer 406) and is configured to perform a specific predetermined function of the part of the respective transducer. For example, in various embodiments, it may be desired that each of resistive elements 409, 509 have a serpentine form particularly sized and shaped to increase the overall electrical resistance of the resistive element while distributing portions of the resistive element over as much of a particular area as possible. This may be motivated by various reasons. For example, it may be desired to distribute portions of resistive elements 409, 509 to occupy an area having overall dimensions and an overall shape that approximate the overall dimensions and overall shape of a respective overlapping electrode 415, 515, thereby allowing the resistance e.g., and consequently the temperature (e.g., average temperature) to be determined over a particular tissue area and subsequently treat (e.g., via tissue ablation) the same particular tissue region with the electrode having a size and shape that effectively matches the size and shape of the particular tissue region. It is understood that various interconnecting elements/structures (e.g., leads, conductive meshes) between the resistive elements also are resistive in nature, and in some cases, their specific resistances must be considered. However, these interconnecting elements/structures are not considered to be resistive elements in this disclosure and the accompanying claims, since their function is not to directly form part of a specific transducer, but rather, act as interconnects between various transducers. Accordingly, in various embodiments, adjacent resistive elements are provided by an adjacent pair of resistive elements (e.g., 409, 509, 609, 709, 809), the resistive elements of the adjacent pair interconnected by an interconnecting element or structure.

The conductive meshes 420, 520 are not limited to the arrangement shown in FIGS. 4 and 5 and may include any arrangement of more than one conductive segment 430, 530 connecting two adjacent resistive elements 409, 509 so as to provide multiplicity, redundancy, and failure tolerance for the electric current flow path. In some embodiments, each of the conductive meshes 420, 520 connecting the resistive elements 409, 509 in a serial electrical arrangement may have different shapes and configurations.

FIG. 5 also shows measurement leads 510 (three called out in FIG. 5 as reference symbols 510a, 510b and 510c) connecting to respective conductive meshes 520. In some embodiments, the measurement leads 510 are electrically connected to the conductive meshes 520 at a plurality of electrical connection points forming a measurement lead connection point set. In some embodiments, at least some of the measurement leads 510 are voltage measurement leads 510 connected to a voltage measurement system to measure voltage across a resistive element (e.g., 409, 509, 609, 709, 809). In some embodiments, at least some of the measurement leads 510 are current measurement leads 510 connected to a current measurement system to measure electric current flowing through a resistive element (e.g., 409, 509, 609, 709, 809). In some embodiments, a first measurement lead 510a is electrically connected to a first conductive mesh 520a at a first measurement lead connection point set 511a. The first measurement lead connection point set 511a includes one or more electrical connection points that connect the first measurement lead 510a to the first conductive mesh 520a. A second measurement lead 510b is electrically connected to a second conductive mesh 520b at a second measurement lead connection point set 511b. The second measurement lead connection point set 511b includes one or more electrical connection points that connect the second measurement lead 510b to the second conductive mesh 520b. In some embodiments, the second measurement lead connection point set 511b includes a greater number of electrical connection points than the first measurement lead connection point set 511a. For example, in some embodiments, as illustrated in FIG. 5, the first measurement lead connection point set 511a includes a single connection point, and the second measurement lead connection point set 511b includes two connection points. A third measurement lead 510c is electrically connected to a third conductive mesh 520c at a third measurement lead connection point set 511c. The third measurement lead connection point set 511c includes one or more electrical connection points that connect the third measurement lead 510c to the third conductive mesh 520c. In various embodiments, each of the first, the second, and the third measurement lead connection point sets 511a, 511b, 511c (collectively, electrical connection point sets 511) includes a different number of connection points than at least one other of the first, the second, and the third measurement lead connection point sets 511a, 511b, 511c. In some embodiments, first measurement lead 510a connects to the conductive mesh 520a at one electrical connection point, second measurement lead 510b connects to the conductive mesh 520b at two electrical connection points, and third measurement lead 510c connects to the conductive mesh 520c at three electrical connection points. In some embodiments, as shown in FIG. 5, the measurement lead 510b branches into two measurement leads or lead portions, and the measurement lead 510c branches into three measurement leads or lead portions, providing further multiplicity, redundancy, and failure tolerance in case of a crack or open circuit developing in one of the downstream portions (e.g., post-branching closer to the respective mesh 520) of the measurement leads 510. It is noted that other embodiments may provide multiplicity, redundancy, and failure tolerance by employing multiple separate measurement leads 510, instead of branched measurement leads 510, connected to some or all of the conductive meshes 520. Multiple separate leads 510 may improve multiplicity, redundancy, and failure tolerance as compared to branched leads 510, while branched leads may reduce manufacturing cost, circuit footprint, and circuit design complexity as compared to multiple separate leads 510.

In some embodiments, various portions of the measurement leads 510 are arranged (e.g., patterned) to provide a uniform, parallel or substantially parallel arrangement of various portions of the measurement leads 510. In some embodiments, the first measurement lead 510a includes a single conductive trace that connects to the first conductive mesh 520a. In some embodiments, second measurement lead 510b is split into two second measurement leads or traces, a first of the two second measurement leads or traces being provided (e.g., patterned) in a region adjacent a region occupied by the first measurement lead 510a. In some embodiments, the two second measurement leads/traces are connected to the second conductive mesh 520b at two electrical connection points. This arrangement may advantageously reduce the space required by the second measurement lead 510b in various regions adjacent the first measurement lead 510a while providing some degree of redundancy should a failure occur in one of the two second measurement leads or traces 510b. Increasing the number of measurement lead connection points 511 for downstream meshes 520 (e.g., meshes 520 further from the destination of the signals provided by the respective meshes 520) may be beneficial and appropriate at least because circuit connection failures may be more likely downstream, according to some embodiments. Further, increasing the number of measurement lead connection points 511 for downstream meshes 520 may be beneficial and appropriate at least because such a configuration may facilitate maintaining a uniform or relatively uniform stiffness throughout the length of the flexible circuit structure 501 by the connecting leads. For example, according to some embodiments, the first measurement lead 510a extends downstream toward the first connection point set 511a, and a preferred location for the split in second measurement lead 510b is in a region downstream of the first measurement lead connection point set 511a to take advantage of the space made available by the absence of the first measurement lead 510a. If such space is not filled, there may be less structure in the flexible circuit structure 501 along the length of the flexible circuit structure 501 in a downstream direction, which may act to varying flexibility of the circuit structure 501 in the downstream direction and expose the circuit elements to increased stress due to the varying flexibility. In some embodiments, a split in a measurement lead 510 is positioned away from electrode edges 515-1 to reduce overall stress risers.

In this regard, in some embodiments, the third measurement lead 510c branches into three third measurement leads or traces 510c. At least one of the third measurement leads 510c may be provided (e.g., patterned) in a region vacated by the second measurement lead 510b due to a presence of a split in the second measurement lead 510b. That is, if the second measurement lead 510b was made up of two separate leads, a respective region would be required for each of the two separate leads. The branched configuration of second measurement lead 510b allows one of these respective regions to be vacated and be, instead, occupied by the third measurement lead 510c. In some embodiments, the three third measurement leads/traces are connected to the third conductive mesh 520c at three electrical connection points.

In some embodiments, the flexible circuit structure 501 is electrically connected to a voltage or current measurement circuit, discussed above, by the plurality of measurement leads 510. Respective pairs of measurement leads 510 may be positioned to sense voltage across each resistive element 509. For example, in FIG. 5, measurement leads 510a and 510b are positioned to sense voltage across resistive element 509b, and measurement leads 510b and 510c are positioned to sense voltage across resistive element 509c.

FIGS. 6, 7, 8, 9A, and 9B show various example embodiments of flexible circuit structures including multiple or redundant electric current flow paths. It should be noted that the descriptions provided above with respect to flexible circuit structures 401, 501 may also be applicable to various example embodiments shown in each of FIGS. 6, 7, 8, 9A, and 9B, as discussed above. It should also be noted that the specific number or arrangement of various elements (such as resistive elements, conductive meshes, electrodes, conductive segments, or measurement leads) in FIGS. 6, 7, 8, and 9 are non-limiting and provided as illustrative examples that may be beneficial in certain environments or applications. Other example embodiments may include different numbers or arrangements of various elements. Each of the example embodiments shown in FIGS. 6, 7, 8, and 9 includes a plurality of electrical pathways to provide multiple or alternate electric current flow paths in the event of failure (such as a crack or other failure mechanism) of any particular electric current flow path.

Figure 6:
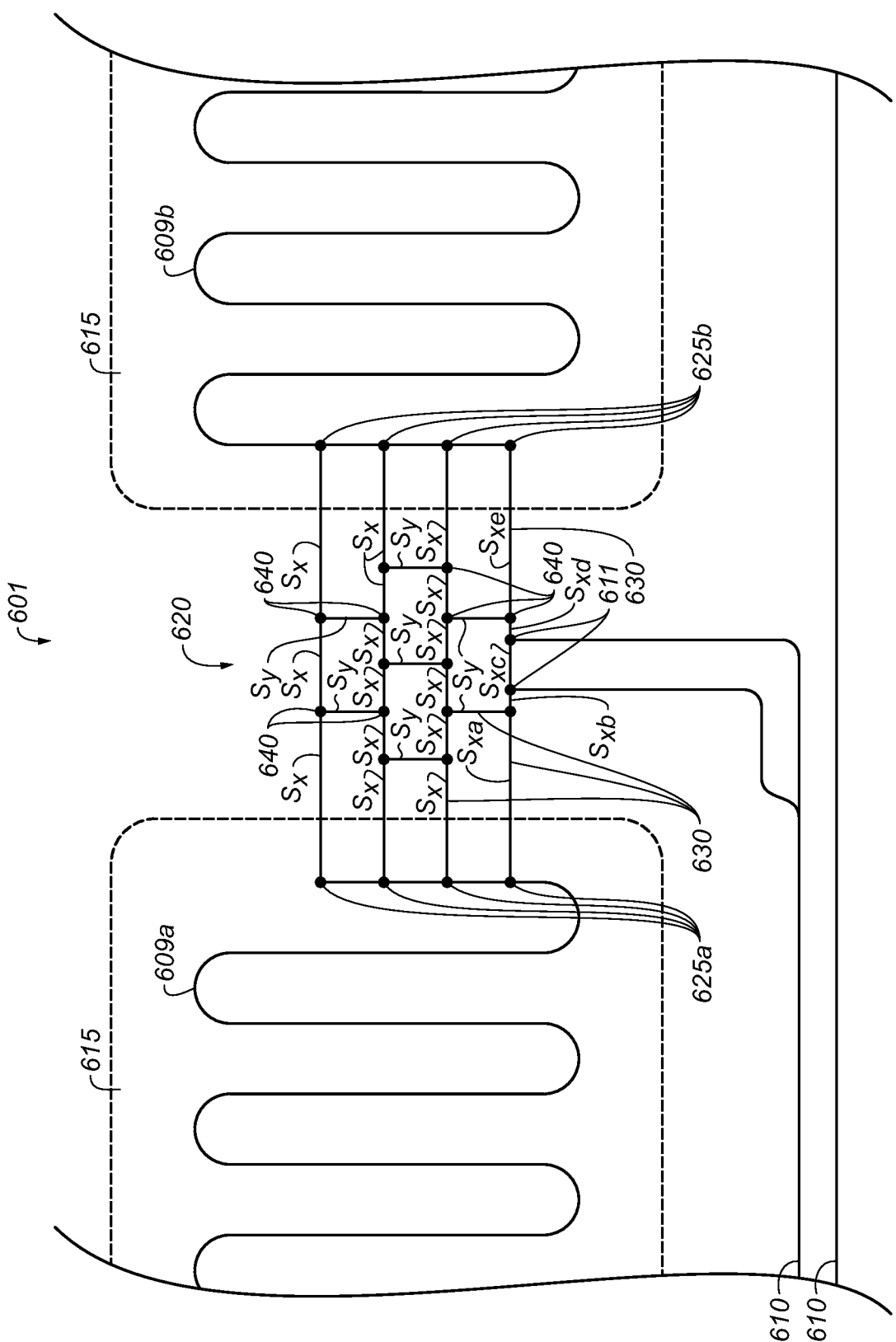
FIG. 6 is a schematic representation of a conductive mesh that includes a plurality of conductive segments, according to various example embodiments.

FIG. 6 is a schematic plan view of a flexible circuit structure 601 that includes a conductive mesh 620 electrically connected and directly connected to adjacent resistive elements 609a, 609b (collectively 609) by electrical connection point sets 625a, 625b, according to various example embodiments. The conductive mesh 620 and resistive elements 609a, 609b may form part of a flexible circuit structure 401, 501 according to various embodiments, as discussed above. In this regard, as discussed above, in some embodiments, the various elements and structures illustrated in FIG. 6 may correspond to the same or different embodiments of such elements and structures described above with respect to FIG. 4 or any other figure herein including such elements and structures, and vice versa. While this statement is made particularly with respect to FIG. 6, the same applies to at least each of FIGS. 4, 5, 7, 8, 9A, 9B, 10, 11, 12, and 13. For example, the various elements and structures described above with respect to flexible circuit structure 401 and 501 may also be applicable to flexible circuit structure 601. In this regard, the conductive meshes 420, 520, and 620 show non-limiting examples of conductive meshes according to various embodiments.

In some embodiments, the conductive mesh 620 includes a plurality of conductive segments 630 spatially arranged to provide a plurality of electrical pathways between the resistive elements of the respective adjacent pair of resistive elements 609a, 609b. For clarity of drawing and ease of discussion, the conductive segments 430, 530, 630 (or other conductive segments described herein) may also be referred to as conductive segments S. In FIG. 6, the plurality of conductive segments S includes a first conductive segment set in which the segments 630 thereof are each identified as segments $S_x$, and a second conductive segment set in which the segments 630 thereof are each identified as segments $S_y$.

Each conductive segment 630 provides a respective portion of each of at least some of the plurality of electrical pathways. The electrical pathways are arranged in a network between the resistive elements 609a, 609b of the respective adjacent pair of resistive elements 609. In the various embodiments associated with FIG. 6, each conductive segment 630 in the conductive mesh 620 is a portion of a conductive trace formed of conductor material. Each conductive segment 630 may be patterned in an electrically conductive layer (e.g., conductive layer 404b, 504b). Each conductive segment 630 may be defined, at least in part, as including a connection point (e.g., a connection point in the electrical connection point set 625a, 625b) to a resistive element 609, an intersection point (e.g., an intersection point 640 (a few called out in FIG. 6)) with another conductive segment 630, or an intersection point (e.g., 611) with a measurement lead 610. In the example embodiments of FIG. 6, there are four electrical connection points in the electrical connection point set 625a, four electrical connection points in the electrical connection point set 625b, and fourteen intersection points 640. For clarity of drawing, only a subset of the intersection points 640 is labeled. The electrical connection points of each of the electrical connection point sets 625a, 625b and the intersection points 640, 611 are schematically depicted by dots "*" in FIG. 6. Other embodiments may employ other numbers of conductive segments 630 or other arrangements of conductive segments 630. Consequently, the number of electrical connections points in electrical connection point sets 625a, 625b is not limiting, and the numbers of intersection points 640 and 611 are non-limiting.

In some embodiments, the conductive mesh 620 and its conductive segments 630 exist within multiple conductive flexible circuit layers of the flexible circuit structure (e.g., 401, 501). For example, in some embodiments, the vertical conductive segments $S_y$ may reside within a lower conductive flexible circuit layer than the horizontal conductive segments $S_x$. In such embodiments, the intersection points 640 may represent vias that pass through the different conductive flexible circuit layers and connect the vertical conductive segments $S_y$ in the lower conductive flexible circuit layer with the horizontal conductive segments S, in the upper conductive flexible circuit layer. In some embodiments where the resistive elements or electrical loads 609a, 609b are be temperature sensors, the conductive mesh 620 is an electrical-connection-arrangement that connects the respective adjacent pair of temperature sensors 609a, 609b by at least one via arranged to electrically connect different ones of the conductive flexible circuit layers. Accordingly, it is to be understood that the conductive meshes or other electrical-connection-arrangements described herein need not be entirely located within a same circuit layer. By having the conductive mesh (e.g., at least 620) or other electrical-connection-arrangement span multiple circuit layers, additional fault tolerance may be facilitated, according to some embodiments.

It is noted that FIG. 6 includes a measurement lead 610 electrically connected to the conductive mesh 620 (FIG. 6 shows another measurement lead 610 passing onto another conductive mesh (not shown), according to some embodiments) via corresponding measurement lead connection point set 611 to measure voltage or current according to various embodiments. Typically, in these various embodiments, the impedance or resistance associated with the measurement lead 610 (connected to the conductive mesh 620) is made to be significantly higher than the impedance or resistance of at least the conductive mesh 620, the resistive element 609a, or the resistive element 609b to cause the electric current to flow between resistive elements 609a, 609b predominately or almost entirely through conductive mesh 620 rather than through measurement lead 610 (connected to the conductive mesh 620). Therefore, in these particular embodiments, the measurement lead intersection point set 611 may be considered separately from the set of intersection points 640.

In some embodiments, a conductive segment (e.g., 630) (a) originates at (i) an electrical connection point (e.g., a connection point of the electrical connection point set 625) with a resistive element (e.g., 609), (ii) an intersection point (e.g., 640) with another conductive segment (e.g., 630), or (iii) an intersection point (e.g., 611) with a measurement lead (e.g., 610); and (b) terminates at (i) an electrical connection point (e.g., a connection point of the electrical connection point set 625) with a resistive element (e.g., 609), (ii) an intersection point (e.g., 640) with another conductive segment (e.g., 630), or (iii) an intersection point (e.g., 611) with a measurement lead (e.g., 610). The conductive segments 630 may be linear or non-linear in form, may have different shapes, and are not limited to extending in any particular direction.

In some embodiments, the conductive mesh 620 includes a plurality of electrical connection points electrically connecting a respective set of the plurality of conductive segments 630 to each resistive element 609a, 609b of the respective adjacent pair of resistive elements 609. In some embodiments, at least one of the plurality of electrical connection points (e.g., an electrical connection point included in the electrical connection point set 625a) of the conductive mesh 620 is located adjacent or on one resistive element of the respective adjacent pairs of resistive elements 609 (e.g., resistive element 609a). The at least one electrical connection point may be electrically connected to at least two of the plurality of electrical connection points (e.g., two electrical connection points included in the electrical connection point set 625b) located at least adjacent or on the other resistive element of the respective adjacent pair of resistive elements 609 (e.g., resistive element 609b). In some embodiments, the at least two of the plurality of electrical connection points do not include any electrical connection points in common with the at least one of the plurality of electrical connection points (e.g., two electrical connection points in electrical connection point set 625b are different than an electrical connection point in electrical connection point set 625a).

In some embodiments, at least one electrical connection point (e.g., at least one electrical connection point in the electrical connection point set 625a) is located closer to resistive element 609a than to at least one other electrical connection point (e.g., at least one electrical connection point in the electrical connection point set 625b). In effect, this arrangement of electrical connection points (and other arrangements of other embodiments described in this disclosure) provides increased multiplicity, redundancy, and failure tolerance in particular portions of the flexible circuit structure 601 that may be susceptible to crack under various stress-causing applications. In some embodiments, at least one electrical connection point (e.g., at least one electrical connection point in electrical connection point set 625a) is located closer to resistive element 609a than to each of at least two electrical connection points (e.g., each of at least two electrical connection points in the electrical connection point set 625b). The at least one electrical connection point in set 625a may be electrically connected to the at least two electrical connection points in set 625b according to various embodiments (e.g., via at least some of the conductive segments 630). In some embodiments, at least one electrical connection point (e.g., at least one electrical connection point in the electrical connection point set 625a) is located closer to resistive element 609a than a distance separating at least one other electrical connection point (e.g., at least one electrical connection point in electrical connection point set 625b) and resistive element 609a. In some embodiments, at least one electrical connection point (e.g., at least one electrical connection point in the electrical connection point set 625a) is located by a closer distance to resistive element 609a than each of a respective distance separating each of at least two other electrical connection points (e.g., at least two electrical connection points in electrical connection point set 625b) and resistive element 609a. The at least one electrical connection point may be electrically connected to the at least two other electrical connection points according to various embodiments.

In some embodiments, the first electrical connection point set 625a, the second electrical connection point set 625b or each of the first electrical connection point set 625a and the second electrical connection point set 625b includes at least two electrical connection points. The plurality of electrical connection points in each of the sets 625 provides multiple or redundant electric current flow paths through the plurality of electrical pathways in the flexible circuit structure 601. If a particular electrical pathway is rendered open due to a crack, the open pathway is deemed to not be included in an electric current flow path, because electric current is not able to flow through the open pathway in the context of the broader circuit, according to some embodiments.

The conductive mesh 620 may include various spatial arrangements of conductive segments 630 that provide at least two electric current flow paths through the conductive mesh 620 for multiplicity, redundancy, and failure tolerance. For example, in some embodiments, the plurality of conductive segments 630 of the conductive mesh 620 includes a first conductive segment set in which each segment in the first conductive segment set extends in a first direction (e.g., the first conductive segment set whose segments are identified as S, and proceed horizontally in FIG. 6) and a second conductive segment set in which each segment in the second conductive segment set extends in a second direction (e.g., the second conductive segment set whose segments are identified as $S_y$, and proceed vertically in FIG. 6), the first direction (e.g., horizontal in the perspective of FIG. 6) being perpendicular or oblique to the second direction (e.g., vertical in the perspective of FIG. 6). In some embodiments, at least one of the conductive segments 630 in the first conductive segment set intersects with at least one of the conductive segments 630 in the second conductive segment set at an intersection point 640 (e.g., S, conductive segments intersect $S_y$ conductive segments in the example of FIG. 6).

It is noted that the plurality of conductive segments 630 spatially arranged to provide a plurality of electrical pathways between the resistive elements 609a, 609b advantageously allows for multiplicity, redundancy, and failure tolerance that can counter various failure modes that can occur in the interconnecting elements between the adjacent pair of resistive elements 609a, 609b. For example, a failure (e.g., a crack or other mechanism leading to an open circuit condition) in any of a set of the conductive segments 630 identified as S, still permit current flow between the resistive elements 609a, 609b. An open circuit condition developed in any one of the conductive segments S, is mitigated by existing electrical pathways (as well as alternate/additional current paths arising as a consequence of the open circuit condition) provided by others of the conductive segments 630 that have not experienced an open circuit condition. In this regard, it is understood that various combinations of conductive segments $S_x$ and $S_y$ may provide the existing electrical pathways or alternate/additional electrical pathways arising as a consequence of the failure condition (e.g., open circuit condition). Another example advantage associated with the plurality of electrical pathways provided by the plurality of conductive segments 630 allows for continuity in the ability to measure voltage with the measurement lead 610 during a failure (e.g., a crack or other form of open circuit failure) in any of a set of the conductive segments 630. For example, various ones of the conductive segments $S_y$ allow measurement via the measurement lead 610 (connected to the conductive mesh 620) to continue should an open circuit failure occur in at least one of the conductive segments $S_{xa}$, $S_{xb}$, $S_{xc}$, $S_{xd}$, $S_{xe}$. In this regard, particular ones of the conductive segments $S_y$ connected to conductive segments $S_{xa}$, $S_{xb}$, $S_{xc}$, $S_{xd}$, and $S_{xe}$ allow the measurement to be continued at electric current bearing portions of the conductive mesh 620.

A group of electrodes 615 are shown in broken lines in FIG. 6 according to some embodiments. In some embodiments, at least some of the electrodes 615 are provided by a conductive layer other than the conductive layer that at least one of the resistive elements 609 or conductive mesh 620 are formed from or in. In some embodiments, at least some of the electrodes 615 are provided by electrically conductive layers 404b. In some embodiments, at least one nonconductive layer (not shown in FIG. 6) is located between at least one of the resistive elements 609 or conductive mesh 620 and least some of the electrodes 615. In some embodiments, a portion of each electrode 615 is positioned in an overlapping arrangement (e.g., as viewed in the plan view of FIG. 6) with a portion of at least one of the resistive elements 609. In some embodiments, a portion of each electrode 615 is positioned in an overlapping arrangement (e.g., as viewed in the plan view of FIG. 6) with a portion of conductive meshes 620.

Figure 7:
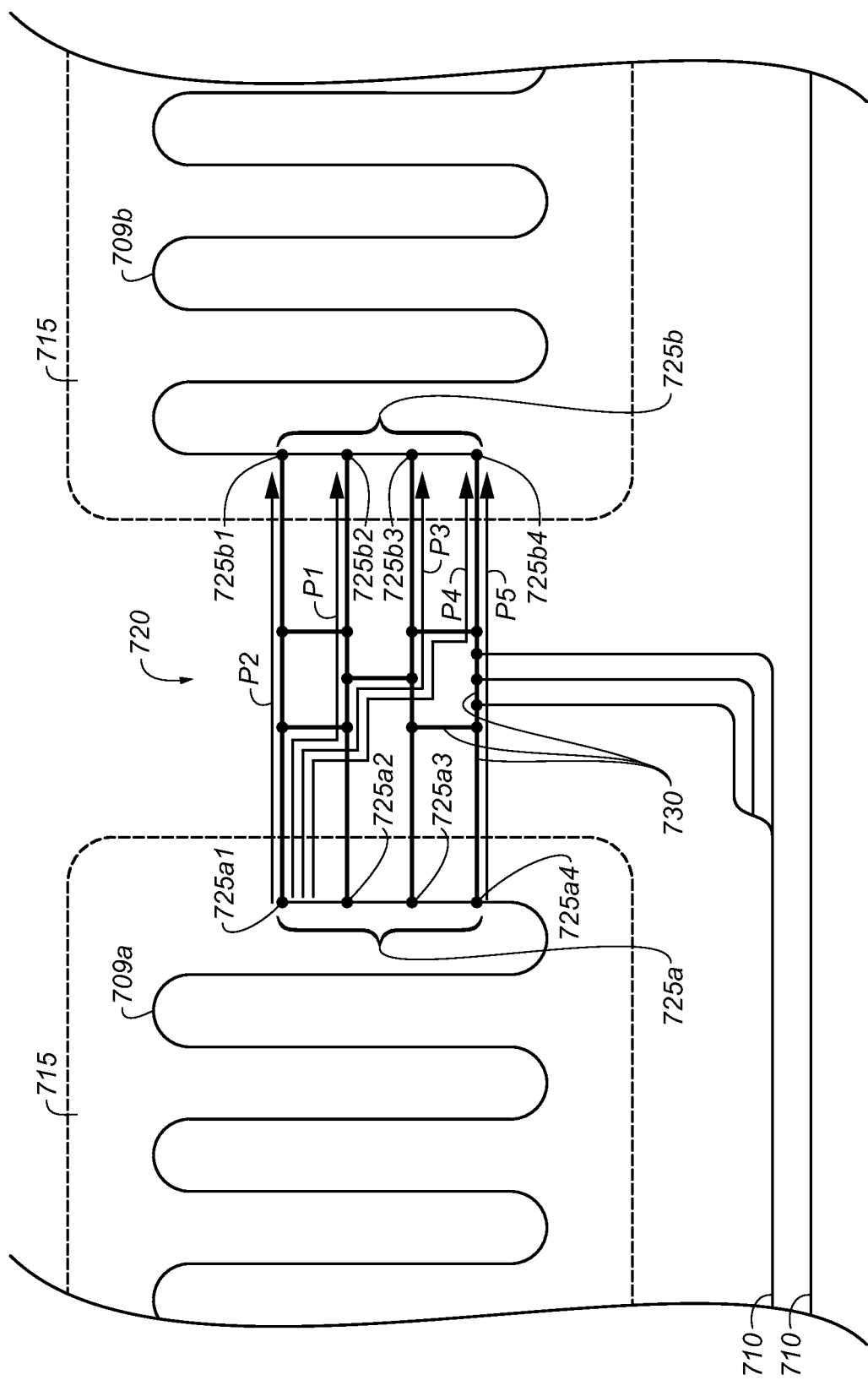
FIG. 7 is a schematic representation of a conductive mesh that provides a plurality of electrical pathways, according to various example embodiments.

FIG. 7 is a schematic plan view of at least one conductive mesh 720 electrically connected to adjacent resistive elements 709a, 709b (collectively, resistive elements 709) by electrical connection point sets 725a, 725b (collectively, electrical connection point sets 725) according to various example embodiments. It should be noted that the conductive mesh 720 shown in FIG. 7 is shown with a thicker line as compared to, for example, the conductive mesh 620 in FIG. 6. This thicker line for the conductive mesh 720 in FIG. 7 is provided merely to assist in visually distinguishing such mesh 720 from other items illustrated in FIG. 7 and is not intended to indicate a difference in a thickness of the conductive segments 730 of the conductive mesh 720 as compared to, e.g., the conductive mesh 620 in FIG. 6. The same comments apply to the thicker-lined conductive meshes 820 and 920b in FIGS. 8 and 9B, respectively.

As discussed above, in some embodiments, the various elements and structures illustrated in FIG. 7 may correspond to the same or different embodiments of such elements and structures described above with respect to FIG. 4 or any other figure herein including such elements and structures, and vice versa. For example, it should be noted that, in some embodiments, the various elements and structures described above with respect to flexible circuit structure 401, 501, and 601 may correspond to the respective elements and structures shown in FIG. 7, as described above, or vice versa. For another example, the conductive mesh 720 may correspond to conductive mesh 420, 520, or 620, or vice versa, according to various embodiments. Similarly, resistive elements 709 may correspond to resistive elements 409, 509, or 609, or vice versa, according to various embodiments. In some embodiments, conductive mesh 720 includes a plurality of conductive segments 730 (a few called out in FIG. 7) that are similar or identical in form, function, or both form and function with the conductive segments 630 described above in FIG. 6 (or other conductive segments described herein or otherwise within the scope of the present invention). The conductive mesh 720 and resistive elements 709a, 709b may form part of a flexible circuit structure (e.g., flexible circuit structure 401, 501, or 601) according to various embodiments. Each of the conductive segments 730 provides a portion of at least one of a plurality of electrical pathways P (five called out in FIG. 7 as reference symbols P1, P2, P3, P4, and P5) between the resistive elements 709a, 709b of each respective adjacent pair of resistive elements 709. It should be noted that since each of electrical pathways P1, P2, P3, P4, and P5 provides a continuous electrical connection from resistive element 709a to resistive element 709b, as shown in FIG. 7, each of such electrical pathways P1, P2, P3, P4, and P5 also is an electric current flow path from resistive element 709a to resistive element 709b, according to some embodiments. Accordingly, in embodiments where a continuous electrical connection is provided by an electrical pathway from a first circuit element to a second circuit element, it may also be stated that such electrical pathway is an electric current flow path from the first circuit element to the second circuit element.

The conductive mesh 720 is electrically connected and directly connected to the first resistive element 709a by the first electrical connection point set 725a and to the second resistive element 709b by the second electrical connection point set 725b. The electrical connection points of each of the sets 725a, 725b are schematically depicted by dots "*" in FIG. 7, as with FIG. 6 above and FIGS. 8, 9A, 9B, and 10-13 described below. Each of the electrical connection point sets 725a, 725b may include a plurality of electrical connection points. For example, in the illustrated embodiment shown in FIG. 7, the first electrical connection point set 725a includes electrical connection points 725a1, 725a2, 725a3 and 725a4, and the second electrical connection point set 725b includes electrical connection points 725b1, 725b2, 725b3, and 725b4. Other numbers of electrical connection points may be used in other embodiments. Each electrical connection point may electrically connect at least two of the plurality of electrical pathways between the resistive elements 709a, 709b of the respective adjacent pair of resistive elements 709 according to some embodiments. For example, in various embodiments according to FIG. 7, electrical connection point 725a1 connects at least four electrical pathways P1, P2, P3, and P4 to electrical connection points in the second electrical connection point set 725b.

In the various example embodiments shown in FIG. 7, electrical pathway P1 connects electrical connection points 725a1 and 725b2, electrical pathway P2 connects electrical connection points 725a1 and 725b1, electrical pathway P3 connects electrical connection points 725a1 and 725b3, electrical pathway P4 connects electrical connection points 725a1 and 725b4, and electrical pathway P5 connects electrical connection points 725a4 and 725b4.

In some embodiments, a total of the plurality of electrical pathways P provided by the plurality of conductive segments 730 of the conductive mesh 720 exceeds a total number of the electrical connection points in the first electrical connection point set 725a or a total number of the electrical connection points in the second electrical connection point set 725b due, at least in part, to the interconnecting arrangement of conductive segments 730 of the conductive mesh 720. For example, each of the first electrical connection point set 725a and the second electrical connection point set 725b has four electrical connection points, but there are more electrical pathways (and corresponding electric current flow paths), such as at least electrical pathways P1, P2, P3, P4, and P5.

A group of electrodes 715 are shown in broken lines in FIG. 7, according to some embodiments. In some embodiments, at least some of the electrodes 715 are provided by a conductive layer other than the conductive layer that at least one of the resistive elements 709 or conductive mesh 720 are formed from or in. In some embodiments, at least some of the electrodes 715 are provided by electrically conductive layers 404b. In some embodiments, at least one nonconductive layer (not shown in FIG. 7) is located between at least one of the resistive elements 709 or conductive mesh 720 and at least some of the electrodes 715. In some embodiments, a portion of each electrode 715 is positioned in an overlapping arrangement (e.g., as viewed in the plan view of FIG. 7) with a portion of at least one of the resistive elements 709. In some embodiments, a portion of each electrode 715 is positioned in an overlapping arrangement (e.g., as viewed in the plan view of FIG. 7) with a portion of conductive meshes 720. In some embodiments, a measurement lead 710 is electrically connected to conductive mesh 720 (FIG. 7 shows another measurement lead 710 passing onto another conductive mesh (not shown), according to some embodiments). As discussed with respect to flexible circuit structure 501, such measurement lead 710 (connected to conductive mesh 720) may form at least part of a circuit to measure voltage across or current through at least the resistive element 709a or the resistive element 709b.

Figure 8:
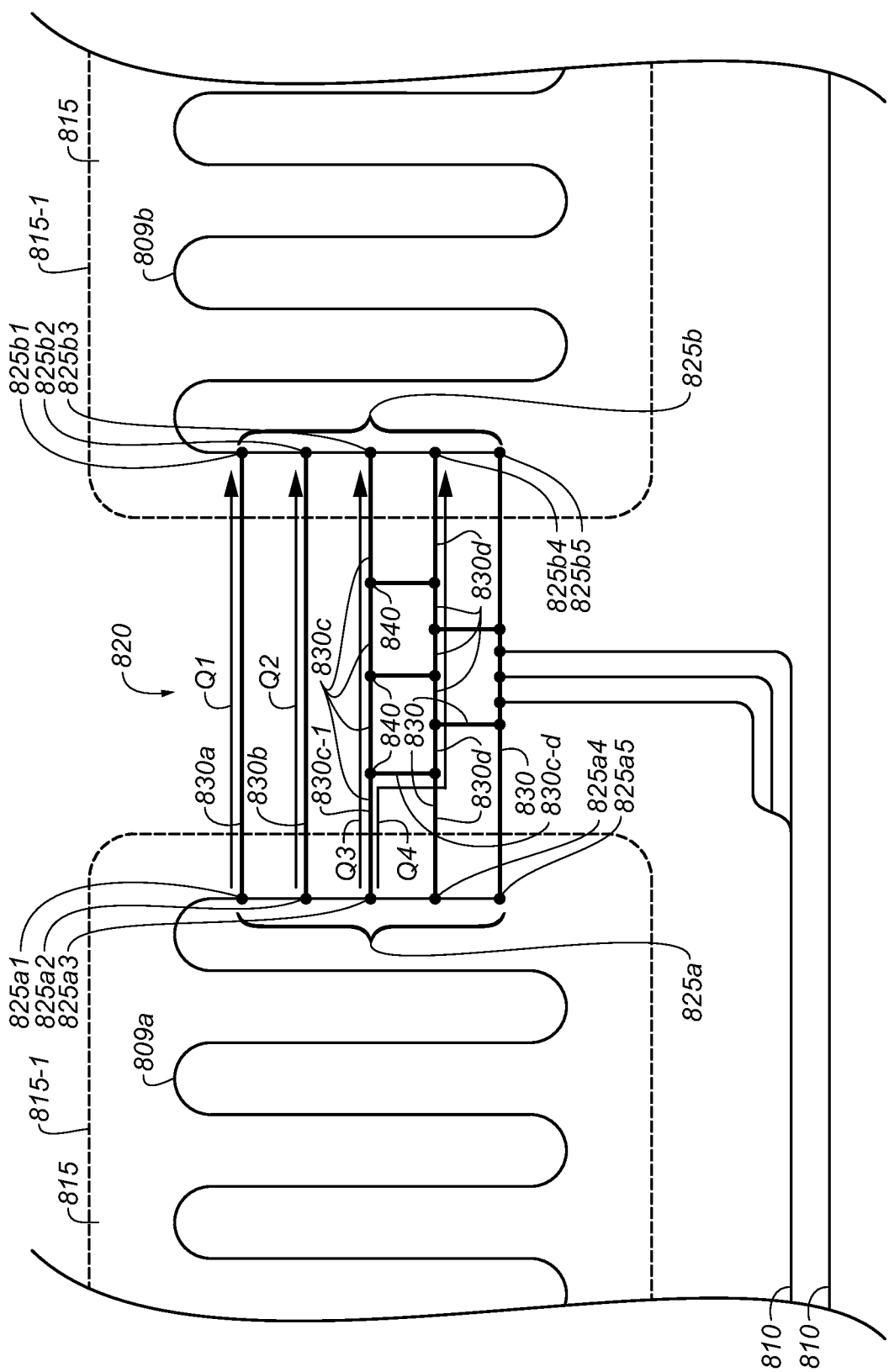
FIG. 8 is a schematic representation of another conductive mesh that provides a plurality of electrical pathways, according to various example embodiments.

FIG. 8 is a schematic plan view of at least one conductive mesh 820 electrically connected and directly connected to adjacent resistive elements 809a, 809b (collectively, resistive elements 809) by electrical connection point sets 825a, 825b (collectively, electrical connection point sets 825) according to various example embodiments. As discussed above, in some embodiments, the various elements and structures illustrated in FIG. 8 may correspond to the same or different embodiments of such elements and structures described above with respect to FIG. 4 or any other figure herein including such elements and structures. For example, the conductive mesh 820 may correspond to a different embodiment of conductive mesh 420, 520, 620, or 720 according to various embodiments. Similarly, resistive elements 809 may correspond to resistive elements 409, 509, 609, or 709 according to various embodiments. It should be noted that all such correspondences between the elements of various embodiments are not explicitly stated here, but would be obvious to one skilled in the art.

The conductive mesh 820 and resistive elements 809a, 809b may form part of a flexible circuit structure (e.g., flexible circuit structure 401, 501, 601) according to various embodiments. The conductive mesh 820 in the example embodiments of FIG. 8 includes a number of conductive segments 830 (e.g., twenty, in these illustrated embodiments, at least some called out as 830a, 830b, 830c, 830c-1, 830d, and 830c-d) providing a plurality or set of electrical pathways Q, a subset of which are labeled as reference symbols Q1, Q2, Q3, and Q4. As with electrical pathways P1-P5 in FIG. 7, the electrical pathways Q1-Q4 each may be considered all of or, a portion of, an electrical current flow path since they are illustrated as providing a continuous electrical connection. It is noted that the number of conductive segments 830 shown in FIG. 8 or otherwise herein is non-limiting. According to various example embodiments, the conductive segments 830 or the electrical pathways Q are similar or identical in form, function, or both form and function with the conductive segments described herein (e.g., conductive segments 430, 530, 630, 730 or other conductive segments described herein), or the electrical pathways P described above, respectively.

In some embodiments, the first electrical connection point set 825a includes five electrical connection points 825a1, 825a2, 825a3, 825a4, and 825a5. The second or other electrical connection point set 825b includes five electrical connection points 825b1, 825b2, 825b3, 825b4, and 825b5, according to some embodiments. The second electrical connection point set 825b does not include any electrical connection point of the first electrical connection point set 825a, according to some embodiments. In various example embodiments, an electrical pathway Q1 extending between electrical connection points 825a1 and 825b1 is provided by a single conductive segment 830a. An electrical pathway Q2 extending between electrical connection points 825a2 and 825b2 is provided by a single conductive segment 830b, according to some embodiments. An electrical pathway Q3 between electrical connection points 825a3 and 825b3 is provided by four conductive segments each labeled 830c, according to some embodiments. Electrical pathway Q4 between electrical connection points 825a3 and 825b4 is provided by seven conductive segments (e.g., one conductive segment labeled 830c-1 connected to connection point 825a3, one conductive segment labeled 830c-d, and five conductive segments labeled 830d heading to connection point 825b4), according to some embodiments. In some embodiments, a first conductive segment 830 of the conductive mesh 820 extends along a path extending from a particular electrical connection point in the first electrical connection point set 825a to a particular electrical connection point in the second electrical connection point set 825b, the path arranged to avoid intersection along the path between the first conductive segment 830 and any other one of the conductive segments 830 of the first conductive mesh 820. In the various example embodiments of FIG. 8, the path corresponding to electrical pathway Q1 extends from electrical connection point 825a1 to electrical connection point 825b1 along a single conductive segment 830a and does not intersect any conductive segment along the path Q1. Similarly, the path corresponding to electrical pathway Q2 extends from electrical connection point 525a2 to electrical connection point 825b2 along a single conductive segment 830b and does not intersect any conductive segment along the pathway Q2.

In some embodiments, at least one electrical pathway Q of the plurality of electrical pathways (e.g., Q1-Q4) does not have a conductive segment 830 in common with any other electrical pathway Q of the plurality of electrical pathways. For example, in the various example embodiments shown in FIG. 8, the electrical pathways Q1 and Q2 do not have any conductive segments 830 in common with each other or with any of various other electrical pathways Q provided by the conductive mesh 820 (e.g., Q3 and Q4). It is noted that in these various embodiments, one of the electrical pathways, such as Q1 and Q2, may receive a portion of the current previously flowing through the other of the electrical pathways, such as Q1 and Q2, should a failure occur (e.g., a crack leading to an open circuit condition) in the particular conductive segment or conductive segments 830 associated with the other of the electrical pathways, Q1 and Q2.

In some embodiments, the conductive mesh 820 electrically connects the respective adjacent pair of resistive elements 809a, 809b via a respective plurality of conductive segments 830. Each conductive segment 830 of at least some of the respective plurality of conductive segments 830 may be arranged to provide an unbranched pathway extending continuously between the first resistive element 809a and the second or other resistive element 809b of the respective adjacent pair of resistive elements 809. For example, each of single conductive segments 830a and 830b provides a respective unbranched pathway extending continuously between resistive element 809a and resistive element 809b.

In some embodiments, a first group of the plurality of conductive segments 830 of the conductive mesh 820 are arranged in a branched arrangement extending from a particular electrical connection point (e.g., electrical connection point 825a3 in the first electrical connection point set 825a) to at least two particular electrical connection points (e.g., electrical connection points 825b3, 825b4 in the second electrical connection point set 825b). In various example embodiments shown in FIG. 8, the group of conductive segments 830 (i.e., conductive segments 830c-d, 830c, and five of the six conductive segments 830d) corresponding to electrical pathways Q3 and Q4 are arranged in such a branched arrangement. It is noted in various embodiments that at least two different ones of the electrical pathways Q (e.g., at least two of the electrical pathways Q extending from different electrical connection points in the first electrical connection point set 825a or at least two of the electrical pathways Q extending to different electrical connection points in the second electrical connection point set 825b) may all pass through at least one same conductive segment (e.g., conductive segment 830c-1). In this regard, the at least one same conductive segment may be, for example, conductive segment 830c-1, and may form part of two or more different electrical pathways. For instance, each of the electrical pathways Q3 and Q4 extend or pass through a same conductive segment 830c-1 in FIG. 8.

In some embodiments, a first group of the plurality of conductive segments 830 of the conductive mesh 820 are arranged in a branched arrangement extending from a first particular electrical connection point (e.g., electrical connection point 825a3 in the first electrical connection point set 825a) to a second particular electrical connection point (e.g., electrical connection point 825b3). An example of such a branched arrangement, with respect to FIG. 8, is the group of conductive segments 830c corresponding to electrical pathway Q3, and a group of conductive segments 830 corresponding to electrical pathway Q4, but, instead, proceeding vertically up (with respect to the orientation of FIG. 8) to the right-most (with respect to the orientation of FIG. 8) intersection point 840 to re-join electrical pathway Q3 to connect to electrical connection point 825b3.

In some embodiments, each of at least some of the plurality of conductive segments 830 (e.g., conductive segment 830a or conductive segment 830b) of the conductive mesh 820 are arranged to provide a respective unbranched electrical pathway extending continuously between a first resistive element 809a of the respective adjacent pair of resistive elements 809 and a second resistive element 809b of the respective adjacent pair of resistive elements 809. In some embodiments, at least some of the plurality of conductive segments 830 of the conductive mesh 820 are arranged to provide a branched electrical pathway extending continuously between a first resistive element 809a of the respective adjacent pair of resistive elements 809 and a second resistive element 809b of the respective adjacent pair of resistive elements 809.

It is noted, according to various embodiments, that electric current flowing through an electric current flow path, which may include one or more of the electrical pathways (e.g., P, Q) provided by various ones of the conductive meshes (e.g., at least conductive meshes, 420, 520, 620, 720, 820 et cetera) described herein or otherwise within the scope of the present invention, will typically follow the path of least resistance between the respective pair of resistive elements. In this regard, typically "straight-line" arrangements of one or more of the conductive segments (e.g., conductive segments 430, 530, 630, 730, 830 et cetera) between the respective pair of resistive elements will typically provide the preferred or predominant electric current flow path for electric current flowing through the conductive mesh due to their relatively shorter lengths (i.e., the cross-sectional areas of the conductive segments set aside for ease of discussion). That is, a shorter straight-line electric current flow path connecting a respective pair of resistive elements will typically have less resistance or impedance associated with it than a longer electric current flow path (e.g., including a non-straight line electrical pathway) between the respective pair of resistive elements. Nonetheless, minor variations among the respective resistances or impedances of various ones of the conductive segments (e.g., conductive segments 430, 530, 630, 730, 830 et cetera) may cause at least some of the electric current flow paths to deviate from following straight-line electrical pathways to follow, instead non-straight line electrical pathways (e.g., electrical pathway Q4 is an example of a non-straight line electrical pathway), although the current levels in the non-straight line electrical pathways may be of lower levels than in the straight-line electrical pathways. It is understood, according to various embodiments, that a failure (e.g., a stress crack) that results in an open circuit condition in at least one of the conductive segments (e.g., conductive segments 430, 530, 630, 730, 830 et cetera) may result in a new electric current flow path, or enhance an existing electric current flow path, along another electrical pathway (e.g., a non-straight line electrical pathway such as each of electrical pathway Q4). It is further noted that a fully open circuit condition need not be developed in at least one of the conductive segments (e.g., conductive segments 430, 530, 630, 730, 830 et cetera) to result in a new electric current flow path or enhance an existing electric current flow path along another electrical pathway (e.g., a non-straight line electrical pathway such as shown by electrical pathway Q4). For example, a partial crack may develop through at least one of the conductive segments (e.g., conductive segments 430, 530, 630, 730, 830 et cetera) that does create a fully open circuit condition but creates a localized high impedance region adjacent the partial crack. If the localized high impedance region creates an impedance along the at least one conductor (e.g., conductive segments 430, 530, 630, 730, 830 et cetera) that is larger than the impedance of the at least one conductor prior to the creation of the localized high impedance region, a new electric current flow path or an enhanced existing electric current flow path may arise along another electrical pathway (e.g., a non-straight line electrical pathway such as shown by electrical pathway Q4).

Having a mix of branched electrical pathways (e.g., electrical pathways Q3, Q4 shown in FIG. 8) and non-branched electrical pathways (e.g., each of electrical pathways Q1, Q2 shown in FIG. 8) (or as described with respect to FIG. 9B, below) may be beneficial when a balance needs to be made between connection redundancy and design constraints. For example, if a region of a circuit is dense with many circuit components in a relatively small area or volume, it may be beneficial to address this density by implementing one or more unbranched connections in the dense region, because the unbranched connections typically require a smaller amount of space or volume than branched connections. However, in a relatively less dense region of a circuit, where sufficient space exists, branched connections may be desirable to provide connection redundancy.

In some embodiments, the conductive segments 830 are arranged so that each of the conductive segments 830 does not contact any other conductive segment 830 in a region spanning an edge of the resistive elements 809a, 809b of the respective adjacent pair of resistive elements 809 electrically connected by the conductive mesh 820. Such an edge of a resistive element (e.g., 809a) may be defined as a line through the connection points in the connection point set (e.g., 825a) that connects the resistive element to conductive segments 830 of the mesh 820.

It is noted that various intersection points 840 connecting various ones of the conductive segments 830 are preferably, according to various embodiments, located away from an electrode edge e.g., 815-1 of any overlapping electrode 815 to reduce the likelihood of stress cracking of the various conductive elements (e.g., conductive segments 830) due to various mechanical movements such as flexing. In some cases, various intersection points 840 where several of the segments 830 meet or connect may act as stress risers that may act as a focal point for the development of stress fractures. Likewise, as described above in this disclosure, the edge e.g., 815-1 of a relatively stiff electrode 815 may also act as a similar form of stress riser since the flexible circuit structure is prone to bend in a step-bend manner rather than in a continuous uniform curve due to the electrode having a relatively higher stiffness than an adjacent portion of the flexible circuit structure that extends outwardly from the electrode edge 815-1. In this regard, it may be advantageous to avoid combining both these stress riser effects by creating a lateral separation between the electrode edges 815-1 and the various intersection points 840, according to some embodiments.

The conductive mesh 820 may, according to various embodiments, electrically connect the respective adjacent pair of resistive elements 809a, 809b via the respective plurality of electrical pathways Q electrically connected to a respective pair of electrical connection points (e.g., a pair of connection points including a connection point from connection point set 825a and a connection point from connection point set 825b). In various embodiments, each respective pair of electrical connection points of the respective plurality of pairs of electrical connection points is different than every other pair of electrical connection points of the respective plurality of pairs of electrical connection points. For example, each of electrical pathways Q1 and Q2 extends between a respective pair of the electrical connection points (i.e., each respective pair includes an electrical connection point from the first electrical connection point set 825a and an electrical connection point from the second electrical connection point set 825b), the pair of electrical connection points associated with electrical pathway Q1 is different than the pair of electrical connection points associated with electrical pathway Q2. Specifically, in some embodiments associated with FIG. 8, electrical pathway Q1 extends from electrical connection point 825a1 to electrical connection point 825b1, and electrical pathway Q2 extends from electrical connection point 825a2 to electrical connection point 825b2. In some embodiments, at least one respective pair of electrical connection points of the respective plurality of pairs of electrical connection points includes a same electrical connection point as another respective pair of the electrical connection points of the respective plurality of pairs of electrical connection points. For example, in the example embodiments shown in FIG. 8, each of electrical pathways Q3 and Q4 extends between a respective pair of the electrical connection points (i.e., each respective pair includes an electrical connection point from the first electrical connection point set 825a and an electrical connection point from the second electrical connection point set 825b), the pair of electrical connection points associated with electrical pathway Q3 including a same electrical connection point of the pair of electrical connection points associated with electrical pathway Q4 (i.e., electrical connection point 825a3 of the first electrical connection point set 825a).

A group of electrodes 815 are shown in broken lines in FIG. 8, according to some embodiments. In some embodiments, at least some of the electrodes 815 are provided by a conductive layer other than a conductive layer that at least one of the resistive elements 809 or conductive mesh 820 are formed from or in. In some embodiments, at least some of the electrodes 815 are provided by electrically conductive layer 404a. In some embodiments, at least one nonconductive layer is located between at least one of the resistive elements 809 or conductive mesh 820 and least some of the electrodes 815. In some embodiments, a portion of each electrode 815 is positioned in an overlapping arrangement (e.g., as viewed in the plan view of FIG. 8) with a portion of at least one of the resistive elements 809. In some embodiments, a portion of each electrode 815 is positioned in an overlapping arrangement (e.g., as viewed in the plan view of FIG. 8) with a portion of conductive meshes 820. A measurement lead 810 is electrically connected to conductive mesh 820 (FIG. 8 shows another measurement lead 810 passing onto another conductive mesh (not shown), according to some embodiments). As discussed with respect to flexible circuit structure 501, such measurement lead 810 (connected to conductive mesh 820) may form at least part of a circuit to measure voltage across or current through at least the resistive element 809a or the resistive element 809b.

Figure 9B:
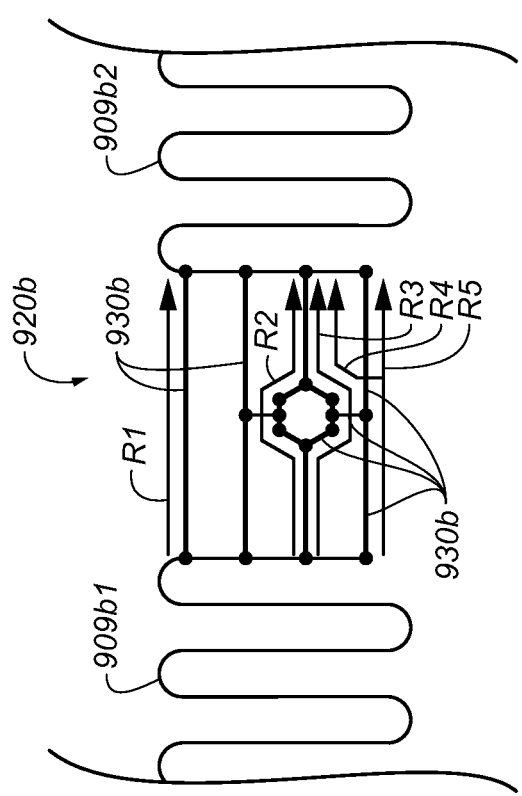
FIGS. 9A and 9B are schematic representations of conductive meshes, according to various example embodiments.
Figure 9A:
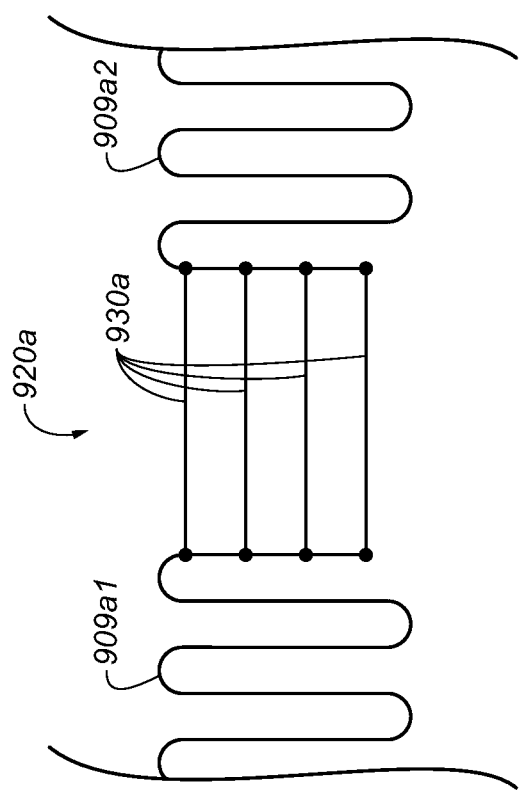

FIGS. 9A and 9B are schematic plan views of at least various conductive meshes 920a, 920b according to various example embodiments. Conductive mesh 920a, shown as per example embodiments according to FIG. 9A, electrically connects a respective pair of adjacent resistive elements 909a1, 909a2, and includes conductive segments 930a that do not intersect or otherwise meet each other in a region between a particular edge of the resistive element 909a1 and a particular edge of the resistive element 909a2 adjacent the particular edge of the resistive element 909a1. As discussed above, in some embodiments, the various elements and structures illustrated in FIGS. 9A and 9B may correspond to the same or different embodiments of such elements and structures described above with respect to FIG. 4 or any other figure herein including such elements and structures. For example, the conductive segments in FIGS. 9A, 9B may be similar or identical in form, function, or both form and function with the conductive segments (430, 530, 630, 730, 830, or other conductive segments) described herein or otherwise within the scope of the present invention according to various example embodiments. The conductive segments 930a of conductive mesh 920a terminate at electrical connection points connecting the conductive mesh 920a to the resistive elements 909a1 and 909a2 (collectively, resistive elements 909a), according to some embodiments. In FIG. 9B, the conductive mesh 920b electrically connects the respective adjacent pair of resistive elements 909b1, 909b2 (collectively, resistive elements 909b) via a respective plurality of conductive segments 930b (only some labeled in FIG. 9B for clarity). Conductive mesh 920b, shown in the example embodiment of FIG. 9B, includes conductive segments 930b that are arranged in various branched (e.g., electrical pathways R2 and R3) and unbranched arrangements (e.g., electrical pathway R1). A group of conductive segments of at least some of the respective plurality of conductive segments 930b are arranged to provide a plurality of branched electrical pathways (e.g., R2, R3 and R4, R5 in FIG. 9B) extending continuously between the first resistive element 909b1 and the second resistive element 909b2 of the respective adjacent pair of resistive elements 909b according to some embodiments. As discussed with respect to the earlier figures, because the electrical pathways R1-R5 in FIG. 9B are continuous, they may be considered electric current flow paths.

In this regard, in some embodiments, each of the unbranched or branched pathways provides a set of potential electric current flow paths between the respective adjacent pair of resistive elements. Flow of electric current through these potential electric current flow paths may be affected by the inherent impedances of each of the plurality of electrical pathways, making certain electric current flow paths more likely than others. Cracks or other defects, whether partial or complete, may change the impedance associated with a particular electrical pathway, and increase or decrease the likelihood of a particular electrical pathway providing an active electric current flow path. Cracks or other defects, whether partial or complete, may change the impedance associated with a particular electrical pathway, and alter how much electric current flows through a particular electrical pathway. In some embodiments, an active electric current flow path is a group of one or more electrical pathways through which electric current is flowing. In some embodiments, the amount of electric current flowing through an active electric current flow path is greater than a minor or parasitic amount of current flowing through inactive electric current flow paths.

In the example embodiments shown in FIG. 9A, each of the electrical pathways corresponding to conductive segments 930a of conductive mesh 920a may have a substantially similar likelihood of being active electric current flow paths in the absence of cracks or other defects in the electrical pathways. In the example embodiments shown in FIG. 9B, electrical pathway R1 may have a higher likelihood of being an active electric current flow path than electrical pathway R2. In some embodiments, both electrical pathways R1, R2 may form active electric current flow paths based on the inherent impedances associated with each of the pathways R1, R2. In some embodiments, the majority of the electric current flowing through the conductive mesh 920b may be flowing through electrical pathway R1 with only a minor amount of current flowing through electrical pathway R2. It should be noted that the conductive meshes 920a, 920b and resistive elements 909a1, 909a2, 909b1, and 909b2 may form part of a flexible circuit structure (e.g., flexible circuit structure 401, 501) according to various embodiments.

Figure 10:
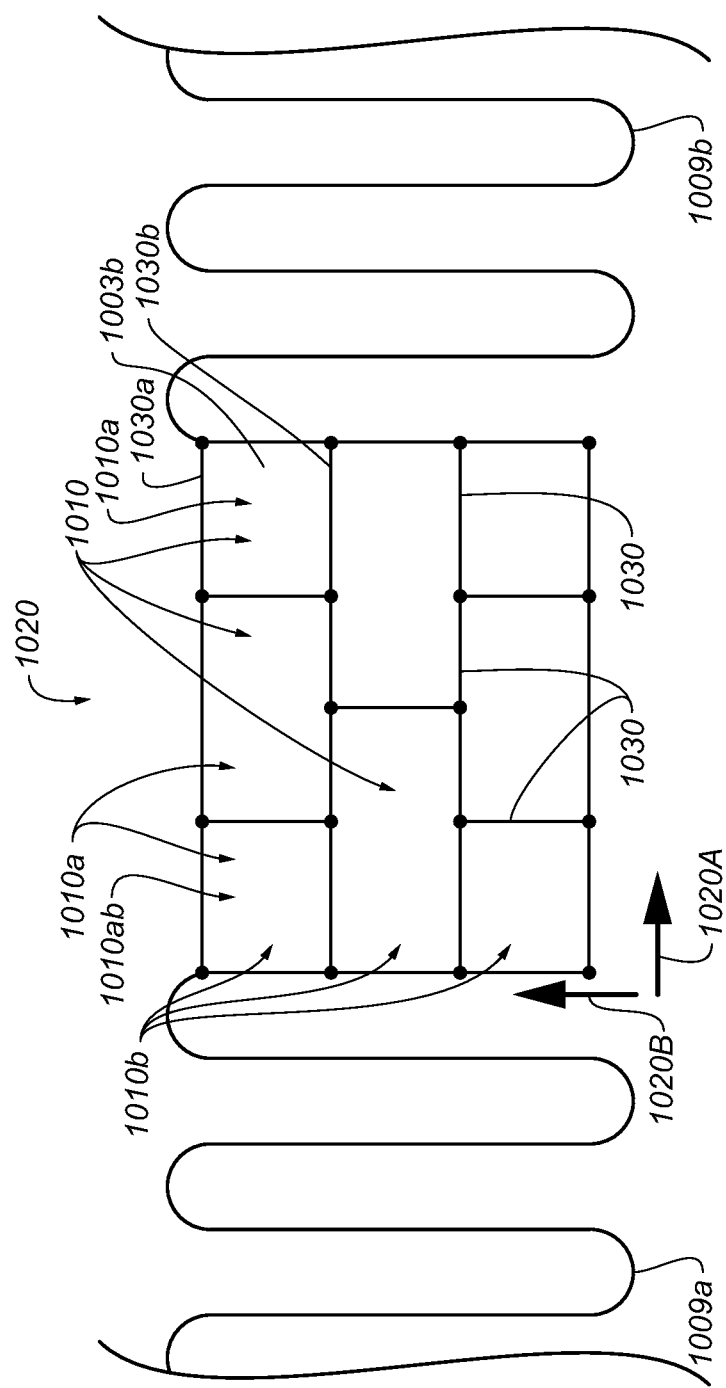
FIG. 10 is a schematic representation of a conductive mesh with openings, according to various example embodiments.

FIG. 10 shows a schematic plan view of the conductive mesh 1020 defined by a plurality of conductive segments 1030 (three called out as 1030, and two called out as 1030a, 1030b, in FIG. 10). It is noted that the number of conductive segments 1030 shown in FIG. 10 is non-limiting. As discussed above, in some embodiments, the various elements and structures illustrated in FIG. 10 may correspond to the same or different embodiments of such elements and structures described above with respect to FIG. 4 or any other figure herein including such elements and structures. For example, the conductive segments 1030 may be similar or identical in form, function, or both form and function with the conductive segments (430, 530, 630, 730, 830, 930 or other conductive segments) described herein or otherwise within the scope of the present invention according to various example embodiments. According to some embodiments, conductive mesh 1020 electrically connects a respective adjacent pair of the resistive elements 1009a, 1009b (collectively 1009) via a respective plurality of electrical pathways. Each of the electrical pathways may be provided by a respective arrangement of one or more of the conductive segments 1030 according to various embodiments (e.g., as described above with respect to FIGS. 5-9 and otherwise in this disclosure). At least a part of one electrical pathway of the plurality of electrical pathways may be prevented from merging with at least part of another electrical pathway of the plurality of electrical pathways by a region of electrically nonconductive material between the part of the one electrical pathway and the part of the another electrical pathway. For example, as shown in FIG. 10, a region 1003b of a nonconductive material, substrate, or layer (e.g., electrically nonconductive layer 403b shown in FIG. 4) on or in which at least some of the conductive segments 1030 are patterned e.g., may be located between two of the conductive segments (e.g., conductive segment 1030a and conductive segment 1030b) and separate them or prevent them from merging. The conductive mesh 1020 and resistive elements 1009a, 1009b may form part of a flexible circuit structure (e.g., at least flexible circuit structure 401, 501), according to various embodiments.

In various embodiments associated with FIG. 10, various regions between the conductive segments 1030 may form openings 1010 (three called out in FIG. 10) in the conductive mesh 1020. In some embodiments, each of the openings 1010 may include or expose a respective region of electrically nonconductive material (e.g., a region of a nonconductive material, layer, or substrate (e.g., an electrically nonconductive layer 403, such as layer 403b) on or in which at least some of the conductive segments 1030 are patterned on or in). In some embodiments, each of the openings 1010 may surround or border a respective region of electrically nonconductive material (e.g., a region 1003b of a nonconductive material (e.g., a region of electrically nonconductive layer 403b)).

In some embodiments, the conductive mesh 1020 extends along a first direction 1020A from a first resistive element 1009a toward a second resistive element 1009b. The conductive mesh 1020 may also extend along a second direction 1020B orthogonal to the first direction 1020A according to some embodiments. The openings 1010 may be arranged or arrayed along the first direction 1020A and the second direction 1020B according to various embodiments. In some embodiments, a first group of openings (e.g., at least openings 1010a) may be arranged or arrayed along the first direction 1020A and a second group of openings (e.g., at least openings 1010b) may be arranged or arrayed along the second direction 1020B. The first and the second groups of openings (e.g., openings 1010a and openings 1010b, respectively) may share at least one opening 1010ab of the plurality of openings 1010, according to some embodiments. It should be noted that the conductive mesh 1020 and resistive elements 1009a, 1009b may form part of a flexible circuit structure (e.g., at least flexible circuit structure 401, 501) according to various embodiments.

As will be described in more detail below with respect to FIGS. 11, 12, and 13, in some embodiments, a spacing between transducers (or other resistive element) of a first adjacent pair of transducers (or other resistive element) provided by a flexible circuit structure may be different than a spacing between the transducers (or other resistive element) provided by a second adjacent pair of transducers (or other resistive element) provided by a flexible circuit structure (such as any of those described herein or otherwise within the scope of the present invention). In some embodiments, the locations of various transducers, or at least a part thereof (e.g., electrodes, such as 415, 515, 615, 715, or 815 or various resistive elements such as 409, 509, 609, 709, 809, 909a, 909b, or 1009 according to various example embodiments) in the flexible circuit structure may be constrained by various functional, geometrical, or spatial constraints. For example, due to the geometry of a catheter or transducer-based device system (e.g., system 200 or 300 in FIGS. 2 and 3, respectively), it may not be possible to place electrodes 415 at certain locations of the elongate members 304. For example, at least two elongate members 304 may cross one another at in a particular crossing region. Such a crossing may prevent the placement of an electrode in the crossing region on the underlying elongate member 304. Accordingly, a larger gap between a first adjacent pair of electrodes, transducers, or other resistive elements (e.g., that span the crossing region where no electrode exists on the underlying elongate member 304 in the above example) may exist along the length of an elongate member 304 (e.g., the underlying elongate member 304 in the above example) compared to a second adjacent pair along the length (e.g., where no crossing region exists) of the elongate member 304 (e.g., the underlying elongate member 304). This increased distance between the first adjacent pair compared to the second adjacent pair (e.g., along the same elongate member 304) requires a longer than usual length of an interconnecting conductive structure, such as one or more conductive meshes (420, 520, 620, or any other conductive mesh described herein or otherwise within the scope of the present invention), to connect the first adjacent pair as compared to the second adjacent pair. This increased length may cause increased resistance, which may skew corresponding voltage or current measurements of the first adjacent pair of resistive elements. As described above, such measurements may be performed by a plurality of measurement leads (e.g., measurement leads 510 or other measurement leads described herein or otherwise within the scope of the present invention) placed between the first adjacent pair of resistive elements to appropriately measure at least the voltage across, or current through each resistive element of the first adjacent pair of resistive elements or the voltage across, or current through a portion of the interconnecting conductive structure spanning two of the measurement leads. In some embodiments, groups of the measurement leads may be connected to a conductive mesh to provide enhanced resistance to bending- or flexing-based failures as described above.

Figure 11:
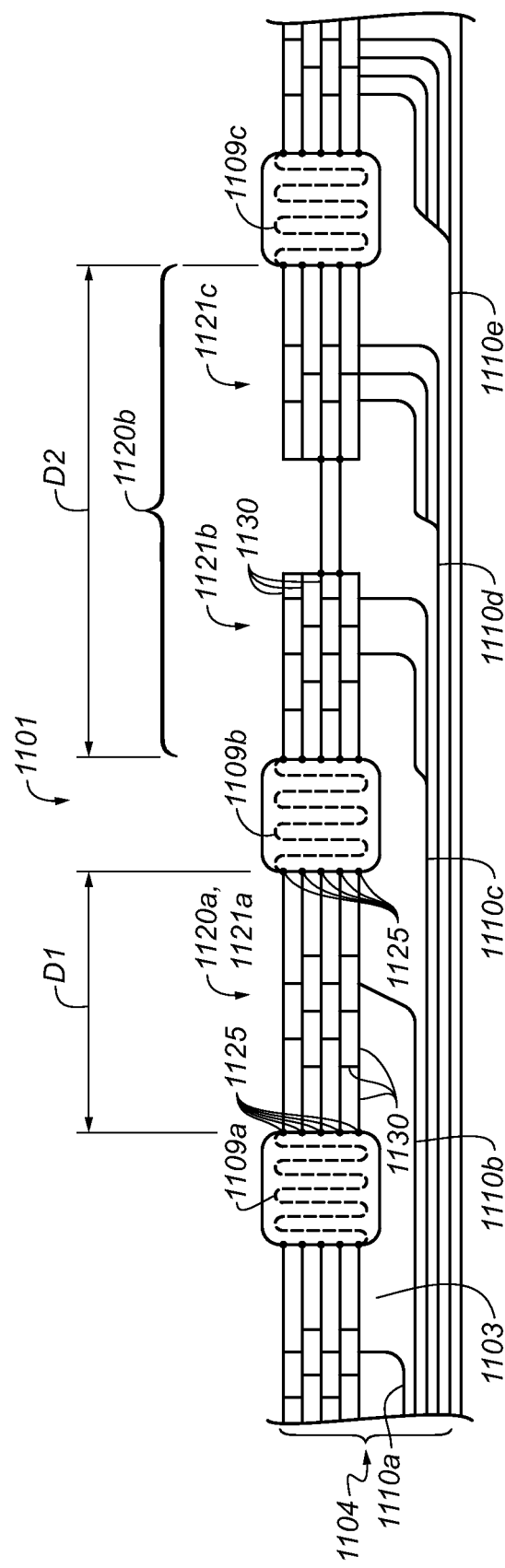
FIG. 11 is a schematic representation of a flexible circuit structure that includes a patterned conductive layer, according to various example embodiments.

FIGS. 11, 12, and 13 illustrate, among other things, various embodiments of the above-discussed differences in resistive element spacing. In this regard, FIGS. 11, 12, and 13 show schematic plan views of a flexible circuit structure 1101, 1201, 1301, respectively, according to various example embodiments. As discussed above, in some embodiments, the various elements and structures illustrated in FIGS. 11, 12, and 13 may correspond to the same or different embodiments of such elements and structures described above with respect to FIG. 4 or any other figure herein including such elements and structures. For example, in some example embodiments, the various elements and structures described above with respect to each of flexible circuit structures 401, 501, and 601 may correspond to the respective elements and structures of flexible circuit structures 1101, 1201, 1301. For example, each of flexible circuit structures 1101, 1201, 1301 may exhibit at least part of the alternating conductive/nonconductive layering (404/403) structure shown in FIG. 4, even though such a structure may not be apparent from the plan view of FIGS. 11, 12, and 13. (The same applies for flexible circuit structures 501 and 601, as well as the devices of FIGS. 7, 8, 9A, 9B, and 10.) For another example, the electrical-connection-arrangements 1120, 1220, 1320 may correspond to conductive meshes 420, 520, 620, 720, 820, 920, and 1020 according to various embodiments. Similarly, for yet another example, the electrical loads 1109, 1209, 1309 may correspond to resistive elements 409, 509, 609, 709, 809, 909a, 909b, and 1009 according to various embodiments.

FIG. 11 is a schematic plan view of a flexible circuit structure 1101 that includes at least an electrically conductive flexible circuit layer 1104 formed of electrically conductive material. The electrically conductive flexible circuit layer 1104 is provided at least proximate to, formed on or in, or supported directly or indirectly by a flexible nonconductive layer 1103. In some embodiments, the flexible circuit structure 1101 includes a plurality of electrical loads 1109 (three called out in FIG. 11 as reference symbols 1109a, 1109b and 1109c). In some embodiments, the electrically conductive layer is patterned to provide a plurality of electrical loads 1109 (three called out in FIG. 11 as reference symbols 1109a, 1109b and 1109c). The electrical loads 1109 are electrically connected in series by a plurality of electrical-connection-arrangements 1120 (two called out in FIG. 11 as reference symbols 1120a and 1120b) according to various embodiments. Each electrical-connection-arrangement 1120 electrically connects a respective adjacent pair of electrical loads 1109 together according to some embodiments. In some embodiments, each electrical-connection-arrangement 1120 directly connects each electrical load 1109 of a respective adjacent pair of electrical loads 1109 via two or more electrical connection points 1125 (ten called out in FIG. 11). A plurality of measurement leads 1110 (five called out in FIG. 11 as reference symbols 1110a, 1110b, 1110c, 1110d and 1110e) are each electrically connected to at least one of the plurality of electrical loads 1109 (e.g., via electrical connection arrangement 1120) according to some embodiments. In some embodiments, the measurement leads 1110 are employed to measure voltage across various ones of the loads and may be also referred to as electrical-load-voltage-measurement leads 1110. In some embodiments, the measurement leads 1110 are employed to measure current flowing through various ones of the loads and may be also referred to as electrical-load-current-measurement leads 1110. Each of the measurement leads 1110 may be directly connected to a respective electrical-connection-arrangement 1120 according to various embodiments. It is noted that the respective numbers of electrical loads 1109, electrical-connection-arrangement 1120, measurement leads 1110 and electrical connection points 1125 shown in FIG. 11 is non-limiting.

Flexible circuit structure 1101 may include arrangements where adjacent pairs of electrical loads 1109 may be separated by varying distances. In some embodiments, a first electrical-connection-arrangement 1120a of the plurality of electrical-connection-arrangements 1120 spans a first distance D1 between the first respective adjacent pair of electrical loads 1109*a*, 1109*b* of the plurality of electrical loads 1109. A second electrical-connection arrangement 1120*b* of the plurality of electrical-connection-arrangements spans a second distance D2 between a second respective adjacent pair of electrical loads 1109*b*, 1109*c* of the plurality of electrical loads 1109. In some embodiments, the first distance D1 and the second distance D2 are different. In some embodiments, the second distance D2 is greater than the first distance D1. In some embodiments, the first electrical-connection-arrangement 1120*a* is electrically connected to a first set of one or more of the plurality of measurement leads 1110 and the second electrical-connection-arrangement 1120*b* is electrically connected to a second set of one or more of the plurality of measurement leads 1110. In some embodiments, the first set of measurement leads 1110 may have a different number of leads than the second set of measurement leads 1110. For example, in FIG. 11, the first electrical-connection-arrangement 1120*a* is electrically connected and directly connected to measurement lead 1110*b*, and the second electrical-connection-arrangement 1120*b* is electrically connected and directly connected to a greater number of the measurement leads 1110 than the number of the plurality of measurement leads 1110 connected to by the first electrical-connection-arrangement 1120*a*. In some embodiments, the first electrical-connection-arrangement 1120*a* is electrically connected and directly connected to one of the plurality of measurement leads 1110 (e.g., measurement lead 1110*b*) and the second electrical-connection-arrangement 1120*b* is electrically connected to a greater number of the plurality of electrical-load-voltage-measurement leads (e.g., measurement leads 1110*c*, 1110*d*) than the number of the plurality of measurement leads 1110 connected to by the first electrical-connection-arrangement 1120*a*. It is noted that various ones of the measurement leads 1110 may have a branched structure. For example, measurement lead 1110*c* includes two branched portions, each of the two branched portions directly connected and electrically connected to electrical-connection-arrangement 1120*b* (e.g., via conductive mesh 1121*b*), and measurement lead 1110*d* includes three branched portions, each of the three branched portions directly connected and electrically connected to electrical-connection-arrangement 1120*b* (e.g., via conductive mesh 1121*c*).

In some embodiments, the first electrical-connection-arrangement 1120*a* is electrically connected to a first measurement lead set including at least one of the plurality of measurement leads 1110 and the second electrical-connection-arrangement 1120*b* is electrically connected to a second measurement lead set comprising at least two of the plurality of measurement leads 1110. The second measurement lead set may have a greater number of measurement leads 1110 than the first measurement lead set according to various embodiments.

The electrical-connection-arrangements 1120 may have an inherent electrical resistance provided by the conductive material of the electrical-connection-arrangements 1120. In some embodiments, the electrical resistance of the second electrical-connection-arrangement 1120*b* is greater than the electrical resistance of the first electrical-connection-arrangement 1120*a*, due at least to the longer length D2 of the second electrical-connection-arrangement 1120*b* as compared to the length D1 of the first electrical-connection-arrangement 1120*a*. The resistance of a particular electrical conductor is typically directly proportional to a length of the electrical conductor and inversely proportional to a cross-sectional area of the electrical conductor (i.e., the cross-section as viewed in a direction of the electric current flow in the electrical conductor). Accordingly, in various embodiments in which the first electrical-connection-arrangement 1120*a* and the second electrical-connection-arrangement 1120*b* are provided by various patterned electrical conductive structures, the relatively longer length of the second electrical-connection-arrangement 1120*b* required to span the distance D2 will typically cause the second electrical-connection-arrangement 1120*b* to have a greater electrical resistance than the electrical resistance of the "relatively shorter" first electrical-connection-arrangement 1120*a* which spans distance D1.

In some embodiments, at least one of the electrical-connection-arrangements 1120 may include one or more conductive meshes 1121 (three called out in FIG. 11 as reference symbols 1121*a*, 1121*b* and 1121*c*). The conductive meshes 1121 may include a plurality of conductive segments 1130 (six called out in FIG. 11) spatially arranged to provide a plurality of electrical pathways defining a respective portion of an electric current flow path between the electrical loads of a respective adjacent pair of electrical loads 1109 in a manner similar to or identical to that of the conductive segments of various ones of the conductive meshes described earlier in this disclosure. Each conductive segment of the plurality of conductive segments provides a respective portion of the plurality of electrical pathways.

The first and the second electrical-connection-arrangements 1120*a*, 1120*b* may include different numbers of conductive meshes 1121 as per various example embodiments. For example, the first electrical-connection-arrangement 1120*a* includes one conductive mesh 1121*a* and the second electrical-connection-arrangement 1120*b* includes two conductive meshes 1121*b* and 1121*c* in FIG. 11, according to some embodiments. In some embodiments, a total of the conductive meshes 1121 comprised by the second electrical-connection-arrangement 1120*b* is greater than a total of the conductive meshes 1121 comprised by the first electrical-connection-arrangement 1120*a*. In some embodiments, each conductive mesh 1121 is directly connected and electrically connected to at least a respective one of the plurality of measurement-leads 1110. For example, the first conductive mesh 1121*a* is directly connected to the measurement lead 1110*b*, the second conductive mesh 1121*b* is directly connected to the measurement lead 1110*c*, and the third conductive mesh 1121*c* is directly connected to the measurement lead 1110*d* in FIG. 11. In some embodiments, there is a difference between electrically connected and directly connected. For example, resistive element 1109*a* is electrically connected to resistive element 1109*b* through the first electrical-connection-arrangement 1120*a*. However, resistive element 1109*a* is not directly connected to resistive element 1109*b* as they do not share a common electrical connection point. In contrast, resistive element 1109*a* is electrically and directly connected to the first electrical-connection-arrangement 1120*a* through the plurality of electrical connection points shared by the resistive element 1109*a* and the first electrical-connection-arrangement 1120*a*.

Directly connecting, electrically connecting, or both directly and electrically connecting a set of the measurement leads 1110 to one of the electrical-connection-arrangements 1120 (e.g., second electrical-connection-arrangement 1120*b* in FIG. 11) may be motivated by various reasons according to some embodiments. For example, a voltage across a particular one of the electrical loads 1109, or a current flowing through a particular one of the electrical loads 1109, may be measured by a respective pair of the measurement leads 1110, the particular one of the electrical loads 1109 positioned between the measurement leads of the respective pair of the measurement leads 1110. To simplify the measurement circuitry, successive pairs of the measurement leads 1110 may share a common measurement lead 1110 located between a respective adjacent pair of electrical loads 1109. For example, according to some embodiments associated with FIG. 11, a first pair of measurement leads 1110a and 1110b are electrically connected to electrical load 1109a to measure a voltage thereacross, and a second pair of measurement leads 1110b, 1110c are electrically connected to electrical load 1109b (i.e., adjacently located to electrical load 1109a) to measure a voltage thereacross, the first and the second pairs of measurement leads including a same measurement lead (i.e., measurement lead 1110b). This architecture may be particularly effective when the resistance or impedance associated with a respective connection arrangement between each measurement lead of the pair of the measurement leads 1110 and the respective electrical load 1109 is sufficiently low so as to not increase measurement errors beyond acceptable bounds in the measured voltage across the respective electrical load 1109. It is noted that each measurement lead of the pair of measurement leads 1110 may be electrically coupled via a portion of a respective electrical-connection-arrangement 1120 to the corresponding or respective electrical load 1109. For example, in FIG. 11, measurement lead 1110b is electrically connected to electrical load 1109a via a portion of electrical-connection-arrangement 1120a. Accordingly, if the resistance or impedance of an electrical-connection-arrangement 1120 between two adjacent ones of the electrical loads 1109 is relatively high (e.g., 5% or greater than the resistance or impedance of each at least one of the adjacent electrical loads 1109 according to some embodiments; 2% or greater than the resistance or impedance of each at least one of the adjacent electrical loads 1109 according to other embodiments; or 1% or greater than the resistance or impedance of each at least one of the adjacent electrical loads 1109 according to yet other embodiments), the use of a common or shared measurement lead 1110 between the adjacent electrical loads 1109 may not be appropriate. In this regard, a plurality of measurement leads (e.g., the pair of measurement leads 1110c and 1110d) may be employed between the adjacent pair of the electrical loads to reduce potential error causing factors that may be associated with the electrical-connection-arrangement 1120 therebetween. Again, it is noted that an electrical-connection-arrangement 1120 may have a relatively high associated resistance or impedance when it is required to span a relatively large distance (e.g., D2) between the respective two adjacent electrical loads 1109.

It is noted that, in FIG. 11 the use of various ones of the conductive meshes 1121 may be employed to mitigate or reduce various failure modes induced by, for example, stress-induced cracking as described in this disclosure, in some example embodiments.

It is also noted that, in FIG. 11, a reduced or more minimal conductive segment arrangement may be provided to connect conductive meshes 1121b, 1121c and span a gap lacking a resistive element between them. In FIG. 11, two parallel straight conductive segments are illustrated as connecting conductive meshes 1121b, 1121c, and these two conductive segments exhibit less complexity than each of the conductive meshes 1121b, 1121c. Such an arrangement may be beneficial due to particular design constraints (e.g., presence of other circuit elements). By providing two parallel straight conductive segments (instead of, for example, one straight conductive segment) between conductive meshes 1121b, 1121c, as shown in FIG. 11, some level of redundancy and failure tolerance can be provided. It should be noted that the invention is not limited to the conductive segment arrangement shown between conductive meshes 1121b, 1121c in FIG. 11, and alternate implementations may be provided, such as non-straight conductive segments, or more or less than one conductive segment. In some embodiments, a reduced or minimal conductive segment arrangement is not provided between separated conductive meshes (e.g., meshes 1121b and 1121c) and, instead, a single, longer mesh is provided to span the gap lacking the resistive element (e.g., meshes 1121b and 1121c may extended so as to join each other).

In some embodiments, the nonconductive flexible layer 1103 may be part of a plurality of nonconductive flexible layers 1103, and the conductive flexible circuit layer 1104 may form part of a plurality of conductive flexible circuit layers that are interleaved with the plurality of electrically nonconductive flexible layers 1104 as described with respect to various other example embodiments in this disclosure.

In some embodiments, the plurality of electrical loads 1109 may be temperature sensors (e.g., provided at least in part by resistive elements such as resistive elements 409, 509 609, 709, 809, 909, or 1009) and, as described above with respect to FIG. 6, at least the first electrical-connection-arrangement 1120a or the second electrical-connection-arrangement 1120b may electrically connect at least a respective adjacent pair of temperature sensors by at least one via (discussed above, e.g., with respect to FIG. 6) arranged to electrically connect different ones of the plurality of conductive flexible circuit layers 1104. In some embodiments, the first electrical-connection arrangement 1120a electrically connects the respective adjacent pair of temperature sensors corresponding to the first electrical load 1109a and the second electrical load 1109b. In some embodiments, the electrical load 1109 of the plurality of electrical loads 1109 is provided at least in part by a respective one of the plurality of temperature sensors.

FIG. 12 is a schematic plan view of a flexible circuit structure 1201 that includes at least an electrically conductive flexible layer 1204 formed of electrically conductive material. The electrically conductive flexible circuit layer 1204 is provided at least proximate to, formed on or in, or supported directly or indirectly by a flexible nonconductive layer 1203. In some embodiments, the flexible circuit structure 1201 includes a plurality of electrical loads 1209 (three called out in FIG. 12 as reference symbols 1209a, 1209b and 1209c). In some embodiments, the electrically conductive layer 1204 is patterned to provide a plurality of electrical loads 1209 (three called out in FIG. 12 as reference symbols 1209a, 1209b, and 1209c). The electrical loads 1209 are electrically connected in series by a plurality of electrical-connection-arrangements 1220 (four called out in FIG. 12 as reference symbols 1220a, 1220b, 1220c and 1220d), according to various embodiments. Each electrical-connection-arrangement 1220 electrically connects a respective adjacent pair of electrical loads 1209 together, according to some embodiments. In some embodiments, the flexible circuit structure 1201 includes a plurality of measurement leads 1210 (five called out in FIG. 12 as 1210a, 1210b, 1210c, 1210d and 1210e), each electrically connected to at least one of the plurality of electrical loads 1209 (e.g., via an electrical-connection-arrangement 1220) according to some embodiments. In some embodiments, at least some of the measurement leads 1210 are employed to measure voltage across at least one of the loads and may be also referred to as electrical-load-voltage-measurement leads 1210. In some embodiments, at least some of the measurement leads 1210 are employed to measure current flowing through at least one of the loads and may be also referred to as electrical-load-current-measurement leads 1210. Each of the measurement leads 1210 may be directly connected to a respective electrical-connection-arrangement 1220, according to various embodiments. In various embodiments, voltage across each of at least some of the electrical loads 1209 is sensed or measured at least in part by a respective pair of the measurement leads 1210. It is noted that the respective numbers of electrical loads 1209, electrical-connection-arrangement 1220, and measurement leads 1210 shown in FIG. 12 is non-limiting.

In some embodiments, the flexible circuit structure 1201 includes (e.g., the conductive flexible layer 1204 may be patterned to include) an electric-serial-circuitry-connection-arrangement including a serial-electrical-connection order of first measurement lead 1210a, first electrical load 1209a, second measurement lead 1210b, third measurement lead 1210c, second electrical load 1209b, fourth measurement lead 1210d, third electrical load 1209c, and fifth measurement lead 1210e.

In some embodiments, the electrical-connection-arrangement 1220b spans a first distance E1 between first electrical load 1209a and the second electrical load 1209b. The electrical-connection-arrangement 1220c spans a second distance E2 between second electrical load 1209b and the third electrical load 1209c. In some embodiments, the first distance E1 between the first electrical load 1209a and the second electrical load 1209b is greater than second distance E2 between the second electrical load 1209b and the third electrical load 1209c. In some embodiments, the first measurement lead 1210a and the second measurement lead 1210b are positioned to sense voltage across the first electrical load 1209a. In some embodiments, the third measurement lead 1210c and the fourth measurement lead 1210d are positioned to sense voltage across the second electrical load 1209b. In some embodiments, the fourth measurement lead 1210d and the fifth measurement lead 1210e are positioned to sense voltage across the third electrical load 1209c.

The arrangement of FIG. 12 (as well as the arrangement of FIG. 13, below), where the earlier-described conductive meshes are not provided between resistive elements, may be beneficial in some embodiments, because such arrangement may facilitate more accurate measurement or sensing of the resistive elements (e.g., 1209a, 1209b, 1209c), as compared to embodiments which have more complex connection arrangements. In this regard, some embodiments such as those illustrated in FIG. 12 (and FIG. 13, discussed below), may be preferable when fault tolerance of electrical-connection-arrangements 1220 is less of a concern. Of course, the electrical-connection-arrangements 1220 (and 1320 in FIG. 13, discussed below) may be replaced with a conductive mesh arrangement, for example, as described above, according to some embodiments.

FIG. 13 shows a schematic plan view of a flexible circuit structure 1301 that includes at least an electrically conductive flexible layer 1304 formed of electrically conductive material. The electrically conductive flexible circuit layer 1304 is provided at least proximate to, formed on or in, or supported directly or indirectly by a flexible nonconductive layer 1303. In some embodiments, the flexible circuit structure 1301 includes a plurality of electrical loads 1309 (three called out in FIG. 13 as reference symbols 1309a, 1309b and 1309c). In some embodiments, the electrically conductive layer 1304 is patterned to provide a plurality of electrical loads 1309 (three called out in FIG. 13 as reference symbols 1309a, 1309b and 1309c). The electrical loads 1309 are electrically connected in series by a plurality of electrical-connection-arrangements 1320 (four called out in FIG. 13 as reference symbols 1320a, 1320b, 1320c and 1320d) according to various embodiments. Each electrical-connection-arrangement 1320 electrically connects a respective adjacent pair of electrical loads 1309 together according to some embodiments. In some embodiments, the flexible circuit structure 1301 includes a plurality of measurement leads 1310 (five called out in FIG. 13 as 1310a, 1310b, 1310c, 1310d and 1310e), each electrically connected to at least one of the plurality of electrical loads 1309 (e.g., via an electrical-connection-arrangement 1320) according to some embodiments. In some embodiments, at least some of the measurement leads 1310 are employed to measure voltage across at least one of the loads and may be also referred to as electrical-load-voltage-measurement leads 1310. In some embodiments, at least some of the measurement leads 1310 are employed to measure current flowing through at least one of the loads and may be also referred to as electrical-load-current-measurement leads 1310. Each of the measurement leads 1310 may be directly connected to a respective electrical-connection-arrangement 1320 according to various embodiments. In various embodiments, voltage across each of at least some of the electrical loads 1309 is sensed or measured at least in part by a respective pair of the measurement leads 1310. It is noted that the respective numbers of electrical loads 1309, electrical-connection-arrangement 1320, and measurement leads 1310 shown in FIG. 13 is non-limiting.

In some embodiments, a first pair of leads 1310a, 1310b of the plurality of measurement leads 1310 is positioned to sense voltage across the first electrical load 1309a of the plurality of electrical loads 1309. A second pair of leads 1310b, 1310c of the plurality of measurement leads 1310 is positioned to sense voltage across the second electrical load 1309b of the plurality of electrical loads 1309. A third pair of leads 1310d, 1310e of the plurality of measurement leads 1310 is positioned to sense voltage across the third electrical load 1309c of the plurality of electrical loads 1309.

In some embodiments, the first electrical load 1309a is adjacent to the second electrical load 1309b in the series and the second electrical load 1309b and the third electrical load 1309c are adjacent in the series. According to some embodiments, the first pair of leads 1310a, 1310b and the second pair of leads 1310b, 1310c include a same lead 1310b of the plurality of measurement leads 1310. According to some embodiments, the second pair of leads 1310b, 1310c does not include any of the plurality of measurement leads 1310 of the third pair of leads 1310d, 1310e.

In some embodiments, a distance F1 spanning the first electrical load 1309a and the second electrical load 1309b is different than a distance F2 spanning the second electrical load 1309b and the third electrical load 1309c. In some embodiments, the distance F2 spanning the second electrical load 1309b and the third electrical load 1309c is greater than the distance F1 spanning the first electrical load 1309a and the second electrical load 1309b. In some embodiments, a distance F1 separating the first electrical load 1309a from the second electrical load 1309b is different than a distance F2 separating the second electrical load 1309b from the third electrical load 1309c. In some embodiments, the distance F2 separating the second electrical load 1309b from the third electrical load 1309c is greater than the distance F1 separating the first electrical load 1309a from the second electrical load 1309b.

In some embodiments, an electrical resistance of a conductive portion (e.g., electrical-connection-arrangement 1320b) of the flexible circuit structure 1301 that serially electrically connects the first electrical load 1309a to the second electrical load 1309b is different than an electrical resistance of a conductive portion (e.g., electrical-connection-arrangement 1320c) of the flexible circuit structure 1301 that serially electrically connects the second electrical load 1309b to the third electrical load 1309c. In some embodiments, the electrical resistance of the conductive portion of the flexible circuit structure 1301 that serially electrically connects the second electrical load 1309b to the third electrical load 1309c is greater than the electrical resistance of the conductive portion of the flexible circuit structure 1301 that serially electrically connects the first electrical load 1309a to the second electrical load 1309b. For example, in various embodiments, the conductive portion of the flexible circuit structure 1301 that serially electrically connects the second electrical load 1309b to the third electrical load 1309c may be provided by a patterned electrical conductive structure that has a relatively longer length in order to span the distance F2 and will thereby typically cause the portion of the flexible circuit structure that serially electrically connects the second electrical load 1309b to the third electrical load 1309c to have a greater electrical resistance than the electrical resistance of the "relatively shorter" conductive portion of the flexible circuit structure 1301 that serially electrically connects the first electrical load 1309a to the second electrical load 1309b over the relatively shorter distance F1. In some embodiments, each of at least some of the conductive portions of the flexible printed circuit structure 1301 that serially electrically connect the members of a respective adjacent pair of the electrical loads 1309 is provided by a single conductive segment.

In some embodiments, the conductive portions of the flexible printed circuit structure 1301 that serially electrically connect the members of a respective adjacent pair of the electrical loads 1309 are each provided by a respective one of the electrical-connection-arrangements 1320 that at least directly connect, electrically connect, or both directly and electrically connect the respective adjacent pair of electrical loads 1309 of the plurality of electrical loads.

Although each of FIGS. 12 and 13 illustrates electrical-connection-arrangements 1220, 1320 as single connection lines or electrical pathways, such electrical-connection-arrangements may instead take the form of, or include, any conductive mesh described herein (e.g., 420, 520, 620, 720, 820, 920, 1020, or 1120) or otherwise within the scope of the present invention. In this regard, at least some of the plurality of electrical-connection-arrangements 1220, 1320 may include a set of one or more conductive meshes, each conductive mesh including a plurality of conductive segments spatially arranged to provide a plurality of electrical pathways defining a respective portion of an electric current flow path between the electrical loads (e.g., 1209, 1309) of a respective adjacent pair of electrical loads. Each conductive segment may provide a respective portion of the plurality of electrical pathways. Each of at least some of conductive meshes may be directly connected to one or more of the plurality of measurement leads (e.g., 1210, 1310) according to some example embodiments.

Figure 16:
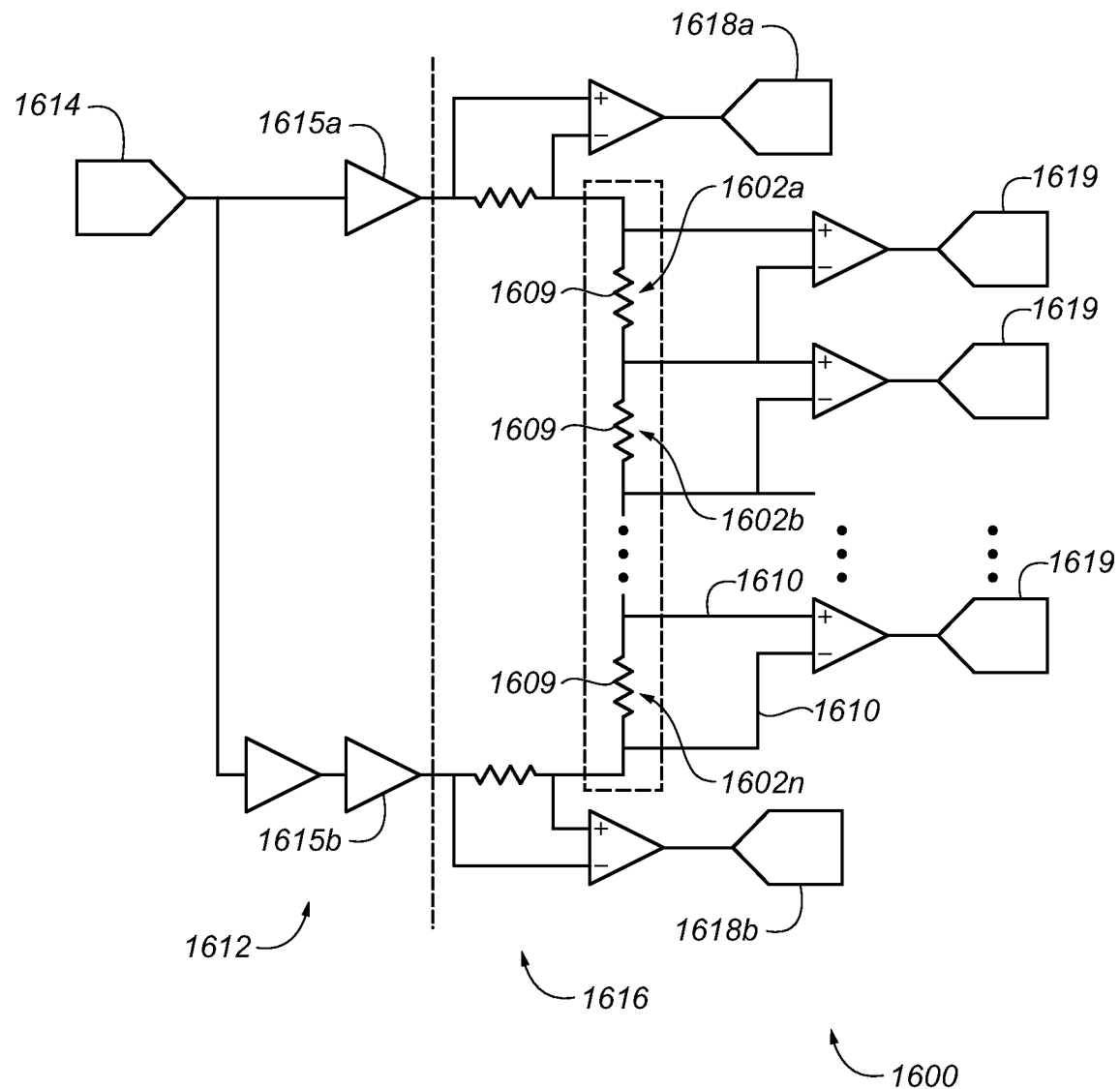
FIG. 16 is a block diagram of an electrical circuit configured to determine an electrical resistance of various resistive elements employed by various transducers according to some embodiments.

FIG. 16 is a block diagram of an electrical circuit 1600 that is at least configured to measure or determine voltage or current, according to some embodiments. Such a circuit 1600 may be incorporated into the medical device system of FIG. 1, 3A, or 3B, or more particularly, into a transducer-based device system (e.g., 200 or 300), and connected to the various measurement leads 1610, such as those described herein (e.g., 410, 510, 610, 710, 810, 1110, 1210, 1310) or otherwise within the scope of the present invention. As discussed above, the resistive elements (e.g., 1609), transducers 1602, and other structures of FIG. 16 may correspond to the same or different embodiments of such elements and structures described above with respect to FIG. 4 or any other figure herein including such elements and structures, according to some embodiments.

Electrical circuit 1600 is configured, according to some embodiments, to determine an electrical resistance of various resistive elements 1609 employed by various transducers (e.g., FIG. 4) 1602a, 1602b, . . . 1602n (collectively 1602) which may be positioned in a bodily cavity (e.g., left atrium 204) including one or more ports (e.g., pulmonary vein ostia or a mitral valve 226) in fluid communication with the bodily cavity. In some embodiments, a portion (e.g., an electrode surface or a portion thereof) of a first transducer 1602 may be positioned in contact with non-fluidic tissue (e.g., cardiac tissue) while a portion (e.g., an electrode surface or a portion thereof) of a second transducer 1602 may be in contact with fluidic tissue (e.g., blood). The number of transducers 1602 employed may vary in different embodiments.

Each resistive element 1609 may be formed from copper traces on a flexible printed circuit board substrate (e.g., resistive elements 409, 509, 609, 709, 809, 909, 1009, 1109, 1209, 1309), or resistive elements provided on a structure. Each transducer 1602 is driven by a state machine within a controller (e.g., controller 324), according to some embodiments. In various embodiments, electrical circuit 1600 includes a signal source device system 1612 and a sensing device system 1616, each schematically distinguished from one another by a broken line in FIG. 16. It is understood that one or both of signal source device system 1612 and sensing device system 1616 may each include different circuitry than those shown in FIG. 16. In various embodiments, signal source device system 1612 provides various input signals to at least some of the transducers 1602 during a temperature sensing mode. In some embodiments, signal source device system 1612 provides various input signals to at least some of the transducers 1602 during a flow sensing mode (described below). In some example embodiments, signal source device system 1612 provides various input signals to each of the transducers 1602 during a mapping mode in which information specifying a location of various anatomical features within a bodily cavity is generated (e.g., by convective cooling of heated transducer elements by fluid as described above in this disclosure). Information specifying a location of each of one or more regions of an interior tissue surface within a bodily cavity may be provided along with information specifying a location of each of at least one of one or more ports on the interior tissue wall with respect to the one or more regions during the mapping mode. In some example embodiments, signal source device system 1612 provides various input signals to each of the transducers 1602 during a tissue contact mode in which assessment of contact or an amount of contact between a portion (e.g., an electrically conductive surface portion of an electrode) of each of the various transducers 1602 and non-fluidic tissue or a fluidic tissue is made. In some example embodiments, signal source device system 1612 provides various input signals during an ablation mode. In some example embodiments, a state machine in the controller (e.g., controller 324) may be employed to cause various control signals to be provided to signal source device system 1612 to configure electrical circuit 1600 in at least one of a temperature sensing mode and a flow sensing mode. In some example embodiments, signal source device system 1612 includes a radio-frequency generator configured to transfer energy to, or from, the tissue wall. In some example embodiments, the radio-frequency generator is arranged to provide a varying electric current to at least one of the transducers 1602 to provide energy to tissue from the at least one of the transducers 1602.

In various embodiments, digital-to-analog converter (DAC) 1614 generates an input signal that is amplified and is driven across the series of the connected resistive elements 1609 during a temperature sensing mode. Amplifiers including driver 1615a and driver 1615b are arranged to produce a balanced output across the series of connected resistive elements 1609. Electric current driven through resistive elements 1609 is sampled by sensing device system 1616. In this example embodiment, electric current driven through resistive elements 1609 is sampled in series with each of the drivers 1615a, 1615b via respective ones of analog-to-digital converters (ADC) 1618a, 1618b. It is noted that sensing the electric current at each of the drivers 1615a, 1615b can allow the system to detect possible failures that may result in the electric current leaking through another path. Voltage across each of the resistive elements 1609 is also sampled by sensing device system 1616 via respective ones of analog-to-digital converters (ADC) 1619 (three called out in FIG. 16). In some embodiments, the current and voltage measurements are sampled synchronously with the input signal and the demodulation of each measurement is computed by the controller. Electrical circuit 1600 allows for the electrical resistance of each of the resistive elements 1609 to be precisely determined. The resistance of an electrically conductive metal (e.g., copper) changes based on the temperature of the electrically conductive metal. The rate of change is denominated as a temperature coefficient of resistance (TCR). The resistance of various ones of the resistive elements 1609 may be related to the temperature of the resistive element 1609 by the following relationship:

$R=R_0*[1+TCR*(T-T_0)]$, where:

R is a resistance of the electrically conductive metal at a temperature T;

$R_0$ is a resistance of the electrically conductive metal at a reference temperature $T_0$;

TCR is the temperature coefficient of resistance of the electrically conductive metal for the reference temperature (i.e., the TCR for copper is 4270 ppm at $T_0=0°$ C.); and T is the temperature of the electrically conductive metal.

When signal source device system 1612 applies energy to a resistive element (e.g., resistive element 1609 employed by various transducers 1602) positioned within a medium having relatively high flow conditions (e.g., when subjected to blood flow conditions proximate a pulmonary vein port in the left atrium of a heart or when not shielded from the flow by contact with non-fluidic tissue), the resistive element will reach a lower temperature and will settle more quickly than if the resistive element were positioned within a medium having relatively low flow conditions (e.g., when positioned proximate, or in contact with a region of a non-fluidic tissue surface within a left atrium positioned away from a pulmonary vein port). Likewise, when the signal source ceases to apply energy, the resistive element positioned within a medium having relatively high flow conditions will cool faster and will return to ambient temperature faster than if the resistive element were to be within a medium having relatively lower flow conditions. When the signal source repetitively applies and ceases to apply energy to the resistive element, the resulting temperature changes of the resistive element positioned in a medium having relatively low flow conditions will appear to have a phase delay compared to the resulting temperature changes of the resistive element when positioned in a medium having relatively higher flow conditions.

In various embodiments, flow sensing is provided by electrical circuit 1600 by determining the rate of convective cooling at various ones of the resistive elements 1609. In some embodiments, when the flow sensing mode is enabled, various ones of the resistive elements 1609 whose temperature is determined during the temperature sensing mode may also be employed to deliver energy (i.e., heat) during the flow sensing mode. In various embodiments, the energy is delivered using the same drivers 1615a, 1615b employed in the temperature sensing mode. It is understood that additional and or alternate drivers may be employed in other example embodiments but with additional cost and complexity. When the temperature sensing mode is not active, the controller system may continue to drive an input signal to each of the resistive elements 1609 in various embodiments. In some embodiments, the temperature sensing mode is employed to sense temperature at least during an ablation mode in which tissue proximate at least a particular one of the resistive elements 1609 is ablated.

Subsets or combinations of various embodiments described above provide further embodiments.

These and other changes may be made to various embodiments in light of the above-detailed description. In general, in the following claims, the terms used should not be construed to limit the invention to the specific embodiments disclosed in the specification and the claims, but should be construed to include other transducer-based device systems including all medical treatment device systems and all medical diagnostic device systems in accordance with the claims. Further, it should be noted that, although several of the above-discussed embodiments are described within the context of an intra-cardiac medical device system, other embodiments apply to other medical and non-medical device systems, such as a device system in which detecting or providing tolerance for one or more improper energy transmission configurations is beneficial. Accordingly, the invention is not limited by this disclosure, but instead its scope is to be determined entirely by the claims.

What is claimed is:

1. A flexible circuit structure comprising:
   at least one nonconductive flexible layer comprising an electrically insulative material; and
   one or more conductive flexible circuit layers proximate the at least one nonconductive flexible layer, each of the one or more conductive flexible circuit layers comprising an electrically conductive material, wherein the one or more conductive flexible circuit layers comprises or comprise:
   a first electrical-connection-arrangement;
   a first adjacent pair of electrical loads electrically connected in series by the first electrical-connection-arrangement, the first electrical-connection-arrangement directly connecting a first electrical load of the first adjacent pair of electrical loads to a second electrical load of the first adjacent pair of electrical loads; and
   a first electrical-load-measurement lead electrically connected to the first electrical-connection-arrangement, wherein the first electrical-load-measurement lead comprises a first branched structure comprising a first plurality of conductive branches, each conductive branch of the first plurality of conductive branches electrically connected to the first electrical-connection-arrangement at a respective one of a first plurality of electrical connection points.

2. The flexible circuit structure of claim 1, wherein the flexible circuit structure comprises a plurality of electrical-connection-arrangements and a plurality of electrical loads electrically connected in series by the plurality of electrical-connection-arrangements, each electrical-connection-arrangement of the plurality of electrical-connection-arrangements electrically connecting a respective adjacent pair of electrical loads of the plurality of electrical loads, the plurality of electrical-connection-arrangements comprising the first electrical-connection-arrangement, and the plurality of electrical loads comprising the first adjacent pair of electrical loads.

3. The flexible circuit structure of claim 1, further comprising:
a second electrical-connection-arrangement electrically connected to a first electrical load of the first adjacent pair of electrical loads; and
a second electrical-load-measurement lead electrically connected to the second electrical-connection-arrangement, the first electrical-load-measurement lead and the second electrical-load-measurement lead arranged to measure voltage across the first electrical load.

4. The flexible circuit structure of claim 3,
wherein the second electrical-load measurement lead comprises a second branched structure comprising a second plurality of conductive branches, each conductive branch of the second plurality of conductive branches electrically connected to the second electrical-connection-arrangement at a respective one of a first plurality of electrical connection points.

5. The flexible circuit structure of claim 4,
wherein the number of conductive branches of the second plurality of conductive branches is different than the number of conductive branches of the first plurality of conductive branches.

6. The flexible circuit structure of claim 1, wherein the first electrical-connection-arrangement comprises one or more conductive meshes, each conductive mesh including a plurality of conductive segments spatially arranged to provide a plurality of electrical pathways defining a respective portion of an electric current flow path, the respective portion of the electric current flow path located between the electrical loads of the first adjacent pair of electrical loads, and each conductive segment of the plurality of conductive segments providing a respective portion of the plurality of electrical pathways.

7. The flexible circuit structure of claim 1, wherein the at least one nonconductive flexible layer comprises a plurality of electrically nonconductive flexible layers, and the one or more conductive flexible circuit layers comprises a plurality of conductive flexible circuit layers that are interleaved with the plurality of electrically nonconductive flexible layers.

8. The flexible circuit structure of claim 1, wherein each electrical load of the first adjacent pair of electrical loads comprises a resistive element.

9. The flexible circuit structure of claim 8, wherein each resistive element comprises a serpentine form.

10. The flexible circuit structure of claim 1,
wherein each electrical load of the first adjacent pair of electrical loads is a resistive element,
wherein the one or more conductive flexible circuit layers comprises a plurality of conductive flexible circuit layers, and
wherein at least the first electrical-connection-arrangement electrically connects at least an adjacent pair of the resistive elements by at least one via arranged to electrically connect different ones of the plurality of conductive flexible circuit layers.

11. The flexible circuit structure of claim 1,
wherein each electrical load of the first adjacent pair of electrical loads is a temperature sensor,
wherein the one or more conductive flexible circuit layers comprises a plurality of conductive flexible circuit layers, and
wherein at least the first electrical-connection-arrangement or the second electrical-connection-arrangement electrically connects at an adjacent pair of the temperature sensors by at least one via arranged to electrically connect different ones of the plurality of conductive flexible circuit layers.

12. The flexible circuit structure of claim 1, wherein each electrical load of the first adjacent pair of electrical loads is provided at least in part by a respective one of a pair of temperature sensors.

13. The flexible circuit structure of claim 1, wherein the at least one nonconductive flexible layer comprises a plurality of nonconductive flexible layers, and wherein the flexible circuit structure comprises a plurality of electrodes, each electrode of the plurality of electrodes arranged in an overlapping relationship with a respective electrical load of the first adjacent pair of electrical loads, and wherein at least a first nonconductive flexible layer of the plurality of nonconductive flexible layers is located between the plurality of electrodes and the first adjacent pair of electrical loads.

* * * * *